US012734087B2

(12) United States Patent
Schaaf et al.

(10) Patent No.: US 12,734,087 B2
(45) Date of Patent: Sep. 15, 2026

(54) PATIENT SUPPORT SYSTEMS AND METHODS FOR ASSISTING CAREGIVERS WITH PATIENT CARE

(71) Applicant: Stryker Corporation, Kalamazoo, MI (US)

(72) Inventors: Darren G. Schaaf, Portage, MI (US); Anish Paul, Kalamazoo, MI (US); Krishna Bhimavarapu, Kalamazoo, MI (US); Daniel V. Brosnan, Kalamazoo, MI (US); Aaron Douglas Furman, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 463 days.

(21) Appl. No.: 18/127,997

(22) Filed: Mar. 29, 2023

(65) Prior Publication Data

US 2023/0233391 A1 Jul. 27, 2023

Related U.S. Application Data

(63) Continuation of application No. 17/243,878, filed on Apr. 29, 2021, now abandoned, which is a (Continued)

(51) Int. Cl.
*A61G 7/018* (2006.01)
*A61B 5/00* (2006.01)
(Continued)

(52) U.S. Cl.
CPC ............ *A61G 7/018* (2013.01); *A61B 5/6801* (2013.01); *A61B 5/6891* (2013.01); *A61G 5/006* (2013.01);
(Continued)

(58) Field of Classification Search
CPC .......... A61G 7/018; A61G 5/006; A61G 5/10; A61G 2203/10; A61G 2203/16;
(Continued)

(56) References Cited

U.S. PATENT DOCUMENTS 1,025,915 A 5/1912 Hoff
2,587,068 A 2/1952 Sanders
(Continued)

FOREIGN PATENT DOCUMENTS

AU 1742699 A 5/1999
CA 2122515 A1 10/1995
(Continued)

OTHER PUBLICATIONS

Astral Health Care, "Opthalmology Day Surgery Chair", URL: http://astralhealthcare.com/?product=opthalmology-day-surgery-chair, downloaded Feb. 13, 2020.
(Continued)

*Primary Examiner* — Justin C Mikowski
*Assistant Examiner* — George Samuel Gines
(74) *Attorney, Agent, or Firm* — Howard & Howard Attorneys PLLC

(57) ABSTRACT

A patient support system comprises a patient support apparatus for patients. The patient support apparatus also comprises an actuatable device that perform one or more predetermined functions on the patient support apparatus. A controller is provided to control the rate of operation of the actuatable devices based on a user input or a patient condition.

19 Claims, 21 Drawing Sheets

Related U.S. Application Data continuation of application No. 15/369,188, filed on Dec. 5, 2016, now Pat. No. 11,020,295.

(60) Provisional application No. 62/271,054, filed on Dec. 22, 2015.

(51) Int. Cl.
*A61G 5/00* (2006.01)
*A61G 5/10* (2006.01)

(52) U.S. Cl.
CPC ............ *A61G 5/10* (2013.01); *A61G 2203/10* (2013.01); *A61G 2203/16* (2013.01); *A61G 2203/30* (2013.01); *A61G 2203/70* (2013.01)

(58) Field of Classification Search
CPC ............ A61G 2203/30; A61G 2203/70; A61B 5/6801; A61B 5/6891
See application file for complete search history.

(56) References Cited

U.S. PATENT DOCUMENTS

| | | | |
|---|---|---|---|
| 3,091,426 | A | 5/1963 | Bogart |
| 3,191,196 | A | 6/1965 | Holm |
| 3,578,379 | A | 5/1971 | Taylor et al. |
| 3,640,566 | A | 2/1972 | Hodge |
| 3,787,089 | A | 1/1974 | Wrethander |
| 3,936,893 | A | 2/1976 | Anderson et al. |
| 4,119,342 | A | 10/1978 | Jones |
| 4,183,578 | A | 1/1980 | Naganawa |
| 4,850,645 | A | 7/1989 | Crockett |
| 4,913,264 | A | 4/1990 | Voves et al. |
| 4,997,200 | A | 3/1991 | Earls |
| 5,062,151 | A | 10/1991 | Shipley |
| 5,112,076 | A | 5/1992 | Wilson |
| 5,219,204 | A | 6/1993 | Bathrick et al. |
| 5,230,113 | A | 7/1993 | Foster et al. |
| 5,242,138 | A | 9/1993 | Komberg |
| 5,265,935 | A | 11/1993 | Geisler et al. |
| 5,342,114 | A | 8/1994 | Burke et al. |
| 5,346,280 | A | 9/1994 | Deumite |
| 5,366,036 | A | 11/1994 | Perry |
| 5,369,821 | A | 12/1994 | Richards et al. |
| 5,419,571 | A | 5/1995 | Vaughan |
| 5,458,349 | A | 10/1995 | Mung-Tung |
| 5,515,561 | A | 5/1996 | Suggitt et al. |
| 5,547,245 | A | 8/1996 | Knouse |
| 5,556,121 | A | 9/1996 | Pillot |
| 5,641,201 | A | 6/1997 | Casey et al. |
| 5,699,038 | A | 12/1997 | Ulrich et al. |
| 5,772,226 | A | 6/1998 | Bobichon |
| 5,896,602 | A | 4/1999 | Marblestone |
| 5,917,425 | A | 6/1999 | Crimmins et al. |
| 5,984,411 | A | 11/1999 | Galumbeck |
| 6,017,354 | A | 1/2000 | Culp et al. |
| 6,024,411 | A | 2/2000 | Pesta et al. |
| 6,053,578 | A | 4/2000 | van Hekken et al. |
| 6,142,568 | A | 11/2000 | Abelbeck et al. |
| 6,161,229 | A | 12/2000 | Ryan et al. |
| 6,296,313 | B1 | 10/2001 | Wu |
| 6,338,531 | B1 | 1/2002 | Hausherr et al. |
| 6,454,285 | B1 | 9/2002 | Koenig |
| 6,533,304 | B2 | 3/2003 | Lizama-Troncoso et al. |
| 6,533,353 | B2 | 3/2003 | Johnston |
| 6,540,250 | B1 | 4/2003 | Peterson |
| 6,557,940 | B2 | 5/2003 | Hayashi et al. |
| 6,594,837 | B2 | 7/2003 | Khait |
| 6,612,985 | B2 | 9/2003 | Eiffert et al. |
| 6,701,546 | B2 | 3/2004 | Hodgetts |
| 6,715,784 | B2 | 4/2004 | Koerlin et al. |
| 6,792,633 | B1 | 9/2004 | Ito |
| 6,886,194 | B2 | 5/2005 | Hodgetts |
| 6,907,630 | B2 | 6/2005 | Treon |
| 7,003,830 | B2 | 2/2006 | Ito |
| 7,007,963 | B2 | 3/2006 | Meyer |
| 7,021,713 | B2 | 4/2006 | Kao et al. |
| 7,058,999 | B2 | 6/2006 | Horitani et al. |
| 7,090,297 | B2 | 8/2006 | Mohn et al. |
| 7,100,242 | B2 | 9/2006 | Maierholzner |
| 7,219,912 | B2 | 5/2007 | Meyer |
| 7,284,799 | B2 | 10/2007 | Chung |
| 7,398,571 | B2 | 7/2008 | Souke et al. |
| 7,399,205 | B2 | 7/2008 | McNeely et al. |
| 7,410,055 | B2 | 8/2008 | Plank |
| 7,419,176 | B2 | 9/2008 | Perk |
| 7,455,360 | B2 | 11/2008 | White et al. |
| 7,458,119 | B2 | 12/2008 | Hornbach et al. |
| 7,472,438 | B2 | 1/2009 | Karmer, Jr. et al. |
| 7,570,152 | B2 | 8/2009 | Smith et al. |
| 7,631,937 | B2 | 12/2009 | Robertson |
| 7,638,958 | B2 | 12/2009 | Philipp et al. |
| 7,708,093 | B1 | 5/2010 | Baker |
| 7,725,968 | B2 | 6/2010 | Lambarth |
| 7,746,218 | B2 | 6/2010 | Collins, Jr. et al. |
| 7,815,209 | B2 | 10/2010 | Porcheron |
| 7,862,123 | B2 | 1/2011 | Baker et al. |
| 7,874,620 | B2 | 1/2011 | Kooistra et al. |
| 7,887,133 | B2 | 2/2011 | Perk |
| 7,896,442 | B2 | 3/2011 | White |
| 7,899,006 | B2 | 3/2011 | Boyd |
| 7,979,931 | B2 | 7/2011 | Wurdeman |
| 8,056,160 | B2 | 11/2011 | Poulos et al. |
| 8,065,024 | B2 | 11/2011 | Nagaoka et al. |
| 8,069,514 | B2 | 12/2011 | Poulos et al. |
| 8,104,118 | B2 | 1/2012 | Derenne et al. |
| 8,123,664 | B2 | 2/2012 | Okken et al. |
| 8,127,380 | B2 | 3/2012 | Wurdeman |
| 8,128,120 | B2 | 3/2012 | Porcheron |
| 8,272,087 | B2 | 9/2012 | Westermann |
| 8,319,633 | B2 | 11/2012 | Becker et al. |
| 8,334,779 | B2 | 12/2012 | Zerhusen et al. |
| 8,336,133 | B2 | 12/2012 | Palay et al. |
| 8,414,074 | B2 | 4/2013 | Kramer et al. |
| 8,437,876 | B2 | 5/2013 | Receveur et al. |
| 8,439,416 | B2 | 5/2013 | Lambarth et al. |
| 8,461,968 | B2 | 6/2013 | Ball et al. |
| 8,499,385 | B2 | 8/2013 | Horitani |
| 8,516,637 | B2 | 8/2013 | Karwal et al. |
| 8,522,379 | B2 | 9/2013 | Turner |
| 8,535,342 | B2 | 9/2013 | Malackowski et al. |
| 8,544,866 | B2 | 10/2013 | Noonan et al. |
| 8,631,524 | B2 | 1/2014 | Derenne et al. |
| 8,756,078 | B2 | 6/2014 | Collins, Jr. et al. |
| 8,844,078 | B2 | 9/2014 | Hornbach et al. |
| 8,856,982 | B1 | 10/2014 | Kalivas |
| 8,887,272 | B2 | 11/2014 | Urness et al. |
| 8,910,329 | B2 | 12/2014 | Turner et al. |
| 8,959,681 | B2 | 2/2015 | Richards |
| 9,138,173 | B2 | 9/2015 | Penninger et al. |
| 9,259,369 | B2 | 2/2016 | Derenne et al. |
| 9,320,444 | B2 | 4/2016 | Hayes et al. |
| 9,569,591 | B2 | 2/2017 | Vanderpohl, III |
| 9,782,005 | B2 | 10/2017 | Paul et al. |
| 10,290,373 | B2 | 5/2019 | Jäger et al. |
| 10,376,214 | B2 | 8/2019 | Hayes et al. |
| 10,813,806 | B2 | 10/2020 | Paul |
| 11,020,295 | B2 | 6/2021 | Schaaf et al. |
| 11,571,071 | B2 | 2/2023 | Hosokawa et al. |
| 11,571,072 | B2 | 2/2023 | Kubota et al. |
| 11,786,426 | B2 | 10/2023 | Murai |
| 2002/0084903 | A1 | 7/2002 | Chaco |
| 2002/0145534 | A1 | 10/2002 | Dempsey |
| 2002/0167417 | A1 | 11/2002 | Welles et al. |
| 2002/0183979 | A1 | 12/2002 | Wildman |
| 2002/0196141 | A1 | 12/2002 | Boone et al. |
| 2005/0046129 | A1 | 3/2005 | Antonishak et al. |
| 2006/0238007 | A1 | 10/2006 | Lin |
| 2007/0089238 | A1 | 4/2007 | Kramer et al. |
| 2007/0114828 | A1 | 5/2007 | Corcoran |
| 2007/0157385 | A1 | 7/2007 | Lemire et al. |
| 2008/0007103 | A1 | 1/2008 | Welles et al. |
| 2008/0106060 | A1 | 5/2008 | Knopf |

(56) References Cited

U.S. PATENT DOCUMENTS

2008/0172789 A1* 7/2008 Elliot .................. A61G 7/0527 5/616
2008/0234555 A1* 9/2008 Lafleche .................. A61B 5/00 600/300
2008/0242521 A1 10/2008 Einav
2008/0300777 A1* 12/2008 Fehr ...................... G01C 21/20 701/532
2010/0017072 A1 1/2010 Emilsson
2010/0064439 A1 3/2010 Soltani
2010/0066056 A1 3/2010 Li et al.
2010/0095453 A1 4/2010 Lin et al.
2010/0186163 A1 7/2010 Sorribes
2010/0212087 A1 8/2010 Leib et al.
2011/0078113 A1 3/2011 Franz
2011/0084529 A1 4/2011 Huang
2011/0087113 A1 4/2011 Mack et al.
2011/0121625 A1 5/2011 Lipford
2011/0168478 A1 7/2011 Kuo et al.
2011/0227314 A1 9/2011 Lowenthal et al.
2011/0248530 A1 10/2011 Sartisohn
2011/0263950 A1 10/2011 Larson et al.
2011/0266840 A1 11/2011 Wu
2012/0073054 A1 3/2012 O'Keefe et al.
2012/0104818 A1 5/2012 Morris
2012/0146378 A1 6/2012 Lokken et al.
2012/0174319 A1 7/2012 Menkedick et al.
2012/0181832 A1 7/2012 Lin et al.
2012/0259248 A1 10/2012 Receveur
2012/0316884 A1* 12/2012 Rozaieski ................ A61G 5/10 704/E21.001
2013/0007960 A1 1/2013 Manouchehri et al.
2013/0020779 A1 1/2013 Green et al.
2013/0026737 A1 1/2013 Pizzi Spadoni
2013/0125310 A1 5/2013 Manouchehri
2013/0184003 A1 7/2013 Alizadeh-Shabdiz et al.
2013/0205501 A1 8/2013 Robertson et al.
2013/0219622 A1 8/2013 Hornbach et al.
2013/0244692 A1 9/2013 Kelly et al.
2013/0253291 A1 9/2013 Dixon et al.
2014/0007346 A1 1/2014 Lachenbruch
2014/0080413 A1 3/2014 Hayes et al.
2014/0090171 A1* 4/2014 Hyde ................... G05D 1/0234 701/2
2014/0115784 A1 5/2014 Johannigman et al.
2014/0169795 A1* 6/2014 Clough ................. H04W 88/02 398/106
2014/0265497 A1 9/2014 Hough et al.
2014/0265500 A1 9/2014 Hough et al.
2014/0289959 A1 10/2014 Hjort et al.
2014/0296755 A1 10/2014 Lack et al.
2014/0297327 A1 10/2014 Heil et al.
2014/0310876 A1 10/2014 Roussy et al.
2014/0346745 A1 11/2014 Ganel
2015/0060162 A1* 3/2015 Goffer .................... A61G 5/124 180/41
2015/0081335 A1 3/2015 Dixon et al.
2015/0096815 A1 4/2015 Ottenweller et al.
2015/0105636 A1 4/2015 Hayman et al.
2015/0129333 A1 5/2015 Morris et al.
2015/0137988 A1 5/2015 Gravenstein et al.
2015/0190293 A1 7/2015 Hacikadiroglu et al.
2015/0216474 A1 8/2015 Riley et al.
2015/0351982 A1* 12/2015 Krenik .................. A47C 23/06 5/616
2016/0014030 A1 1/2016 Thyni et al.
2016/0022039 A1 1/2016 Paul et al.
2016/0051427 A1 2/2016 Purwar et al.
2016/0120717 A1 5/2016 Wurdeman
2016/0140307 A1 5/2016 Brosnan et al.
2016/0193095 A1 7/2016 Roussy et al.
2016/0235610 A1 8/2016 Drake
2016/0242681 A1 8/2016 Shen et al.
2016/0331615 A1 11/2016 Fakhrizadeh
2016/0367420 A1 12/2016 Zerhusen et al.
2017/0035628 A1 2/2017 Naber et al.
2017/0143565 A1 5/2017 Childs et al.
2017/0143566 A1 5/2017 Elku et al.
2017/0172827 A1 6/2017 Schaaf et al.
2017/0172829 A1 6/2017 Tessmer et al.
2017/0340495 A1 11/2017 Paul
2021/0244586 A1 8/2021 Schaaf et al.

FOREIGN PATENT DOCUMENTS

CA 2122686 A1 11/1995
CA 2800154 A1 11/2010
CN 1152863 A 6/1997
CN 2294717 Y 10/1998
CN 2915071 Y 6/2007
CN 200960241 Y 10/2007
CN 204306991 U 5/2015
CN 104887425 A 9/2015
CN 204655317 U 9/2015
DE 2749146 A1 5/1978
DE 20303000 U1 7/2003
EP 0656183 A2 6/1995
EP 1031337 A1 8/2000
EP 1199027 A2 4/2002
EP 1789278 A2 5/2007
EP 1859765 A2 11/2007
EP 1965679 A2 9/2008
EP 1997466 A2 12/2008
EP 1623666 B1 12/2009
EP 1214035 B1 3/2010
EP 2327385 A2 6/2011
EP 1226803 B1 8/2011
EP 2105117 B1 12/2011
EP 2910226 A1 8/2015
EP 2725507 B1 2/2016
EP 2327385 B1 3/2016
GB 1486991 A 9/1977
JP H078521 A 1/1995
JP H078521 B2 2/1995
JP H11104190 A 4/1999
JP 2010154929 A 7/2010
JP 4896358 B2 3/2012
JP 5055523 B2 10/2012
JP 5117726 B2 1/2013
KR 20130076922 A 7/2013
TW 201019894 A 6/2010
WO 9014816 A1 12/1990
WO 9834577 A1 8/1998
WO 0185085 A2 11/2001
WO 03105095 A2 12/2003
WO 2004093023 A2 10/2004
WO 2004104619 A1 12/2004
WO 2004106419 A1 12/2004
WO 2005074369 A2 8/2005
WO 2006023447 A2 3/2006
WO 2007072501 A2 6/2007
WO 2007075699 A2 7/2007
WO 2007075701 A2 7/2007
WO 2011113070 A1 9/2011
WO 2014152550 A2 9/2014
WO 2015032003 A1 3/2015
WO 2016108582 A1 7/2016

OTHER PUBLICATIONS

English language abstract and machine-assisted English translation for JP 2010-154929 extracted from espacenet. com database on Jan. 23, 2020, 17 pages.
English language abstract and machine-assisted translation for CN104887425 extracted from espacenet.com Sep. 13, 2017; 6 pages.
English language abstract and machine-assisted translation for CN200960241 extracted from espacenet.com on Apr. 26, 2018; 5 pages.
English language abstract and machine-assisted translation for CN204306991 extracted from espacenet.com on Apr. 26, 2018; 4 pages.

(56) References Cited

OTHER PUBLICATIONS

English language abstract and machine-assisted translation for CN204655317 extracted from espacenet.com on Apr. 26, 2018; 8 pages.
English language abstract and machine-assisted translation for CN2915071 extracted from espacenet.com on Apr. 26, 2018; 4 pages.
English language abstract and machine-assisted translation for DE20303000 extracted from espacenet.com on Apr. 26, 2018; 5 pages.
English language abstract and machine-assisted translation for DE2749146 extracted from espacenet.com on Apr. 26, 2018; 9 pages.
English language abstract and machine-assisted translation for JP5117726 extracted from espacenet.com on Apr. 26, 2018; 34 pages.
English language abstract and machine-assisted translation for JPH 07-8521 A extracted from espacenet.com on May 5, 2021, 6 pages.
English language abstract and machine-assisted translation for JPH078521 extracted from espacenet.com on Apr. 26, 2018; 6 pages.
English language abstract and machine-assisted translation for JPH11104190 extracted from espacenet.com on Apr. 26, 2018; 9 pages.
English language abstract and machine-assisted translation for TW201019894 extracted from espacenet.com Sep. 13, 2017; 8 pages.
English language abstract and machine-assisted translation for WO2004106419 extracted from espacenet.com on Apr. 26, 2018; 25 pages.
English language abstract for CN2294717 extracted from espacenet.com on Apr. 26, 2018; 1 page.
English language abstract for KR20130076922 extracted from espacenet.com on Apr. 17, 2018; 1 page.
Haworth, "Fern(TM) Seating Adjustment" brochure; 5 pages.
Recliners. LA, "Lift Chairs are Improving Life for Young and Old", Mar. 15, 2016; URL: https://www.recliners.la/blogs/motion-furniture-buying-guide/113167876.
Recliners. LA, Stellar 550 Large Lift Chair Recliner (Ultracomfort), available as early as Dec. 22, 2015, URL: https://www.recliners.la/products/ultra-comfort-stellar-550-large-lift-chair.
Ultra Comfort America, "Stellar Comfort UC550-L Webpage", https://www.ultracomfort.com/our-collection/stellar/uc550-I/, 2014, 2 pages.
Youtube, "Memory Seat Escape", Nov. 4, 2013, URL: https://www.youtube.com/watch?v=xlghNmAK-7A.

* cited by examiner

PS
66
B16
241
228
NCP
60
PCP
58
38
46
44
42
48
40
242
244
56
54
62
36
30
32
34
76
68
70
72
226
222

104
PS
111
100
102
111
106
110
110

104
PS
111
102
106
111
110
110

104
PS
111
102
111
106
110
110

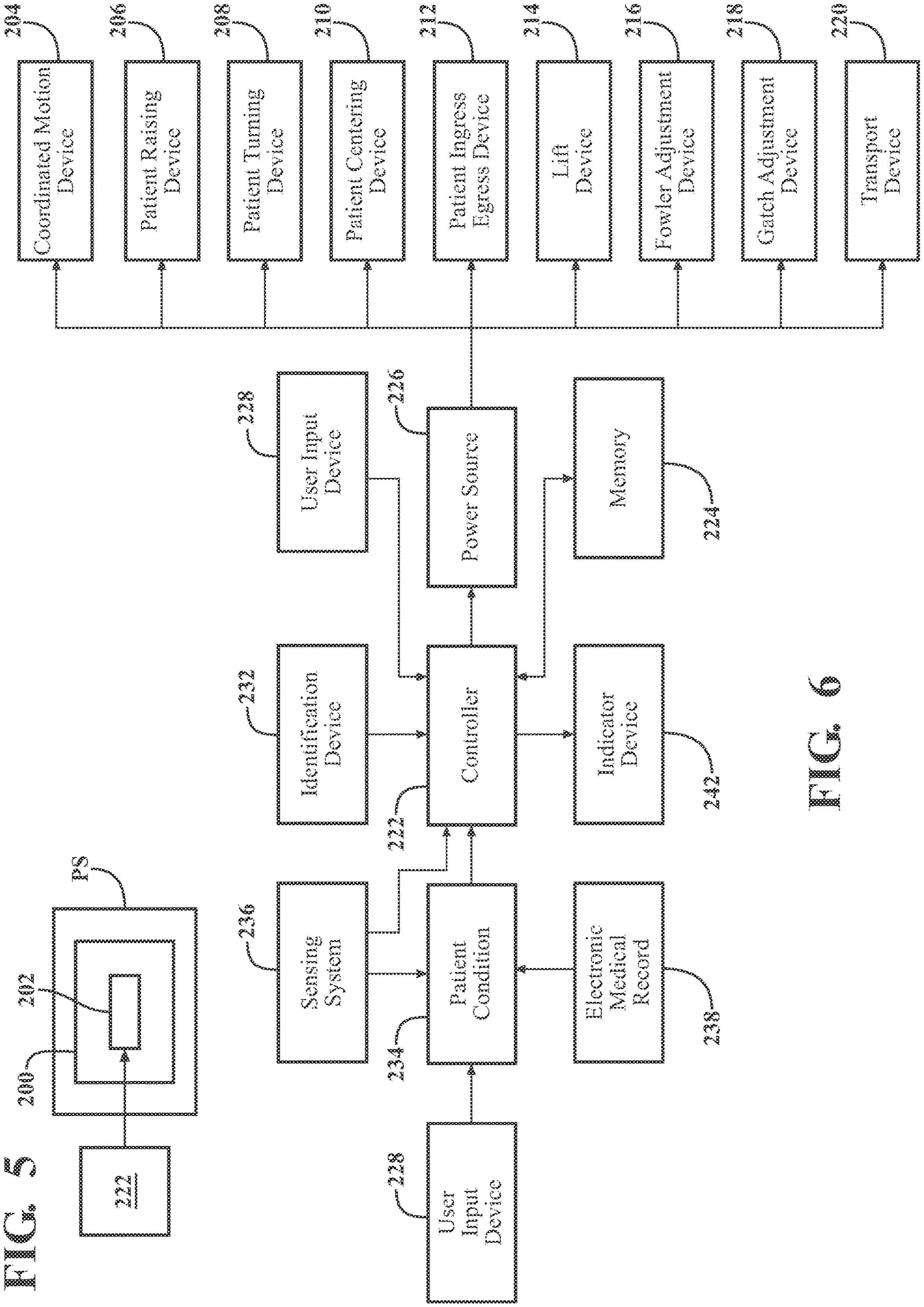

222
200
202
PS
Coordinated Motion Device
204
Patient Raising Device
206
Patient Turning Device
208
Patient Centering Device
210
Patient Ingress Egress Device
212
Lift Device
214
Fowler Adjustment Device
216
Gatch Adjustment Device
218
Transport Device
220
User Input Device
228
Power Source
226
Memory
224
Identification Device
232
Controller
222
Indicator Device
242
Sensing System
236
Patient Condition
234
Electronic Medical Record
238
User Input Device
228

NECK INJURY
Voice Enable
Fast
Medium
Slow
Automatic Mode
Empty Mode
CPR Mode
Patient Mode
Cleaning Mode
Transport Mode
6"
8"
230
231
244
242
B1
B2
B3
B4
B5
B6
B7
B8
B9
B10
B11
B12
B13
B14
B15
B17
B18
B19
B20
B29
B30
B31
NCP FIG. 19A
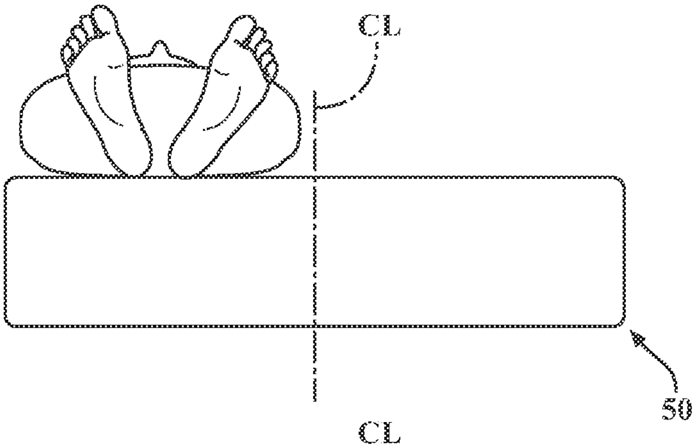
FIG. 19B
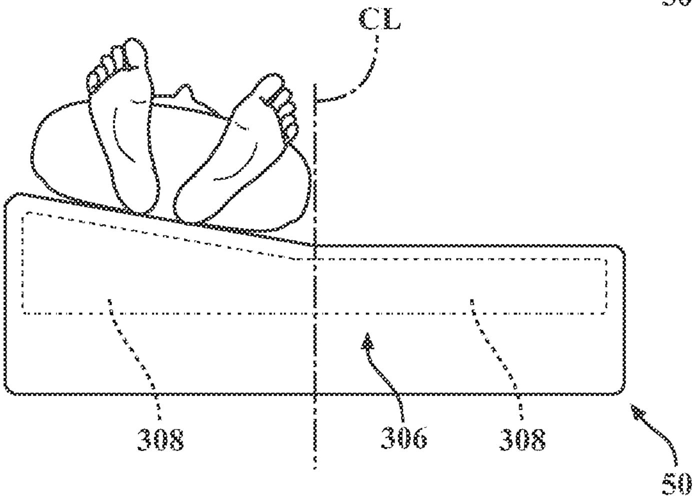
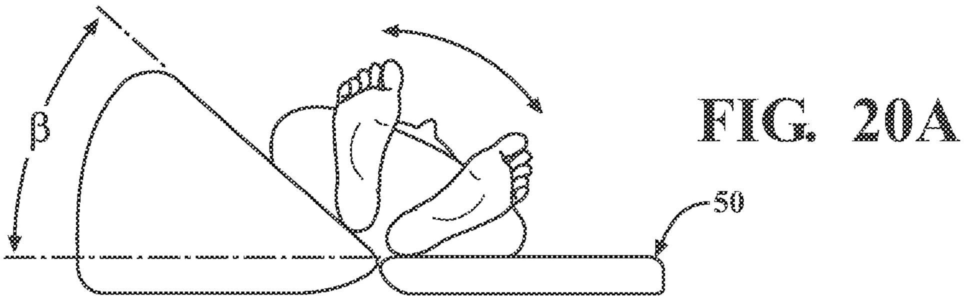
FIG. 20A
FIG. 20B
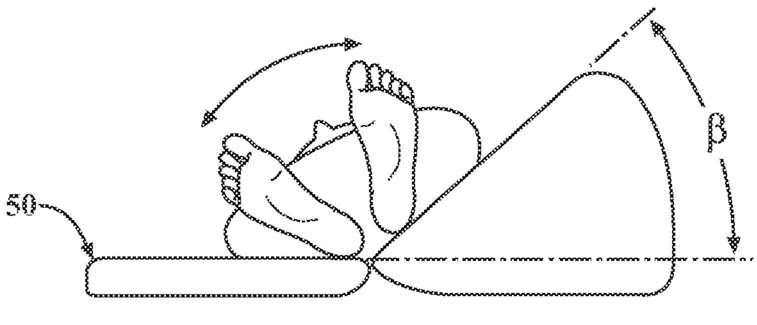

222
Controller
214
240
42
30
228
406
400
402
36
404
402
34
PS
408

228
PS
240
510
241
46
40
506
42
241
44
241
216
508
218
38
500
502
504
36
Controller
222
34

PATIENT SUPPORT SYSTEMS AND METHODS FOR ASSISTING CAREGIVERS WITH PATIENT CARE

CROSS-REFERENCE TO RELATED APPLICATIONS

This application is a Continuation of U.S. patent application Ser. No. 17/243,878 filed on Apr. 29, 2021, which is a Continuation of U.S. patent application Ser. No. 15/369,188 filed on Dec. 5, 2016 and issued as U.S. Pat. No. 11,020,295 on Jun. 1, 2021, which claims the benefit of and priority to U.S. Provisional Patent Application No. 62/271,054 filed on Dec. 22, 2015, the disclosures of each of which are hereby incorporated by reference in their entirety.

BACKGROUND

Patient support systems facilitate care of patients in a health care setting. Patient support systems comprise patient support apparatuses such as, for example, hospital beds, stretchers, cots, tables, and wheelchairs. Conventional patient support apparatuses comprise a base and a patient support surface upon which the patient is supported. Often, these patient support apparatuses have one or more actuatable devices to perform one or more functions on the patient support apparatus. These functions can include lifting and lowering the patient support surface, raising a patient from a slouched position, turning a patient, centering a patient, and the like. When the caregiver wishes to operate an actuatable device to perform a function, the caregiver often actuates a user input device, often in the form of a button on a control panel. To continue performing the function, the caregiver is required to continue depressing the button until a desired outcome is achieved, e.g., the patient support surface is lifted to a desired height, the patient is sufficiently raised from the slouched position to a desired position, etc. A default rate of operation of the actuatable device may be too fast for certain patient conditions, such as when the patient has a history of skin lesions. Furthermore, the default rate of operation may be slower than desired, especially when the patient is not disposed on the patient support apparatus.

A patient support system designed to control the rate of operation of the actuatable devices and overcome one or more of the aforementioned challenges is desired.

BRIEF DESCRIPTION OF THE DRAWINGS

FIG. 5 is a simplified schematic view of a control system.

FIG. 6 is a schematic view of a control system.

FIGS. 19A and 19B are illustrations of centering the patient relative to a centerline.

FIGS. 20A and 20B are illustrations of turning a patient.

DETAILED DESCRIPTION

Figure 1A:
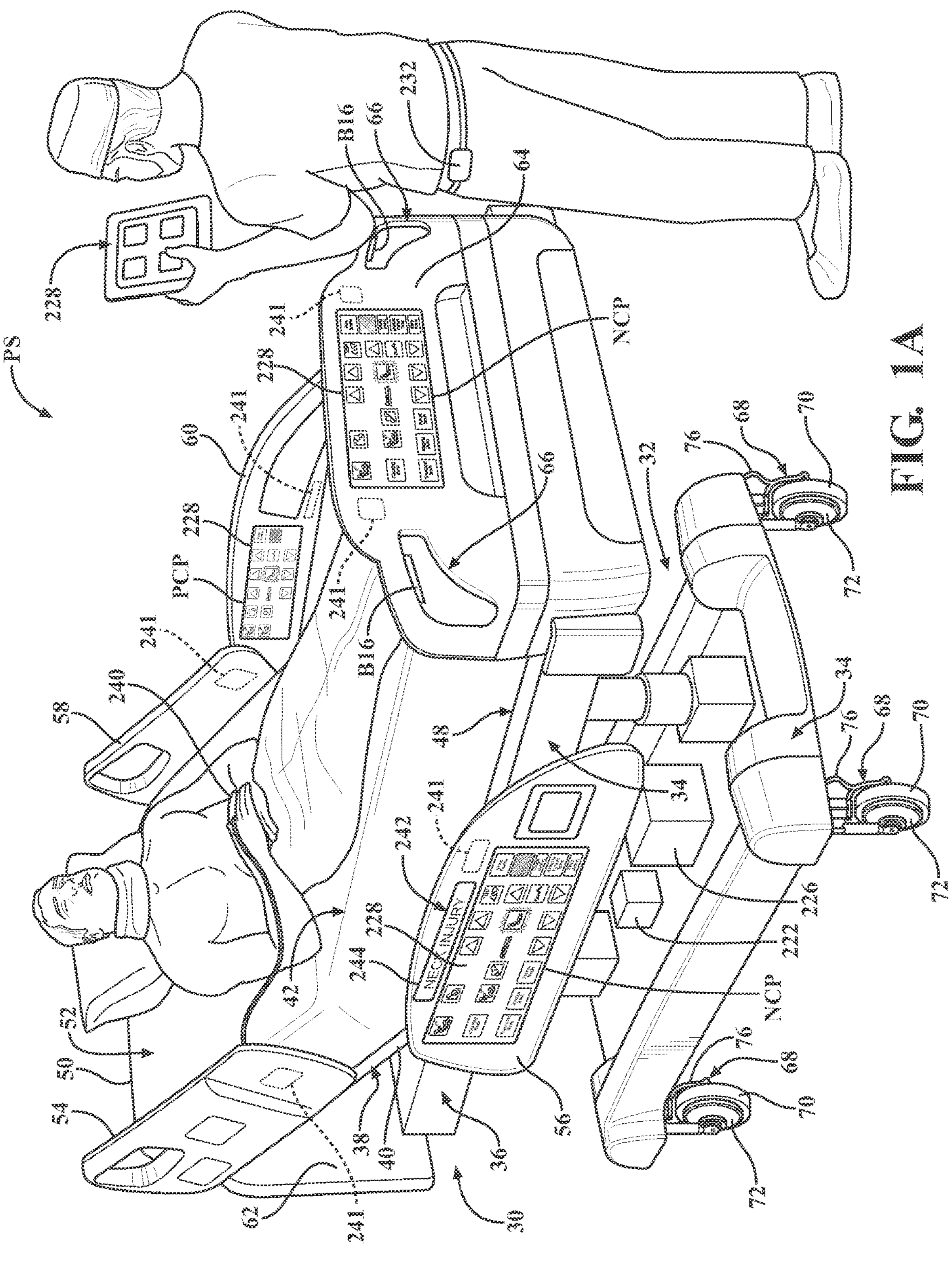
FIG. 1A is perspective view of a patient support apparatus including a mattress.
Figure 1B:
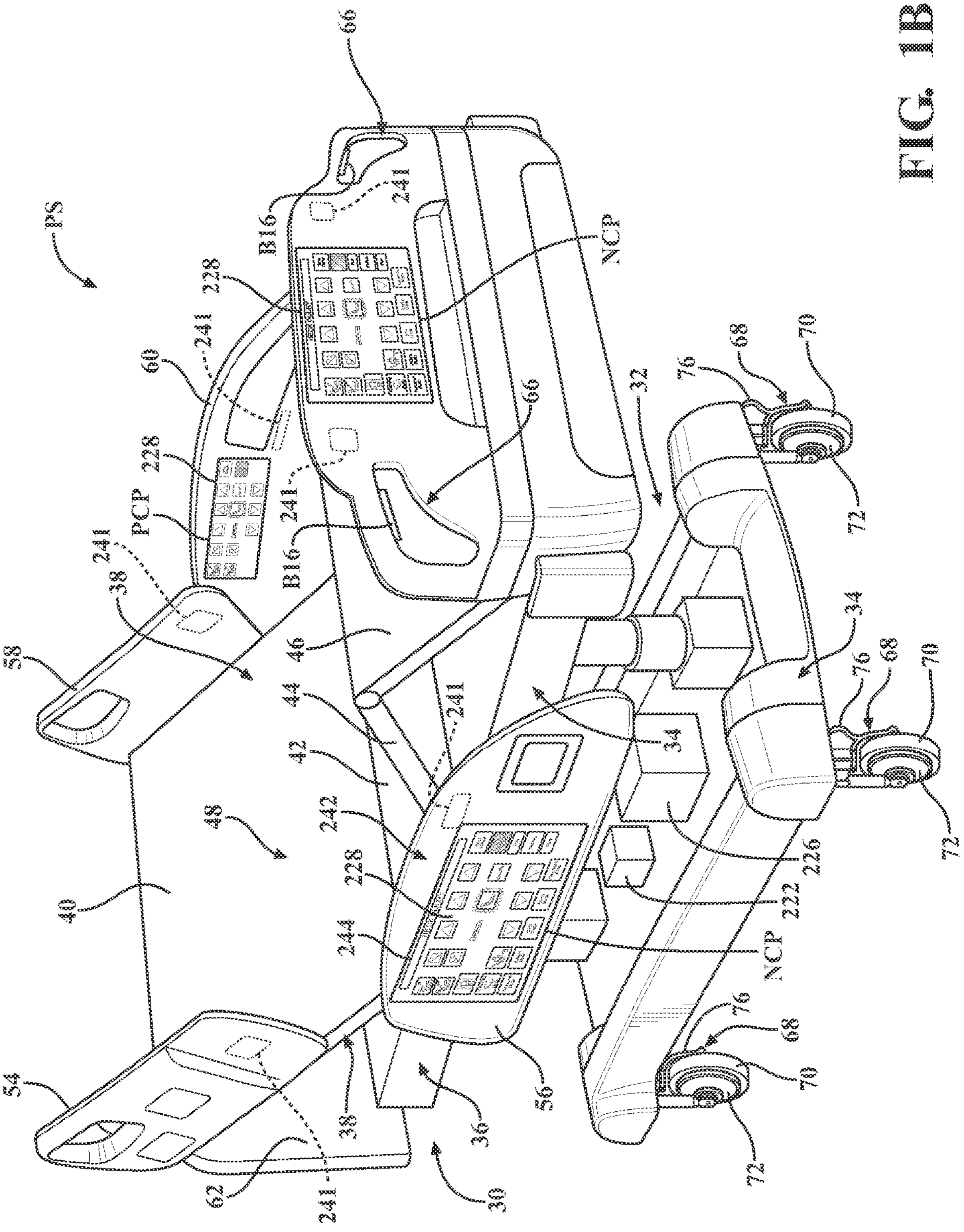
FIG. 1B is perspective view of the patient support apparatus of FIG. 1A without the mattress.

Referring to FIGS. 1A and 1B, a patient support system PS comprising a patient support apparatus 30 is shown for supporting a patient in a health care setting. The patient support apparatus 30 illustrated in FIGS. 1A and 1B comprises a hospital bed. In other embodiments, however, the patient support apparatus 30 may comprise a stretcher, cot, table, chair, wheelchair, or similar apparatus utilized in the care of a patient.

A support structure 32 provides support for the patient. The support structure 32 illustrated in FIGS. 1A and 1B comprises a base 34 and an intermediate frame 36. The intermediate frame 36 is spaced above the base 34. The support structure 32 also comprises a patient support deck 38 disposed on the intermediate frame 36. Referring specifically to FIG. 1B, the patient support deck 38 comprises several sections, some of which are pivotable relative to the intermediate frame 36, such as a fowler section 40, a seat section 42, a thigh section 44, and a foot section 46. The patient support deck 38 provides a patient support surface 48 upon which the patient is supported.

Referring to FIG. 1A, a mattress 50 is disposed on the patient support deck 38. The mattress 50 comprises a secondary patient support surface 52 upon which the patient is supported. The base 34, intermediate frame 36, patient support deck 38, and patient support surfaces 48, 52 each have a head end and a foot end corresponding to the designated placement of the patient's head and feet on the patient support apparatus 30. The construction of the support structure 32 may take on any known or conventional design, and is not limited to that specifically set forth above. In addition, the mattress 50 may be omitted in certain embodiments, such that the patient rests directly on the patient support surface 48 (see FIG. 1B).

Side rails 54, 56, 58, 60 are supported by the base 34. A first side rail 54 is positioned at a right head end of the intermediate frame 36. A second side rail 56 is positioned at a right foot end of the intermediate frame 36. A third side rail 58 is positioned at a left head end of the intermediate frame 36. A fourth side rail 60 is positioned at a left foot end of the intermediate frame 36. If the patient support apparatus 30 is a stretcher or a cot, there may be fewer side rails. The side rails 54, 56, 58, 60 are movable between a raised position in which they block ingress and egress into and out of the patient support apparatus 30, and a lowered position in which they are not an obstacle to such ingress and egress. The side rails 54, 56, 58, 60 may also be movable to one or more intermediate positions between the raised position and the lowered position. In still other configurations, the patient support apparatus 30 may not comprise any side rails.

A headboard 62 and a footboard 64 are coupled to the intermediate frame 36. In other embodiments, when the headboard 62 and footboard 64 are included, the headboard 62 and footboard 64 may be coupled to other locations on the patient support apparatus 30, such as the base 34. In still other embodiments, the patient support apparatus 30 does not include the headboard 62 and/or the footboard 64.

Caregiver interfaces 66, such as handles, are shown integrated into the footboard 64 to facilitate movement of the patient support apparatus 30 over floor surfaces. Additional caregiver interfaces 66 may be integrated into the headboard 62 and/or other components of the patient support apparatus 30. The caregiver interfaces 66 are graspable by the caregiver to manipulate the patient support apparatus 30 for movement.

Other forms of the caregiver interface 66 are also contemplated. The caregiver interface 66 may comprise one or more handles coupled to the intermediate frame 36. The caregiver interface 66 may simply be a surface on the patient support apparatus 30 upon which the caregiver logically applies force to cause movement of the patient support apparatus 30 in one or more directions, also referred to as a push location. This may comprise one or more surfaces on the intermediate frame 36 or base 34. This could also comprise one or more surfaces on or adjacent to the headboard 62, footboard 64, and/or side rails 54, 56, 58, 60. In other embodiments, the caregiver interface 66 may comprise separate handles for each hand of the caregiver. For example, the caregiver interface 66 may comprise two handles.

Figure 2:
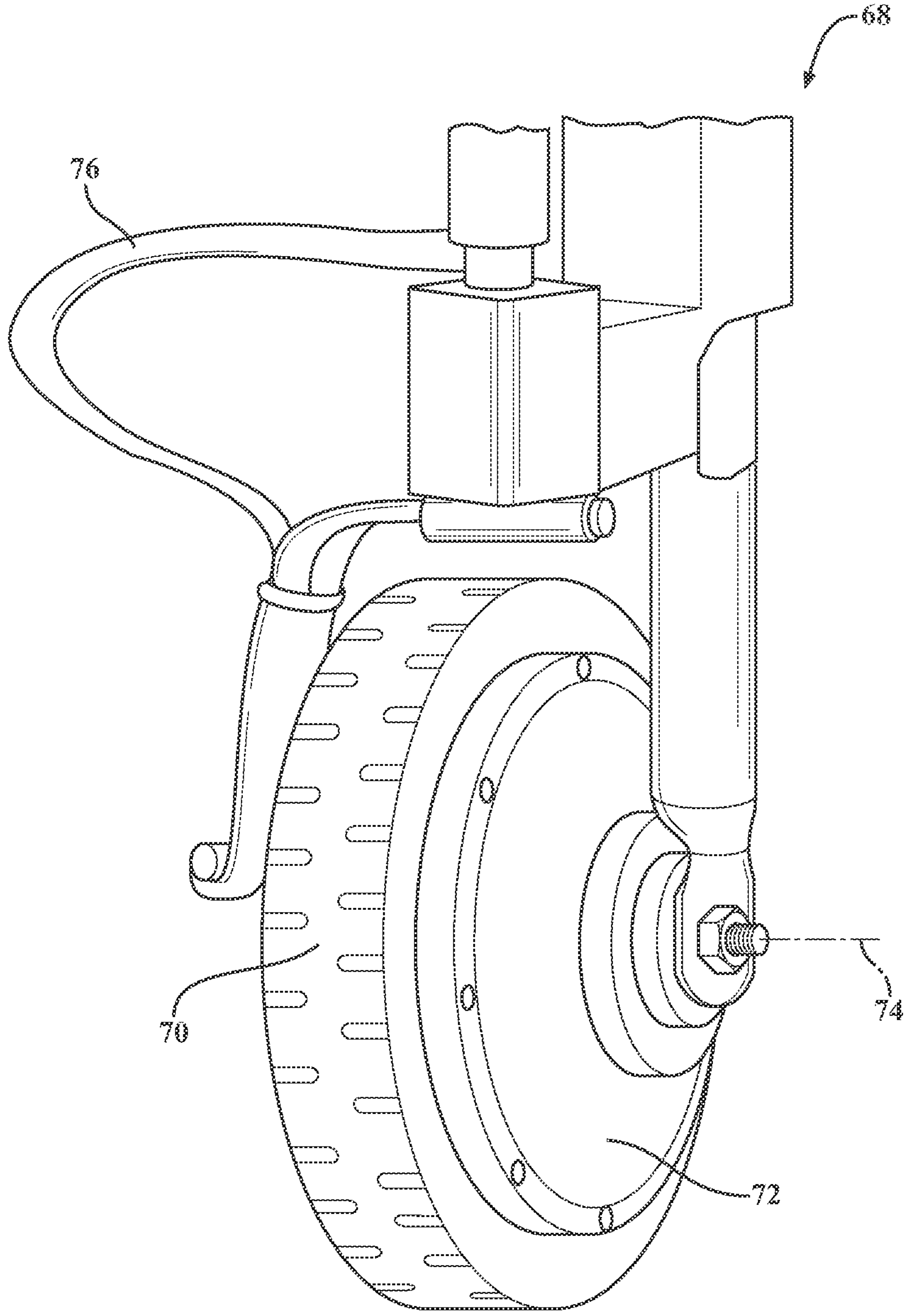
FIG. 2 is a perspective view of a powered wheel assembly.

The patient support apparatus 30 may include a powered wheel assembly 68. Referring to FIG. 2, the powered wheel assembly 68 may comprise a wheel 70 and a wheel motor 72. The wheel motor 72 may be located inside of wheel 70 and is configured to cause wheel 70 to rotate about a generally horizontal rotational axis 74. Wheel motor 72 receives its commands and/or electrical power through a pair of cables 76 that connect thereto. Wheel motor 72 rotates wheel 70 about the rotational axis 74. In the embodiment shown, each wheel 70 comprises a corresponding wheel motor 72. The powered wheel assemblies 68 are coupled to the base 34 to facilitate transport over the floor surfaces. The powered wheel assemblies 68 are arranged in each of four quadrants of the base 34 adjacent to corners of the base 34. In the embodiment shown, the powered wheel assemblies 68 are able to rotate and swivel relative to the base 34 during transport. It should be understood that various configurations of the powered wheel assemblies 68 are contemplated. In addition, in some embodiments, wheels that are not powered may be used, and these wheels may be caster wheels, non-steerable, steerable, or combinations thereof. Additional wheels are also contemplated. For example, the patient support apparatus 30 may comprise four non-powered, non-steerable wheels, along with one or more powered wheel assemblies 68. In some cases, the patient support apparatus 30 may not include any wheels. Alternatively still, one or more auxiliary wheels (powered or non-powered), which are movable between stowed positions and deployed positions, may be coupled to the base 34. A fifth wheel may also be arranged substantially in a center of the base 34.

Figure 3:
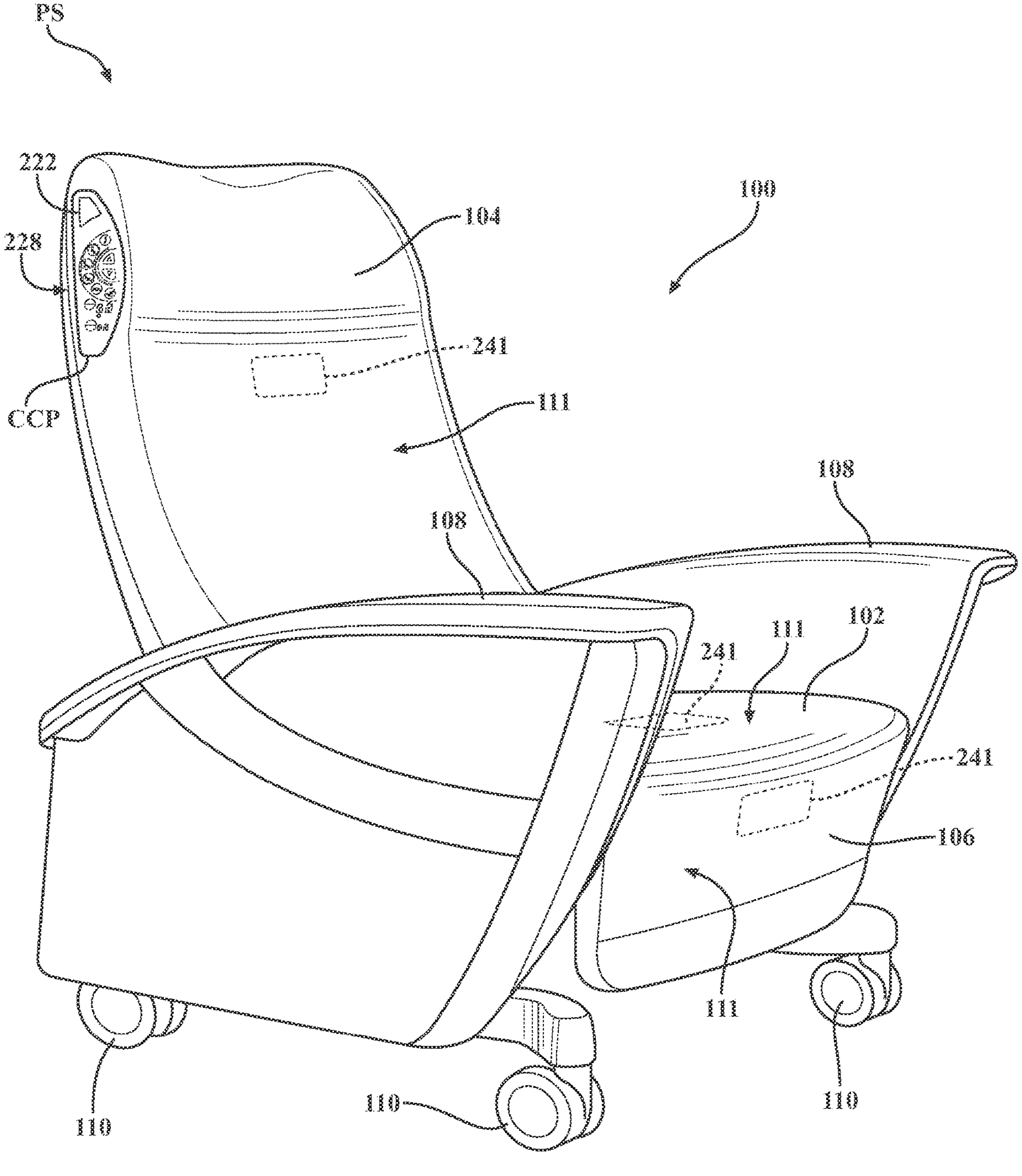
FIG. 3 is a perspective view of a coordinated motion device.

In another embodiment, referring to FIG. 3, the patient support system PS may include a chair 100. The chair 100 comprises a seat 102, a back rest 104, a leg rest 106, arm rests 108, and wheels 110. The seat 102, the back rest 104, and the leg rest 106 cooperate to define the patient support surface 111. The chair 100 is constructed such that both height and tilt of seat 102 is adjustable. Furthermore, chair 100 is constructed such that back rest 104 is pivotable between a generally upright position and a rearwardly reclined position. Leg rest 106 is constructed such that it is able to be moved between a retracted position and an extended position. Arm rests 108 may be constructed such that a user can raise and lower their height relative to seat 102. Several manners in which chair 100 may be constructed in order to carry out these various motions of the seat 102, back rest 104, and leg rest 106 are contemplated. Of course, various configurations of the seat 102, back rest 104, leg rest 106, arm rests 108, and wheels 110 are contemplated.

Figure 4A:
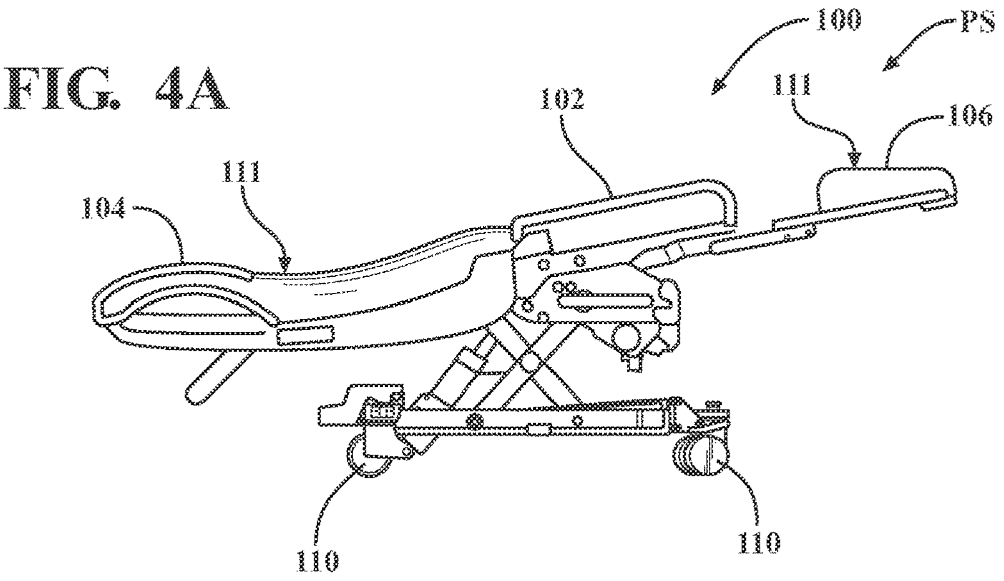
FIGS. 4A-4F are side views of various states of the coordinated motion device of FIG. 3.
Figure 4B:
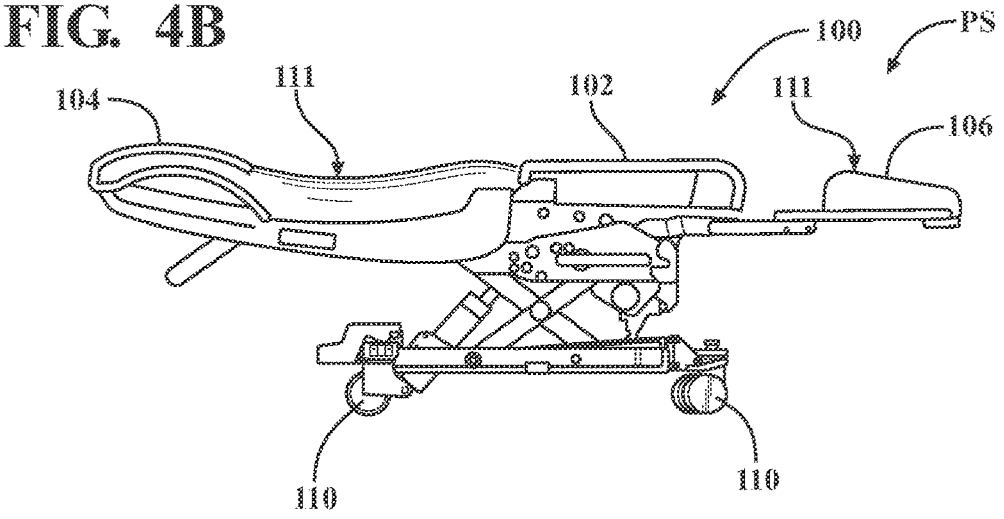
Figure 4C:
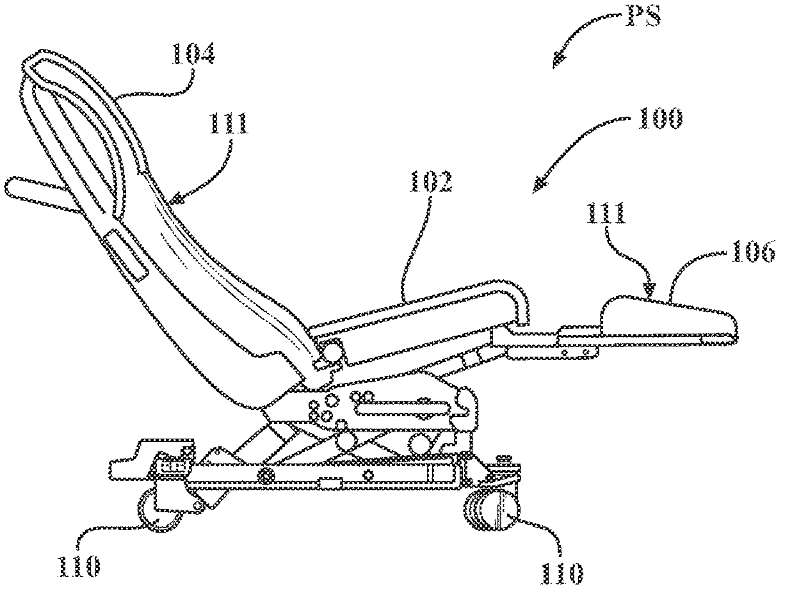
Figure 4D:
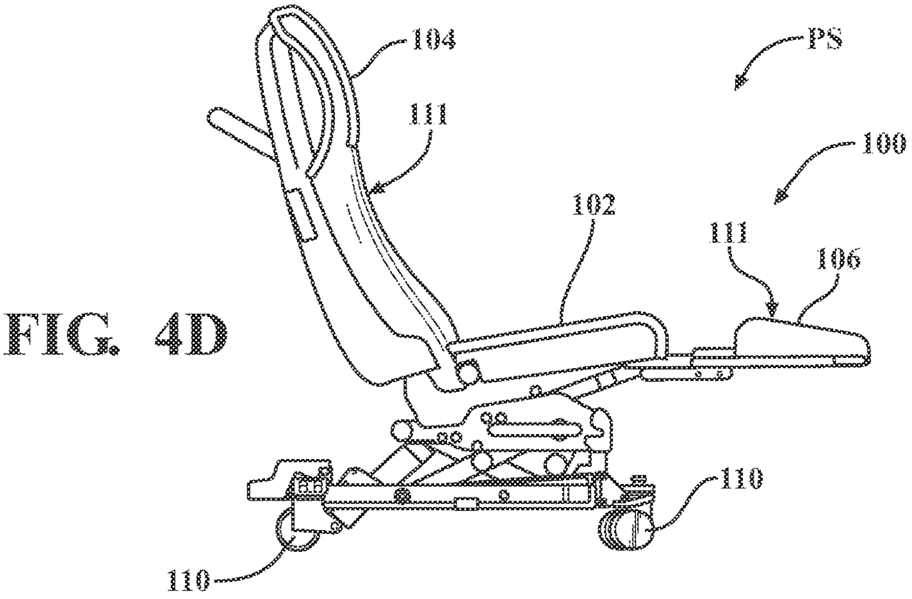
Figure 4E:
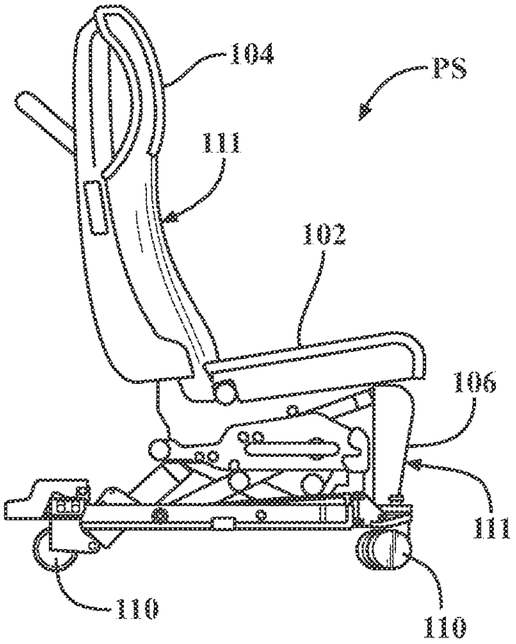
Figure 4F:
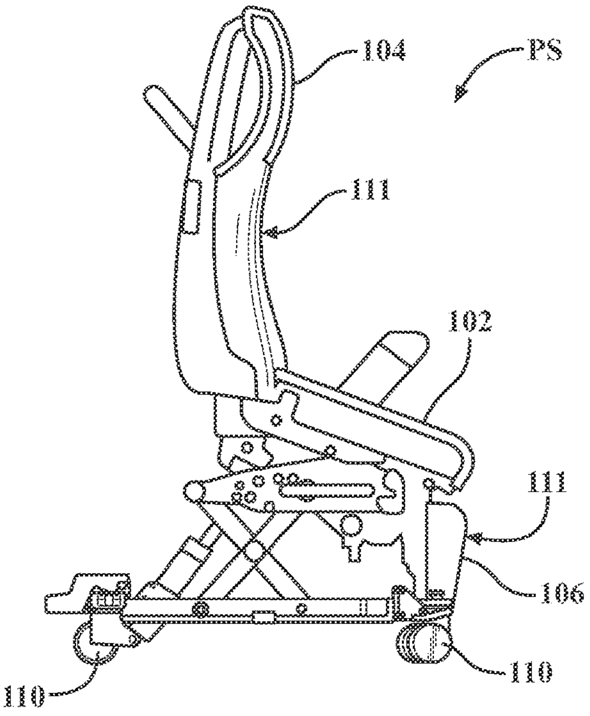

Referring to FIGS. 4A-4F, the chair 100 can be moved to six different configurations, including a Trendelenburg state (FIG. 4A), a flat state (FIG. 4B), a recline state (FIG. 4C), a second upright state (4D), a first upright state (FIG. 4E), and a stand state (FIG. 4F). In each of those states, the relative position of each of the seat 102, the back rest 104, and/or the leg rest 106 may be different relative to the floor.

Referring to FIG. 5, the patient support system PS may comprise one or more actuatable devices 200, each configured to perform one or more predetermined functions. Each of these actuatable devices 200 including one or more actuators 202. As such, each actuatable device 200 may comprise two or more actuators 202. In certain embodiments, the actuator 202 is a variable rate actuator 202 that is capable of operating at different rates of operation depending on the current and/or voltage applied to the actuator 202. In other words, the actuators 202 are of a type that their rate of operation can be controlled by changing a characteristic of the electrical signal provided to the actuator 202.

The type of actuator 202 that can be used is also not particularly limited. The actuator 202 should be broadly understood as a type of motor or device that is capable of moving or controlling a mechanism or a system. While the described embodiments are electric actuators and pumps, it should be understood that any type of actuator could also be used in certain applications. As such, actuator 202 refers to electrical, hydraulic, or pneumatic actuators. Thus, actuator 202 comprises actuators 202 that cause linear or rotational movement, that cause movement of a fluid, and the like. For example, the actuator 202 may comprise a rotary actuator, etc.

The types of actuatable devices 200 are not particularly limited, and may comprise any device or system that comprises one or more actuators 202. In certain embodiments, the actuatable device 200 is one that, when actuated, results in a change of position of one or more patient support surfaces 48, 52, 111 of the patient support system PS. This change in position of one or more patient support surfaces 48, 52, 111, when the patient occupies the patient support system PS, results in a change in the position of one or more portions of the patient's body. Thus, by controlling the rate of operation of the actuatable device 200, the rate that the patient changes positions can also be controlled.

More specifically, in situations where a patient occupies the patient support system PS, i.e., contacts one or more support surfaces 48, 52, 111, operation of each of the actuatable devices 200 results in movement of one or more portions of the patient P in one or more dimensions relative to a static surface, such as relative to a floor of a hospital. Examples of such movement include, but are not limited to: forward and reverse movement of the patient by virtue of movement of the patient support system PS along a floor; raising and lowering movement of the patient by virtue of movement of the patient support system PS upward and downwards relative to the floor; angular movement by virtue of changing the angle of at least a portion of the patient support system PS relative to a floor; rotation of the patient along a longitudinal axis of the patient support system PS (while the patient support apparatus 30 remains stationary relative to the floor); or various combinations of those types of movement.

Referring to FIG. 6, without being limited, the actuatable devices 200 that results in the change of the position of one or more patient support surfaces 48, 52, 111 of the patient support system PS may comprise a coordinated motion device 204, a patient raising device 206, a patient turning device 208, a patient centering device 210, a patient ingress/egress device 212, a lift device 214, a fowler adjustment device 216, a gatch adjustment device 218, and a transport device 220.

It is also contemplated that the actuatable device 200 may be of the type that does not result in a change of position, orientation, and/or elevation of the patient support surface 48, 52, 111. These 'non-position actuatable devices' may comprise, but are not limited to, patient comfort devices, such as entertainment devices, lighting devices, a temperature device, a humidity device, and aromatherapy devices, and patient therapy devices, such as vibration therapy devices, percussion therapy devices, compression therapy devices, patient warming devices, and electrical stimulation devices. The rate of operation of these non-position actuatable devices can also be controlled by changing the frequency, tempo, rate of temperature change, rate of humidity change, intensity of therapy, etc. of the devices.

A controller 222 is provided to control operation of the actuatable devices 204-220. The controller 222 comprises one or more microprocessors for processing instructions or for processing an algorithm stored in memory 224 to control operation of the actuatable devices 204-220. Additionally or alternatively, the controller 222 may comprise one or more microcontrollers, field programmable gate arrays, systems on a chip, discrete circuitry, and/or other suitable hardware, software, or firmware that is capable of carrying out the functions described herein. The controller 222 may be carried on-board the patient support system PS, or may be remotely located. In one embodiment, as shown in FIG. 1A, the controller 222 is mounted to the base 34 of the patient support apparatus 30. The controller 222 may comprise one or more subcontrollers configured to control all the actuatable devices 204-220 or one or more subcontrollers for each of the actuatable devices 204-220. Furthermore, two or more of the actuatable devices 204-220 may utilize the same controller 222, or sub-controller. Thus, multiple controllers 220 and/or or sub-controllers, may be configured to collectively control all of the actuatable devices 204-220.

Power to the actuatable devices 204-220 and/or the controller 222 may be provided by a power source 226, such as a battery power supply or an external power source. By virtue of the power source 226 being coupled to the actuatable devices 204-220, the actuator 202 is coupled to the power source 226. The power source 226 may provide direct current or alternating current.

The controller 222 controls the rate of operation of the actuator 202, and accordingly, changes the rate of operation of the actuatable devices 204-220 to which the actuators 202 are coupled. In configurations where the power source 226 is a direct current power source, the controller 222 may be coupled to the power source 226 and be configured to provide a pulse width modulation signal. The application of the pulse-width modulation signal to the power source 226 may be used to control the effective voltage supplied by the power source 226 to the actuators 202. In such a configuration, by controlling the effective voltage supplied to the actuators 202, the controller 222 may control the rate of operation of the actuators 202. The voltage and/or current may also be regulated using other available techniques, and the controller 222 may utilize these other techniques to control the rate of operation of the actuators 202.

In configurations where the power source 226 is an alternating current power source, the controller 222 may be coupled to the alternating current power source 226 and further configured to control the amplitude and/or frequency of the alternating current provided to the actuators 202. Thus, by controlling the amplitude and/or frequency of the alternating current supplied to the actuators 202, the controller 222 may control the rate of operation of the actuators 202.

For those actuators 202 that are coupled to actuatable devices 204-220 that, when actuated, cause a change in position or orientation of one or more patient support surfaces 48, 52, 111, the controller 222 may control the rate at which the patient support surfaces 48, 52, 111 are moved. When the patient is disposed on the patient support surfaces 48, 52, 111, the controller 222 may effectively control the rate at which the patient is moved by controlling the rate of operation of the associated actuator 202. Thus, the controller 222 may control the rate at which various portions of the patient's body move relative to a surface, such as a floor of the hospital. The rate of patient movement can refer to different types of movement including, but not limited to, the rate at which the patient is raised or lowered relative to the floor of the hospital; the rate at which the patient is angularly moved or tilted relative to the floor; the rate at which the patient is transported relative to the floor; or the rate at which the patient is rotated relative to a longitudinal axis of the patient support apparatus 30.

The controller 222 may utilize a look-up table or other suitable algorithm to determine the appropriate voltage or current to be supplied to each of the actuators 202 based on the desired rate at which the actuatable devices 204-220 should be adjusted. This information may be determined with mathematical modelling or using empirical data.

It should be appreciated that in situations where the actuators 202 are kinematically dissimilar from one another, the application of equal voltages to those actuators 202 would result in different types or magnitudes of motion. Therefore, the amount of voltage supplied to any of the actuators 202 generally differ even if the rate of operation for those actuators 202 is desired to be the same. The different voltages compensate for the kinematic dissimilarity of the actuators 202. For example, for linear actuators in actuatable devices 204-220 that have kinematically dissimilar configurations, for the same voltage, the pistons for those linear actuators 202 would necessarily extend (or retract) at different rates. Of course, it should be understood that the voltages supplied to various actuators 202 are described above as being different from each other "in general" in recognition of the reality that the voltages, although unequal and independent, may be momentarily numerically equal. Similarly, certain combinations of a prescribed change in elevation and a prescribed change in angular orientation may result in voltages that, although independent of each other, are, by chance, numerically equal for a sustained period of time. However in general most combinations of prescribed elevation change and prescribed angular orientation change will require numerically unequal voltages.

The controller 222 is coupled to the actuatable devices 204-220 in a manner that allows the controller 222 to control a rate of operation of the actuatable devices 204-220. The controller 222 may communicate with the actuatable devices 204-220 via wired or wireless connections. The controller 222 generates and transmits control signals to the actuatable devices 204-220, or components thereof, to cause the actuatable devices 204-220 to perform one of more of the desired functions. It should be appreciated that because the actuatable devices 204-220 comprise the actuators 202, the controller 222 essentially controls the actuators 202 included in each of the actuatable devices 204-220. Accordingly, it should be appreciated that any mention of the rate of operation of the actuators 202 and the actuatable devices 200 are interchangeable with one another, as the rate of operation of the actuator 202 is proportioned to the rate of operation for the associated actuatable device 200.

Furthermore, in some embodiments, the controller 222 may monitor a current state of the actuatable devices 204-220 and determine desired states in which the actuatable devices 204-220 should be placed. The state of the actuatable device 204-220 may be a position, a relative position, a pressure, an intensity, a frequency, an amplitude, a period, an angle, an energization status (e.g., on/off), or any other parameter of the actuatable device 204-220.

Referring again to FIG. 6, the patient support system PS may comprise user input devices 228. The caregiver, or other user, may actuate one of the user input devices 228, which transmits a corresponding user input signal to the controller 222, and the controller 222 controls operation of the actuatable devices 204-220 based on the user input signal. Operation of the actuatable devices 204-220 may continue until the caregiver discontinues actuation of the user input device 228, e.g., until the user input signal is terminated. In other words, depending on which user input device 228 is engaged, i.e., what user input signal is received by the controller 222, the controller 222 controls operation of one of the actuatable devices 204-220.

The user input devices 228 may comprise devices capable of being actuated by a user, such as the caregiver or the patient. The user input devices 228 may be configured to be actuated in a variety of different ways, including but not limited to, mechanical actuation (hand, foot, finger, etc.), hands-free actuation (voice, foot, etc.), and the like. Each user input device 228 may comprise a button, a gesture sensing device for monitoring motion of hands, feet, or other body parts of the caregiver (such as through a camera, e.g., an optical or thermal camera), a microphone for receiving voice activation commands, a foot pedal, and a sensor (e.g., a pressure sensor, an infrared sensor such as a light bar or light beam to sense a user's body part, ultrasonic sensor, etc.). Additionally, the buttons/pedals can be physical buttons/pedals or virtually implemented buttons/pedals such as through optical projection or on a touchscreen. The buttons/pedals may also be mechanically connected or drive-by-wire type buttons/pedals where a user applied force actuates a sensor, such as a switch or potentiometer.

Referring again to FIG. 1A, it should be appreciated that any combination of user input devices 228 may also be utilized for any of the actuatable devices 204-220. For example, user input devices 228 may be located on one of the side rails 54, 56, 58, 60, the headboard 62, the footboard 64, or other suitable locations. Further, the user input devices 228 may also be located on a portable electronic device (e.g., iWatch®, iPhone®, iPad®, or similar electronic devices), as shown in FIG. 1A.

Figure 7:
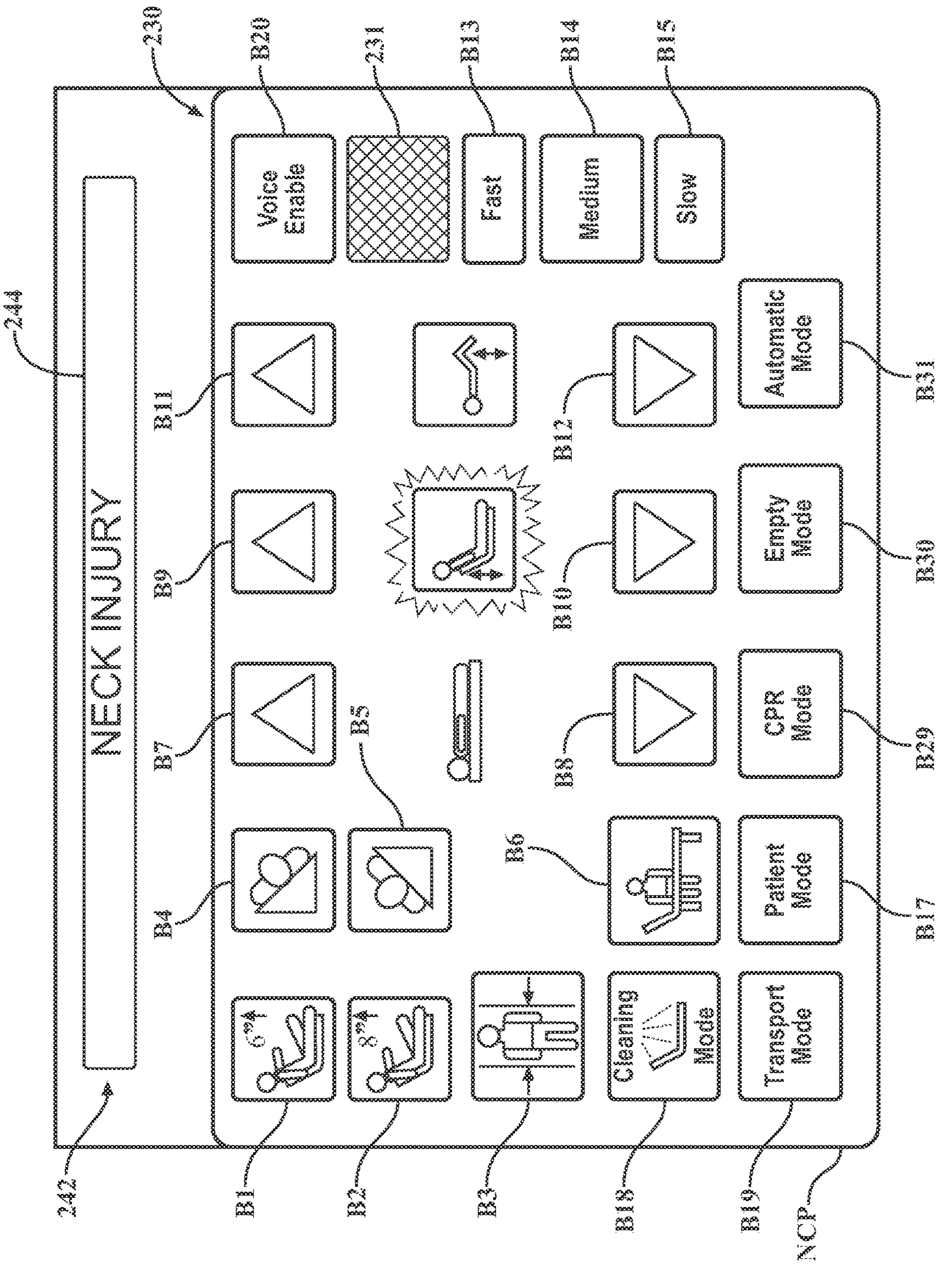
FIG. 7 is an illustration of a control panel for the patient support apparatus of FIGS. 1A and 1B.

In the embodiment shown in FIG. 1A and FIG. 7, the patient support apparatus 30 comprises a patient control panel PCP that comprises numerous user input devices 228 in the form of buttons B1-B12 and a nurse control panel NCP that comprises numerous input devices 228 in the form of buttons B1-B12. The buttons B1-B12 may be mechanical press buttons, virtual buttons on a touch screen, and the like. While buttons have been shown in the illustrated example, any of the aforementioned user input devices 228 may be used to control the actuatable devices 204-220. Furthermore, as should be appreciated, the patient support apparatus 30 may comprise any number of actuatable devices and the corresponding number of user input devices.

The nurse control panel NCP may be coupled to the patient support apparatus 30 such that the nurse control panel NCP is out of reach of the patient when the patient is disposed on the patient support surfaces 48, 52. On the other hand, the patient control panel PCP may be coupled to the patient support apparatus 30 such that the patient control panel PCP is within reach of the patient when the patient is disposed on the patient support surface 48, 52. Of course, the precise locations of the nurse control panel NCP and patient control panel PCP are not particularly limited.

In certain embodiments, the patient control panel PCP may comprise different user input devices 228 than the nurse control panel NCP. For example, in one exemplary embodiment, the nurse control panel NCP comprises rate selector buttons B13, B14, B15, whereas the patient control panel PCP does not comprise the rate selector buttons B13, B14, B15. In other words, the nurse control panel NCP may allow the caregiver to control more rates of operation for more actuatable devices 204-220 than the patient control panel PCP. For example, the patient control panel PCP may provide user input devices 228 that allows adjustment of the fowler adjustment device 216, but not the lift device 214. Alternatively, in certain embodiments, both the nurse control panel NCP and the patient control panel PCP both comprise the rate selector buttons B13, B14, B15.

Each of the buttons B1-B12 controls different predetermined functions of one or more of the actuatable devices 204-220. The button B1, upon actuation, causes the controller 222 to energize the patient raising device 206 to raise the patient six inches toward the head end of the patient support deck 38 (as may be needed when the patient is in a slouched position). The button B2, upon actuation, causes the controller 222 to energize the patient raising device 206 to raise the patient eight inches toward the head end of the patient support deck 38 (as may be needed when the patient is in a slouched position and six inches of raising is not enough). The button B3, upon actuation, causes the controller 222 to energize the patient centering device 210 to laterally urge the patient towards a longitudinal centerline of the mattress 50.

The buttons B4 and B5, upon actuation, cause the controller 222 to energize the patient turning device 208 to turn the patient on one side or another, respectively. The buttons B7 and B8 upon actuation, cause the controller 222 to energize the lift device 214 to lift or lower the patient support surfaces 48, 52 relative to the floor surface. The buttons B9, B10, upon actuation, cause the controller 222 to energize the fowler adjustment device 216 to adjust a position of the fowler section 40 of the patient support deck 38 relative to the floor surface. The buttons B11, B12, upon actuation, cause the controller 222 to energize the gatch adjustment device 218 to adjust the position of the foot section 46 and thigh section 44 relative to the floor. Referring now to FIG. 1A, the buttons, B16, coupled to caregiver interface 66, upon actuation, cause the controller 222 to energize the transport device 220 to move the patient support apparatus 30 across the floor.

In order for the caregiver to continue operating one of the actuatable devices 204-220 to perform the desired function using one of the buttons B1-B12 (or other user input devices 228), the caregiver may be required to continue actuating (e.g., continue depressing or continue touching) the buttons B1-B12 until the caregiver is satisfied with the adjustment that was made to the actuatable device 204-220. Other user input devices 228 can be continually actuated in other ways, depending on their mode of actuation. For instance, an infrared sensor that generates a light beam can be continually actuated by continually breaking the light beam. Similarly, a gesture sensing device can be continually actuated by continually sensing an actuating gesture.

In certain embodiments described herein, the user input devices 228 are configured to also enable continued operation (i.e., energization) of the actuatable devices 204-220, even after the caregiver ceases to actuate the user input device 228, e.g., after the caregiver ceases to depress or touch one of the buttons B1-B12, for a predetermined period of time, or until the desired adjustment is complete.

The patient support apparatus 30 may further comprise user input devices 228 associated with designation of one or more operational modes. These operational modes may designate a predetermined set of rates of operation for one or more of the actuatable devices 204-220. In the illustrated embodiment, button B17 designates a patient mode; B18 designates a cleaning mode; B19 designates a transport mode; B29 designates a CPR mode; B30 designates an empty mode; and B31 designates an automatic mode. Of course, the number of modes are not particularly limited, and the exemplary modes described above are provided merely for illustration.

The patient mode may include rates of operation for one or more actuatable devices 204-220 that are generally suitable for when a patient is disposed on the patient support surfaces 48, 52. The patient mode may be the default rate of operation for each of the actuatable devices 204-220. The cleaning mode may include rates of operation for one or more actuatable devices 204-220 that are optimal to quickly place the patient support surfaces 48, 52 in a position suitable for cleaning. The transport mode may include rates of operation for one or more actuatable devices 204-220 that are suitable for movement of the patient support system PS across long distances. The CPR mode corresponds to rates of operation that are suitable to quickly place the patient support apparatus 30 and the corresponding actuatable devices 204-220 in a condition that allows CPR resuscitation of the patient. The empty mode corresponds to rates of operation that are suitable when no patient is adjacent to the patient support surfaces 48, 52. The automatic mode corresponds to a configuration of the controller 222 where the controller 222 automatically determines a rate of operation suitable for the actuatable device 204-220 based on the patient condition 236 and/or the patient presence (as described below). Of course, it should be appreciated that various other operational modes may be utilized, and thus, additional user input devices 228 associated with these operational modes are contemplated.

In some embodiments, referring to FIG. 7, the user input devices 228 comprise a voice actuation interface 230 in communication with the controller 222. The voice actuation interface 230 may comprise a microphone 231 in communication with the controller 222 to receive voice activation commands from the caregiver. The voice activation commands may be associated with functions of the actuatable devices 204-220 in the same manner as buttons B1-B12. The controller 222 is configured to control the rate of operation of actuatable devices 204-220 based on the voice activation commands. For example, if the caregiver wishes to tilt the fowler section 40 upwards at a FAST rate of operation, the caregiver verbally commands "FOWLER UP", "FAST", in the vicinity of the voice activation interface 230. Similarly, if the caregiver wishes to stop the movement of the fowler section 40, the caregiver verbally commands "FOWLER", "STOP" Of course, the voice actuation interface 230 may be responsive to voice commands issued by the patient.

The controller 222 may be further configured to change the rate of operation of actuatable devices 204-220 already in motion based on the voice commands received from the voice actuation interface 230. For example, if the fowler adjustment device 216 is tilting upwards at the FAST rate of operation, and the caregiver verbally commands "SLOWER" in the vicinity of the voice actuation interface 230, the controller 222 decreases the rate of operation of the fowler adjustment device 216 relative to the current rate of operation. Similarly, if the fowler section 40 is tilting upwards at the SLOW rate of operation, and the caregiver verbally commands "FASTER" in the vicinity of the voice actuation interface 230, the controller 222 increases the rate of operation of the fowler adjustment device 216 relative to the current rate of operation. The measure at which the rate of operation is increased or decreased is not particularly limited, and may be a predetermined interval configured specifically for each of the actuatable devices 204-220, such as 1, 2, 3, or 4 centimeter/s second.

Of course, the controller 222 may also be responsive to voice commands that directly indicate the rate of operation desired for each actuatable device 204-220. Thus, in one example, the caregiver commands "LIFT DEVICE DOWN", "1 CENTIMETER PER SECOND", and the controller 222 controls the lift device 214 at the rate of operation of 1 centimeter per second. Of course, such direct rate of operation commands may be different depending on the type of motion produced by the actuatable device 204-220.

In the illustrated example, the voice actuation interface 230 comprises a voice activation enabling device B20 to enable usage of the voice actuation interface 230. The voice activation enabling device B20 is in communication with the controller 222. The voice activation enabling device B20 may comprise different types of user input devices 228 described above. The voice activation enabling device B20 may be located anywhere on the patient support apparatus 30 or remote from the patient support apparatus 30. However, the voice activation enabling device B20 could be mounted in other suitable locations, such as the base 34, the intermediate frame 36, the side rails 54, 56, 58, 60, the headboard 62, the footboard 64, or other suitable locations.

The voice activation enabling device B20 may also be located on a portable electronic device.

The voice activation enabling device B20 is actuated by the caregiver to enable voice activation commands to cause the controller 222 to transmit various output signals to the actuatable devices 204-220. In some embodiments, if the voice activation enabling device B20 is not actuated before voice activation commands are made, the controller 222 will not respond to the voice activation commands. Actuation of the voice activation enabling device B20 enables the voice activation interface 230 to provide the user input signal to the controller 222 to control one or more of the actuatable devices 204-220.

In certain embodiments, the patient support system PS further comprises an identification device 232 (See FIG. 1A). The identification device 232 is in communication with the controller 222. The identification device 232 is configured to identify a role of a person near the patient support system PS. The controller 222 may be configured to enable or disable certain user input devices 228 based on the role of the person identified by the identification device 232, such as buttons B17-B19 corresponding to the operational modes. In addition, the controller 222 may be configured to automatically select one of the operational modes based on the role of the person identified by the identification device 232. The identification device 232 may comprise an identifier, such as an RFID tag/badge, or other type of identifier capable of communication with the controller 222, such as an RFID reader on the patient support apparatus 30. In addition, the controller 222 may automatically enable the voice actuation interface 230 when the identification device 232 identifies that the role of the person adjacent to the patient support system PS should be authorized to issue voice commands to the patient support system PS.

Figure 8:
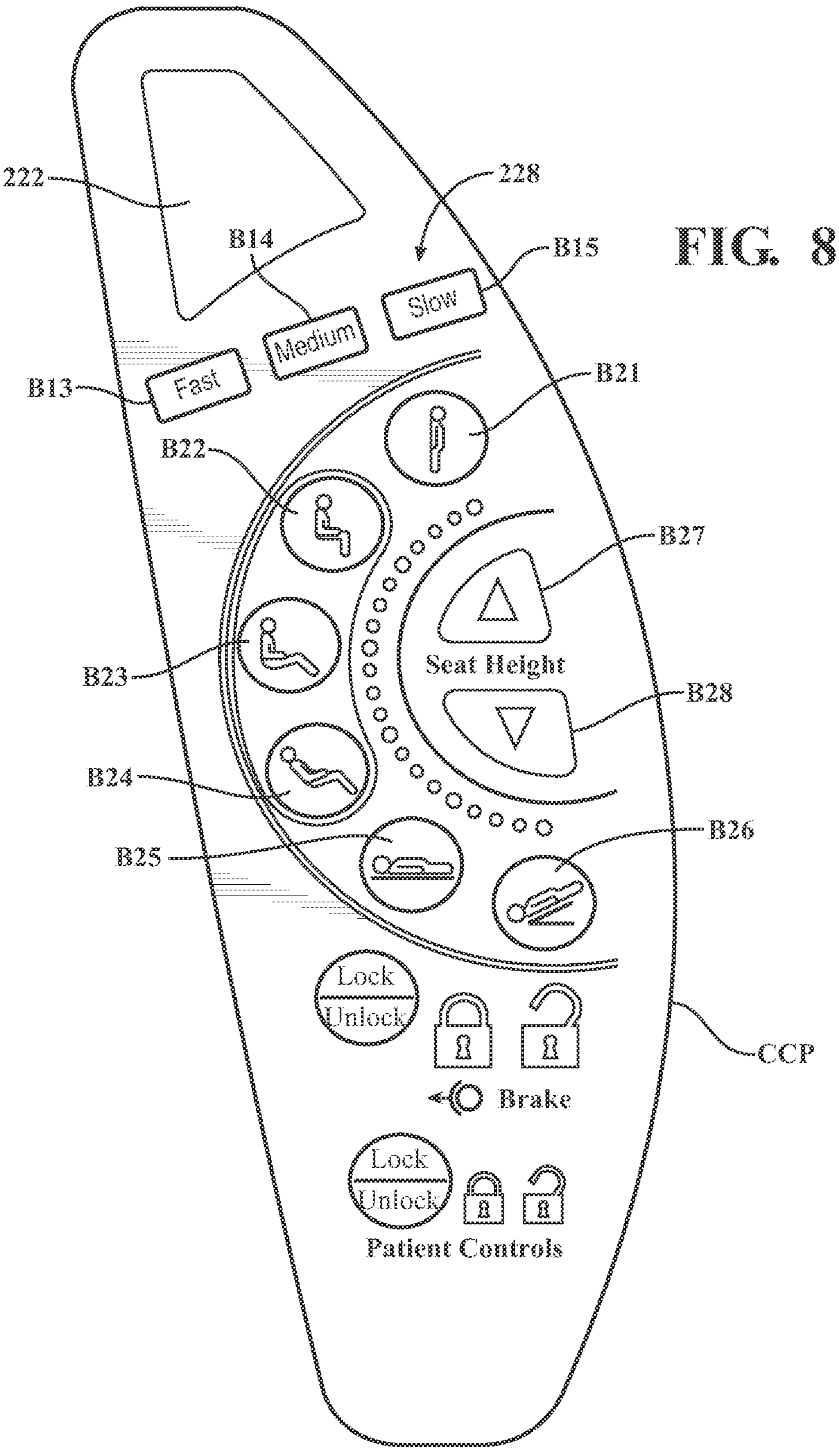
FIG. 8 is an illustration of a control panel for the coordinated motion device of FIG. 3.

With respect to the patient support system PS shown in FIG. 3, and with reference to FIG. 8, the chair 100 may comprise a chair control panel CCP. The chair control panel CCP comprises user input devices 228. For instance, the chair control panel CCP comprises button B21 corresponding to a standing state of the chair 100 (FIG. 4F); button B22 corresponding to a first upright state of the chair 100 (FIG. 4E); button B23 corresponding to a second upright state (FIG. 4D); button B24 corresponding to a recline state (FIG. 4C); button B25 corresponding to a flat state (FIG. 4B); button B26 corresponding to a Trendelenburg state (FIG. 4A); button B27 corresponding to a lift up control; and button B28 corresponding to a lift down control.

Referring to FIG. 6, in some embodiments, the controller 222 is configured to control the rate of operation of the actuators 202 based on a patient condition 234. The patient condition 234 may be determined by the controller 222 based on patient-related information. The patient-related information may be information obtained from an electronic medical record (EMR) 238, obtained from a sensing system 236, or obtained from a caregiver input using the user input device 228.

In embodiments where the patient-related information is obtained from the EMR 238, the EMR 238 may be copied and stored locally on the memory 224, or may stored on a network to which the controller 222 is coupled.

Figure 9:
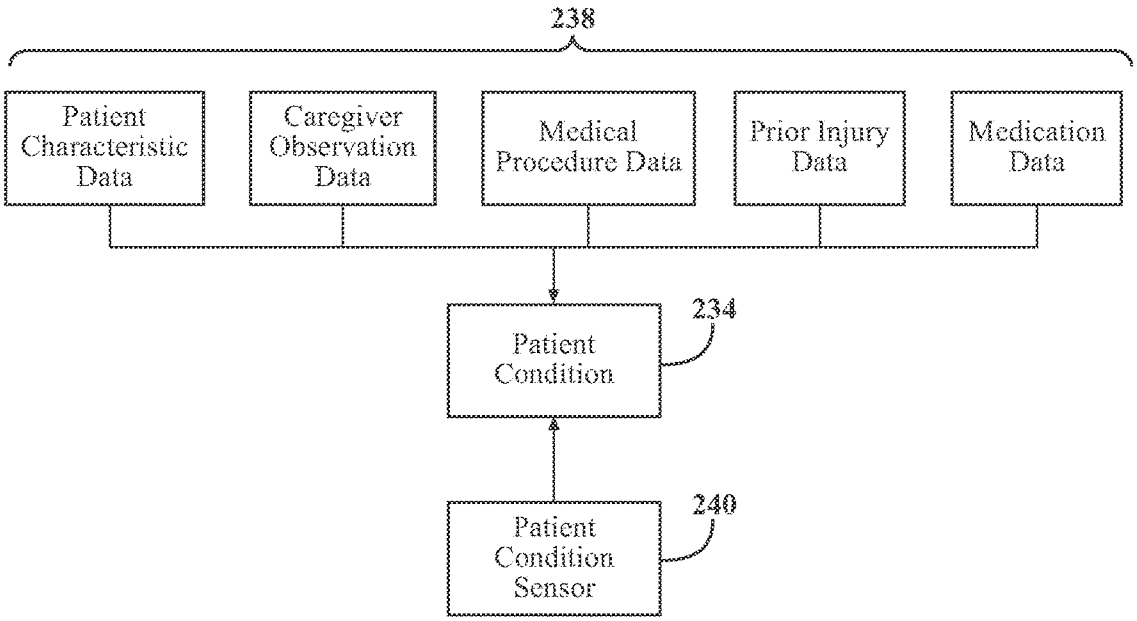
FIG. 9 is a schematic view of sources of patient-related information.

Referring to FIG. 9, the patient-related information may comprise medical procedure data, patient characteristic data, caregiver observation data, medication data, prior injury data, or combinations thereof. The medical procedure data may comprise a type of medical procedure, a duration since last medical procedure, a duration since admittance or combinations thereof. The patient characteristic data comprises height, width, pathology, race, age, weight, body mass index, activity level, movement history, fall risk (as based on a Morse Fall Scale Score) or combinations thereof. The caregiver observation data comprises psychological data, phobia data, pain level data, nausea level data, pain sensitivity data, or combinations thereof. In one specific embodiment, the patient-related information comprises a skin injury profile based on sensory perception, moisture, activity levels, nutrition, friction, shear, or combinations thereof. The patient condition may correspond to one or more diagnosis-related group (DRG). Of course, the type of patient-related information is not particularly limited, and may comprise any information about the patient that may affect their medical treatment or sensitivity to movement and motion, such as changes in position.

In certain embodiments, the patient condition 234 may be entered by the caregiver using the user input devices 228 described above, rather than being determined from the EMR 238. This allows the caregiver to include additional patient-related information at the time of controlling the patient support system PS. For example, the caregiver may enter the patient-related information using the voice actuation interface 230 described above by stating the command "PATIENT IS NAUSEOUS". The controller 222 may subsequently control the rate of operation of the actuator 202 in a manner that is suitable for a nauseous patient. Similarly, the caregiver may enter the patient-related information with a keyboard, touch-screen, or other suitable user-input device that is in communication with the controller 222. The type of patient-related information that can input with the user input device 228 is not particularly limited.

As described above, the patient condition 234 may be based on patient-related information obtained by a sensing system 236. The sensing system 236 is in communication with the controller 222, as shown in FIG. 6. Additionally, the sensing system 236 may be used by the controller 222 for various purposes.

Referring to FIG. 9, the sensing system 236 comprises one or more patient condition sensors 240. The patient condition sensor 240 is configured to sense a patient condition of the patient disposed on the patient support surfaces 48, 52, 111. The patient condition sensor 240 provides a patient condition input signal to the controller 222, which comprises patient-related information. In one example, the patient condition sensor 240 comprises a patient physiological sensor. The type of patient physiological sensor is not particularly limited, and may comprise a heart rate sensor (such as an electrocardiography sensor), a patient temperature sensor, a load cell, a blood pressure sensor, a patient shear sensor, a camera (optical or thermal), a patient moisture sensor, a neurological sensor (such as an electroencephalography sensor), a breathing monitor, a patient expression sensor, an acoustic sensor, or combinations thereof.

The patient physiological sensor may be used to determine a variety of physiological conditions such as a patient's heart rate, breathing data, patient's temperature, blood pressure, whether the patient is sleeping, the patient is coughing, etc. The controller 222 may utilize this sensed physiological data instead or, or in addition to, the patient condition 234 obtained from the EMR 238 or the patient condition 234 inputted by the caregiver with the user input devices 228.

The one or more patient condition sensors 240, especially the patient physiological sensors, can be coupled directly to various parts of the patient's body including, but not limited to, the patient's head, chest, arm, wrist, leg, stomach, foot, neck, back, and other suitable locations for sensing of the patient's physiological conditions. As shown in FIG. 1A, the patient condition sensor 240 is a pulse oximeter coupled to the patient's finger. Alternatively, the patient condition sensor 240 may be located on or in the base 34, the intermediate frame 36, the patient support deck 38, the mattress 50, the side rails 54, 56, 58, 60, the headboard 62, the footboard 64, the back rest 104, the leg rest 106, the seat 102, or the arm rests 108 or other suitable locations as described further below, so long as the patient condition sensor 240 can determine the patient's physiological condition.

In embodiments where the patient condition sensor 240 comprises the acoustic sensor, the controller 222 may be configured to recognize certain sounds as corresponding to certain patient-related information. Thus, if the patient grunts, cries, groans, or otherwise audibly expresses themselves, the controller 222, with the acoustic sensor, can recognize these sounds, or pattern of sounds, as indicating the patient condition 234. In one example, if the patient is crying, the acoustic sensor can send a signal to the controller 222 indicative of the crying, and the controller 222 can recognize the input signal as indicative that the patient is crying. The controller 222 can correlate certain types of audible sounds as indicative of the pain level of the patient, and subsequently control the rate of operation for the actuatable devices 204-220 based on that pain level. Thus, if the patient is crying, the controller 222 may control the actuatable devices 204-220 with the SLOW rate of operation. Of course, the types of sounds recognizable by the controller 222 is not particularly limited. Of course, the controller 222 recognize patient-related information based on the decibels of the sounds made by the patient. Furthermore, it is contemplated that the controller 222 may control the rate of operation of the actuatable devices 204-220 based on the pain level in combination with other types of patient-related information, such as the heart rate.

In embodiments where patient condition sensor 240 comprises a force sensor, the force sensor may be coupled to one or more portions of the patient support apparatus 30, such as top of the side rails 54 and 56. More specifically, the force sensor may be coupled to one or more grips (not shown) provided by the side rails 54, 56, 58, 60. In situations where the patient grasps one or more of the grips provided by the side rails 54, 56, 58, 60, and thus engages the force sensor coupled to the grips, the controller 222 can recognize the force applied to the grips as indicating the patient condition 234. The controller 222 can correlate certain forces applied to the grips of the side rails 54, 56, 58, 60 as indicative of the pain level of the patient, and subsequently control the rate of operation for the actuatable devices 204-220 based on that pain level. In such an embodiment, the controller 222 may utilize a look-up table to compare expected forces with actual forces to determine what actual forces correspond to various patient conditions 234. Furthermore, it is contemplated that the controller 222 may control the rate of operation of the actuatable devices 204-220 based on the pain level in combination with other types of patient-related information, such as the heart rate. Of course, the location and position of the force sensors are not particularly limited, and may be mounted to any portion of the patient support apparatus 30 that a patient would be expected to apply a force when stressed or in pain. In one exemplary configuration, if the patient is exhibiting a first force on the grip of the side rail 54 that is indicative that the patient is highly stressed, the controller 222 may automatically select a rate of operation for the actuatable devices 204-220 that is suitable to move a patient that is highly-stressed.

In certain embodiments, the sensing system 236 may comprise a patient presence sensor 241. The patient presence sensor 241 may be configured to determine whether the patient is disposed adjacent to one of the patient support surfaces 48, 52, 111, and provide a patient presence input signal to the controller 222.

The type of patient presence sensor 241 is not particularly limited and may comprise a force sensor (such as a load cell), a weight sensor, an optical sensor, an electromagnetic sensor, an accelerometer, motion sensors, infrared sensors, membrane switches, cameras (optical or thermal), a potentiometer, an ultrasonic sensor, or combinations thereof.

The patient presence sensor 241 may further be configured to determine a position of various portions of the patient as it relates to current positions of the patient relative to various portions of the patient support system PS (e.g., the patient is slouched, the patient is off center, the patient is lying supine, the patient is getting ready to exit, the patient is sitting up, etc.).

Referring to FIG. 1A, the patient presence sensor 241 is shown coupled to each of the side rails 54, 56, 58, 60, and footboard 64. The patient presence sensor 241 may monitor thresholds or discrete point movements. The patient presence sensors 241 can be located anywhere on the patient support system PS or remote from the patient support system PS. Referring to FIG. 3, the patient presence sensor 241 is shown coupled to the back rest 104, the seat 102 and the leg rest 106. However, the patient presence sensor 241 may be located in any suitable location, in or on the base 34, the intermediate frame 36, the patient support deck 38, the mattress 50, the side rails 54, 56, 58, 60, the headboard 62, the footboard 64, the back rest 104, the leg rest 106, the seat 102, the arm rests 108, or other suitable locations.

In one embodiment, as shown in FIG. 3, the patient presence sensor 241 comprises load cells to measure whether a load is applied to the patient support surface 111. Alternatively, with reference to FIG. 1A, the patient presence sensor 241 comprises an infrared sensor configured to detect whether the patient is adjacent to the patient support surfaces 48, 52, without the patient actually being in contact with that support surface 48, 52. This non-contact patient presence sensing modality can alternatively utilize optical sensors, such as a light curtain, to detect whether the patient is positioned adjacent to the support surface 48, 52. Of course, it is also contemplated to determine the presence of the patient adjacent to, or in contact with, the patient support surfaces 48, 52, 111 with alternative devices.

The sensing system 236 may further be configured to sense a current position of the actuator 202 and/or state of the actuatable device 204-220. For example, in embodiments where the actuator 202 is a linear actuator 202, the sensing system 236 may determine whether the actuator 202 is fully-extended, partially-extended, or the precise extent of extension. The position of the actuator 202 can be determined with an encoder, or similar device. The controller 222 may utilize these position input signals from the sensing system 236 to determine a pattern of movement of the patient support system PS. The pattern of movement of the patient support system PS may include a history of movement of the actuators 202 between various positions, or movement of the actuatable device 200 between one or more states.

Additionally, in some embodiments, the sensing system 236 may comprise an ambient condition sensor, such as a humidity sensor, an ambient temperature sensor, or an acoustic sensor, in communication with the controller 222. Still, other types of sensors are also contemplated for use with sensing system 236.

Patient-related information from the sensing system 236 can be stored in the memory 224 of the controller 222 and can be used to provide a history log or charts for the caregiver, as well as activate alarms or other indicators to the caregiver if needed.

Referring to FIG. 6, the controller 222 may be coupled to an indicator device 242. The indicator device 242 may be configured to indicate to the caregiver certain aspects of the patient condition 234 obtained from the patient-related information. The indicator device 242 comprises at least one of a display, a speaker, and a light emitting device. In some cases, the indicator system 242 comprises multiple indicators. For instance, the indicator device 242 shown in FIG. 7 comprises a display 244. The display 244 may be an LCD, LED, or other type of display. Of course, the indicator device 242 may comprise a light source for indicating patient-related information to the caregiver.

The indicator device 242, as shown in FIG. 6, may be in communication with the controller 222 to indicate the patient condition 234 to the caregiver. Alternatively, the controller 222 may be configured to present information to the caregiver using the indicator device 242 when the controller 222 determines that the current patient condition 234 requires additional operation of one of the actuatable devices 204-220. Additionally, the indicator device 242 can be configured to communicate suggestions to the caregivers about additional operation of the actuatable devices 204-220 or provide reminders to the caregivers about the proper rate of operation for one or more of the actuatable devices 200. For instance, graphic or text messages may be presented to the caregiver with the indicator device 242 that the patient is sensitive to changes in position.

The indicator device 242 can be located anywhere on the patient support system PS that is suitable to indicate information to the caregiver. The indicator device 242 may also be located remote from the patient support system PS, such as on a portable electronic device, nurse's station, or other location. In FIG. 1A, the display 244 shows that the current patient condition 234 is "neck injury", e.g., the patient condition 234 indicates that the patient was admitted for a neck injury.

In a first embodiment, the controller 222 controls the rate of operation of the actuators 202 based on the user input signal received. The controller 222 may determine the user-selected rate of operation based on the user input signal provided to the controller 222. Thus, through actuation of the rate selector buttons B13-B15 (or other suitable user input device 228), the controller 222 determines that the user desires to control the rate of operation of the actuator 202 and, subsequently, the controller 222 transmits the appropriate output signal to the actuators 202 to the one or more actuatable devices 204-220. The user-selected rate of operation should be understood to refer to any rate of operation that was selected by the user of the patient support system PS.

The user input device 228 may allow the caregiver to directly select the rate of operation for the actuatable device 204-220 in various manners, and based on the corresponding user input signal, the controller 222 can control the actuatable devices 200 based on the user-selected rate of operation. In one configuration, the controller 222 may determine a user-selected rate of operation based on actuation pattern of the user input device 228. For example, two rapid engagements of button B10 provides a user input signal that the controller 222 recognizes as indicating that a FAST rate of operation is desired by the caregiver for the fowler adjustment device 216. The controller 222 subsequently transmits an output signal to the fowler adjustment device 216 that causes the fowler section 40 to move towards the intermediate frame 36 at the FAST rate of operation. As an additional example, a single engagement of button B1 provides a user input signal to the controller 222 that the controller 222 recognizes as indicating that a SLOW rate of operation is desired by the caregiver for the patient raising device 206, and the controller 222 subsequently transmits an output signal to the patient raising device 206 that causes the patient raising device 206 to operate at the SLOW rate of operation.

Alternatively, the user input device 228 may provide for direct selection of the rate of operation by the caregiver, with a user input device 228 that can be adjusted along a continuous spectrum, such as a rotatable or slidable control knob or pressure sensor. Thus, if the user engages the pressure sensor with a certain force, the controller 222 can recognize the corresponding user input signal as indicating that the user desires a FAST rate of operation. Along the same lines, if the user engages the pressure sensor with a second force, smaller than the first force, the controller 222 can recognize the corresponding user input signal as indicating that the user desires a SLOW rate of operation.

In summary, it is contemplated that the patient support system PS may comprise user input devices 228 capable of selecting a nearly infinite number of rates of operation, or a certain number of predefined rates of operation. While the FAST, MEDIUM, and SLOW rates of operation are described throughout this disclosure, it should be appreciated that the controller 222 may control the rate of operation of the actuatable devices 204-220 and the actuators 202 at an infinite number of different rates of operation. Of course, additional predetermined rates of operation other than the FAST, MEDIUM, and SLOW predetermined rates of operation are also contemplated. In certain embodiments, once the rate selector buttons B13, B14, B15 are depressed, all actuations of any user input device 228 with a certain period of time are controlled at the user-selected rate of operation. Alternatively, a single press of the rate selector buttons B13, B14, B15 may only control the rate of operation for the next user input device 228 that is actuated.

In one embodiment, the controller 222 may be configured to determine the source of the user input signal received, and control the rate of operation of actuatable devices 204-220 based on that source. For example, the controller 222 may determine whether the user input signal was derived from actuation of the user input device 228 on the nurse control panel NCP or the patient control panel PCP, and control the rate of operation of the actuatable device 204-220 based on the source of that user input signal. For example, if the controller 222 determines that the source of the user input signal is the nurse control panel NCP, the controller 222 may enable the full range of the rates of operation for all of the actuatable devices 204-220. However, if the controller 222 determines that the source of the user input signal is the patient control panel PCP, the controller 222 may enable less than the full range of rates of operation for less than all of the actuatable devices 204-220. For instance, if the controller 222 determines that the source of the user input signal is the patient control panel PCP and the user input signal indicates that the rate of operation of the lift device 214 is desired to be controlled such as by pressing button B7 twice, the controller 222 may disregard the user input signal and not allow adjustment of the rate of operation for the lift device 214.

It is also contemplated that voice activation commands can directly control the rate of operation of the actuatable devices 204-220 by using the voice actuation interface 230. For example, if the caregiver wants to tilt the fowler section 40 upwards at the SLOW rate of operation, the user verbally commands "FOWLER UP", "SLOW" in the vicinity of the voice activation interface 230. In response to receiving and recognizing these voice activation commands, the controller 222 transmits an output signal to the fowler adjustment device 216 which causes the fowler adjustment device 216 to tilt the patient upward at the SLOW rate of operation.

In some embodiments, the controller 222 may be configured to perform an authentication protocol before transmitting an output signal to the actuatable devices 204-220 based on the user input signal received from the one or more user input devices 228. The authentication protocol may be based on the role of the person identified with the identification device 232. Thus, once the controller 222 receives the user input signal from the user input device 228, the controller 222 may query the identification device 232 to confirm that person(s) who are adjacent to the patient support system PS are entitled to control the rate of operation of the actuatable devices 204-220 with the user-selected rate of operation. This can be accomplished by reading an identifier device 232 and comparing the identifier to a look-up table in the memory 224 that correlates the identifier to various roles.

For example, the controller 222 may be configured to only allow certain roles of person to select certain rates of operations for certain actuatable devices 204-220. Thus, the controller 222 may establish certain permission thresholds for certain roles. The 'NURSE' role may be entitled to adjust the rate of operation for all actuatable devices 204-220 across the full range of available rates of operation. In contrast, the 'ASSISTANT' role may only be entitled to adjust the rate of operation for less than all of the actuatable devices 204-220 across less than the full range of available rates of operation. For example, persons associated with the 'ASSISTANT' role may only be entitled to adjust the rate of operation of the lift device 214 with the SLOW rate of operation. Of course, an infinite number of permission thresholds can be set for an infinite number of roles.

Furthermore, the controller 222 may be configured to query the identification device 232 when the controller 222 receives a user input signal based on the actuation of the buttons B17, B18, B19 associated with one or more preset operational modes, such as the PATIENT mode, the CLEANING mode, the TRANSPORT mode, or the CPR mode. The controller 222 may confirm that the role of the person identified by the identification device 232 corresponds to the operational mode selected by the user. If the controller 222 determines that the role of the person that is adjacent to the patient support system PS is permitted to enable the operational mode that is selected, the controller 222 may enable the operational mode selected, and the preset rates of operation that accompany it. However, if the controller 222 determines that the role of the person that is adjacent to the patient support system PS is not permitted to enable the operational mode that is selected by the user, the controller 222 may not enable the selected operational mode. As such, in this embodiment, the controller 222 prevents selection of the one or more operational modes by persons who are not permitted to utilize the one or more operational modes. For example, if a user actuates button B18 to designate the CLEANING operational mode and the identification device 232 determines that user is associated with the NURSE role, the controller 222 may not enable the CLEANING operational mode, but may allow the controller 222 to enter the PATIENT mode. Similarly, the controller 222 may only enable the CPR operational mode for users associated with the NURSE role.

The memory 224 may store the permission thresholds for the operational modes. Each operational mode may correspond to a preset rate of operation for at least one actuatable device 204-220. The controller 222 is configured to determine a desired rate of operation based on the selected operational mode. For example, the transport device 220 may have a preset rate of operation of FAST for the TRANSPORT mode. On the other hand, the transport device 220 may have a preset rate of operation of SLOW for the PATIENT mode. The FAST rate of operation may correspond to a rate of operation of the transport device 220 ranging from 5 to 15 mph, whereas the SLOW rate of operation of the transport device 220 may range from 1 to 5 mph. Of course, the transport device 220 may be controlled to perform at other rates of operation other than the ranges contemplated above for the TRANSPORT mode and the PATIENT mode. Generally, the FAST rate of operation for the transport device 220 may allow quick movements of the patient support apparatus 30 along the floor.

As another example, the CPR mode may have preset rate of operation of FAST for the lift device 220, the fowler adjustment device 216, and the gatch adjustment device 218. Furthermore, the empty mode may have a preset rate of operation of FAST for more than one actuatable devices 204-220, or all of the actuatable devices 204-220.

Each operational mode may be associated with a particular algorithm that yields a suitable rate of operation based on the patient-related information. In one embodiment, the algorithm may be based on the fall risk (such as the Morse Fall Scale Score), the weight of the patient, the age of the patient, the pain level of the patient, or combinations thereof. Of course, different types of patient-related information may be weighted differently in the algorithm to determine the suitable rate of operation. Furthermore, any suitable algorithm may be utilized for each operational mode to ensure that the rate of operation for each of the actuatable devices 204-220 is suitable for the patient condition and/or patient presence.

In other embodiments, the controller 222 determines the desired rate of operation based on a combination of the user input signal and the patient presence input signal. This allows the controller 222 to verify whether the patient is disposed adjacent to one or more of the patient support surfaces 48, 52, 111 before controlling the actuatable devices 204-220 with the user-selected rate of operation. If the patient is disposed adjacent to the one of more patient support surfaces 48, 52, 111 as determined by the patient presence sensor 241, the controller 222 may not allow the actuatable devices 204-220 to be controlled at a rate of operation above a predetermined rate of operation, such as above the MEDIUM or SLOW rates of operation. Similarly, if the patient is not disposed adjacent to the one or more patient support surfaces 48, 52, 111 as determined by the patient presence sensor 241, the controller 222 may enable all rates of operation for one or more of the actuatable devices 204-220. For example, if the caregiver actuates a user input device 228 associated with the transport device 220 at a FAST rate of operation and the controller 222 determines that the patient is adjacent to the patient support surface 48, 52, 111 based on the patient presence input signal, the controller 222 may not send an output signal to the transport device 220 that would cause the transport device 220 to operate at the FAST rate of operation. Instead, the controller 222 may cause the indicator device 242 to notify a caregiver that the user-selected rate of operation is not appropriate. Alternatively, the controller 222 may automatically control the transport device 220 with a rate of operation that is suitable for when the patient is present, such as the SLOW rate of operation.

By way of further example, once the patient has exited the patient support system PS, the caregiver or other person may wish to lower the patient support surface 48, 52, 111 relative to the floor. Accordingly, the caregiver selects the buttons B8 or B28 to lower the patient support surface 48, 52, 111 and the controller 222 starts operation of the lift device 214. Normally, the lift device 214 operates at a single rate of operation despite whether the patient is positioned on the patient support surface 48, 52, 111 or not. However, in the disclosed embodiment, the controller 222 may determine that no patient is adjacent to the patient support surface 48, 52, 111 based on the patient presence input signal, and may automatically control the rate of operation of the lift device 214 with an increased rate of operation, such as the FAST rate of operation. The FAST rate of operation may be desirable in order to increase the efficiency of certain operations, such as cleaning operations. The SLOW rate of operation, in these circumstances, may require the caregiver to wait several seconds until the lift device 214 lowers the patient support surface 48, 52, 111 to a sufficient height to allow the cleaning operations. This creates unnecessary delay that compromises hospital efficiency.

Additionally, in embodiments where various operational modes are selectable, the controller 222 may allow or prevent the selection of certain operational modes depending on the patient presence input signal. More particularly, the controller 222 may prevent actuation of the cleaning mode and/or the transport mode if the patient presence sensor 241 determines that the patient is adjacent to the patient support surface 48, 52, 111. For example, if the controller 222 determines that the patient is adjacent to the patient support surface 48, 52, 111, the controller 222 may not allow operation of the patient support system PS in the TRANSPORT mode or CLEANING mode. Alternatively, if the controller 222 determines that the patient is not adjacent to the patient support surfaces 48, 52, 111, the controller 222 may enable all of the operational modes.

The controller 222 may be further configured to control the rate of operation of the actuatable devices 204-220 based on the patient condition 234. The controller 222 may utilize a look-up table to control the rate of operation based on the patient condition 234. For example, the controller 222 may query a look-up table that correlates pre-loaded patient conditions to various rates of operation to determine the desired rate of operation based on the patient condition 234. Alternatively, the controller 222 may utilize an algorithm to determine the desired rate of operation for the actuator 202 and/or the actuatable device 204-220 based on the patient condition 234. As described above, the patient condition 234 can be obtained from the patient-related information that is present in the EMR 238, entered by the caregiver with the user input device 228, or sensed by the patient condition sensors 240. By depressing the button B31, corresponding to the automatic mode, the controller 222 may thereafter operate to control the rate of operation of the actuatable devices 204-220 based on the patient condition 234. Of course, in other embodiments, the user may deactivate the automatic mode such that the controller 222 does not control the rate of operation for the actuatable devices 204-220 based on the patient condition, but solely controls the rate of operation for the actuatable devices 204-220 based on user input signals received from various user input devices 228.

In one configuration, the controller 222 receives a user input signal from the user input device 228 that indicates that the user desires to change the configuration of one of the actuatable devices 204-220. The controller 222, based on the patient condition 234, determines the desired rate of operation for the actuatable device 204-220 and transmits an output signal to that actuatable device 204-220 to control the actuatable device 204-220 at the desired rate of operation. Thus, in such an embodiment, the user does not need to select a user-selected rate of operation, as the controller 222 is configured to automatically determine the desired rate of operation based on the patient condition 234. Alternatively, based on the patient condition 234, the controller 222 may be configured to cause the indicator device 242 to display a rate of operation for the actuatable device 204-220 that would be suitable. At that point, the user may manually select the rate of operation based on the recommendation communicated by the indicator system 242.

The controller 222 may control the rate of operation for the actuator 202 and/or actuatable devices 204-220 based on the combination of the user input signal and the patient condition 234. Thus, the controller 222, upon receiving the user input signal from one or more user input devices 228, may query the patient condition 234 in order to determine whether the user-selected rate of operation is suitable in light of the patient condition 234. If the controller 222 determines that the user-selected rate of operation is not suitable based on the patient condition 234, the controller 222 may automatically send an output signal that commands the actuator 202 of the actuatable device 204-220 to perform at a rate of operation that is more suitable for the patient condition 234 than the user-selected rate of operation. Alternatively, the controller 222 may simply prevent operation of the actuator 202 if the user-selected rate of operation is not suitable based on the patient condition 234. Furthermore, if the controller 222 determines that the user-selected rate of operation is unsuitable for the patient condition 234, the controller 222 may control the indicator device 242 to alert the caregiver that the user-selected rate of operation is not suitable. Similarly, the indicator device 242 may cooperate with the controller 222 to display a suitable rate of operation that is suitable for the patient condition 234.

Figure 10:
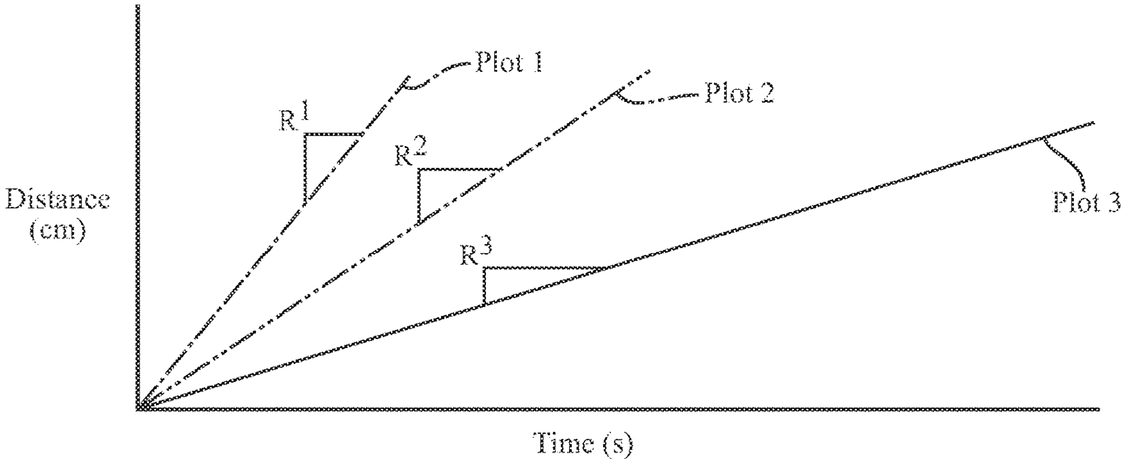
FIG. 10 is a chart showing different rates of operation for a lift device based on different patient conditions.

Referring the chart of FIG. 10, in one example, the actuatable device 200 is the lift device 214. PLOT 1 shows a first rate of operation R1 of the lift device 214 suitable for a patient that does not require extraordinary care, a normal patient condition. PLOT 2 shows the second rate of operation R2 for the lift device 214 suitable for a patient that has a moderate sensitivity to movement due to a history of skin lesions. PLOT 3 shows a third rate of operation R3 for the lift device 214 suitable for a patient that has high sensitivity to movement based on extensive burns and recent skin grafts. The controller 222 is configured to control the lift device 214 with rates R1, R2, and R3 depending on the patient condition.

Referring to FIG. 7, in one example, the controller 222 may determine that the caregiver wishes to raise the patient from a flat position to a position where the patient's head is raised as indicated by the caregiver actuating the button B9. Actuation of the button B9 transmits the user input signal to the controller 222. The controller 222 may respond by selecting or initiating operation of the fowler adjustment device 216 (described in detail below). During normal operation, the fowler adjustment device 216 would raise the fowler section 40 at a single constant rate, regardless of the patient condition 234 of the patient positioned on the patient support surface 48, 52. The fowler adjustment device 216 would continue changing its configuration until the caregiver discontinues actuation of the button B9. However, based on the patient condition 234, in response to depressing the button B9, the controller 222 may change the rate of operation of the fowler adjustment device 216 such that rate of operation for the fowler adjustment device 216 is appropriate for the patient condition 234 of the patient that is disposed on the patient support surface 48, 52.

In the illustrated embodiment, the patient has a neck injury, and thus the patient condition 234 reflects this neck injury. The caregiver selects button B9 associated with changing the angle of the fowler section 40, and depresses button B13, simultaneously or subsequently. Based on the patient condition 234, i.e., the neck injury, the controller 222 determines that, for the fowler adjustment device 216, the rate of operation should be SLOW. Because the user-selected rate of operation is faster than the desired rate operation determined based on the patient condition 234, the controller 222 determines that the user-selected FAST rate of operation is not suitable. As such, the controller 222 controls the rate of operation such that the fowler adjustment device 216 instead operates at the SLOW rate operation. The SLOW rate of operation for the fowler adjustment device 216 minimizes the pain and/or discomfort experienced by the patient that may otherwise result from fast rates of operation of the fowler adjustment device 216 which may disrupt the neck injury of the patient.

The controller 222 may determine the desired rate of operation based on the user-selected rate of operation and based on the patient condition 234 before transmitting the output signal to the fowler adjustment device 216 to control the rate of operation for the fowler adjustment device 216. If the controller 222 determines that the user-selected rate of operation is suitable based on the patient condition 234, the controller 222 transmits an output signal to the fowler adjustment device 216 which causes the fowler adjustment device 216 to operate at the user-selected rate of operation.

The controller 222 may be configured to prevent actuation of certain actuatable devices 204-220 and/or certain rates of operation based on the patient condition 234. For example, with reference to FIG. 1A, if the patient condition 234 indicates that the patient had neck surgery, the controller 222 may prevent the actuation of the fowler adjustment device 216 altogether. That is, the controller 222 may ignore user input signals associated with control of the fowler adjustment device 216. The type of "lock-out" is not particularly limited, and the controller 222 may prevent the patient support system PS from entering a Trendelenburg or reverse Trendelenburg orientation; a height of the patient support deck 38 may be prevented from being adjusted outside of an acceptable range; the patient support surfaces 48, 52, 111 may be prevented from entering an unacceptable orientation; and other suitable lock-outs are contemplated.

In some embodiments, if two or more user input devices 228 are actuated simultaneously to generate two or more input signals, the controller 222 may automatically control the rate of operation of two actuatable devices 204-220 based on the patient condition 234. For example, if the user actuates the buttons B9, B11 associated with the fowler adjustment device 216 and the gatch adjustment device 218 simultaneously, the controller 222 may control the rate of operation for the fowler adjustment device 216 and the gatch adjustment device 218 in a manner to minimize the discomfort experienced by the patient disposed on the patient support surface 48, 52. As one example, based on the simultaneous actuation of buttons B9, B11, the controller 222 may first transmit an output signal to the fowler adjustment device 216 with a FAST rate of operation for a period of time, and then subsequently transmit an output signal to both the fowler adjustment device 216 and the gatch adjustment device 218 with a SLOW rate of operation. Of course, any combination of rates of operation for any suitable time periods, in any suitable sequence, are contemplated.

The controller 222 may be further configured to determine a movement sensitivity score based on the patient condition 234, and be configured to determine the desired rate of operation based on the movement sensitivity score. In one embodiment, the movement sensitivity score is based on a skin injury profile. In another embodiment, the movement sensitivity score is computed based on the weight of the patient, the position of the patient, temperature of the patient, temperature of the room, the moisture level, the patient's medication history, the sensed patient condition, or combinations thereof. Of course, the movement sensitivity score can be determined based on a combination of the patient-related information that makes up the patient condition 234. The controller 222 may utilize a look-up table to determine the rate of operation, or may utilize a suitable algorithm. Finally, the movement sensitivity score can be inputted by the user with the user input device 228 or the voice actuation interface 230.

Figure 11:
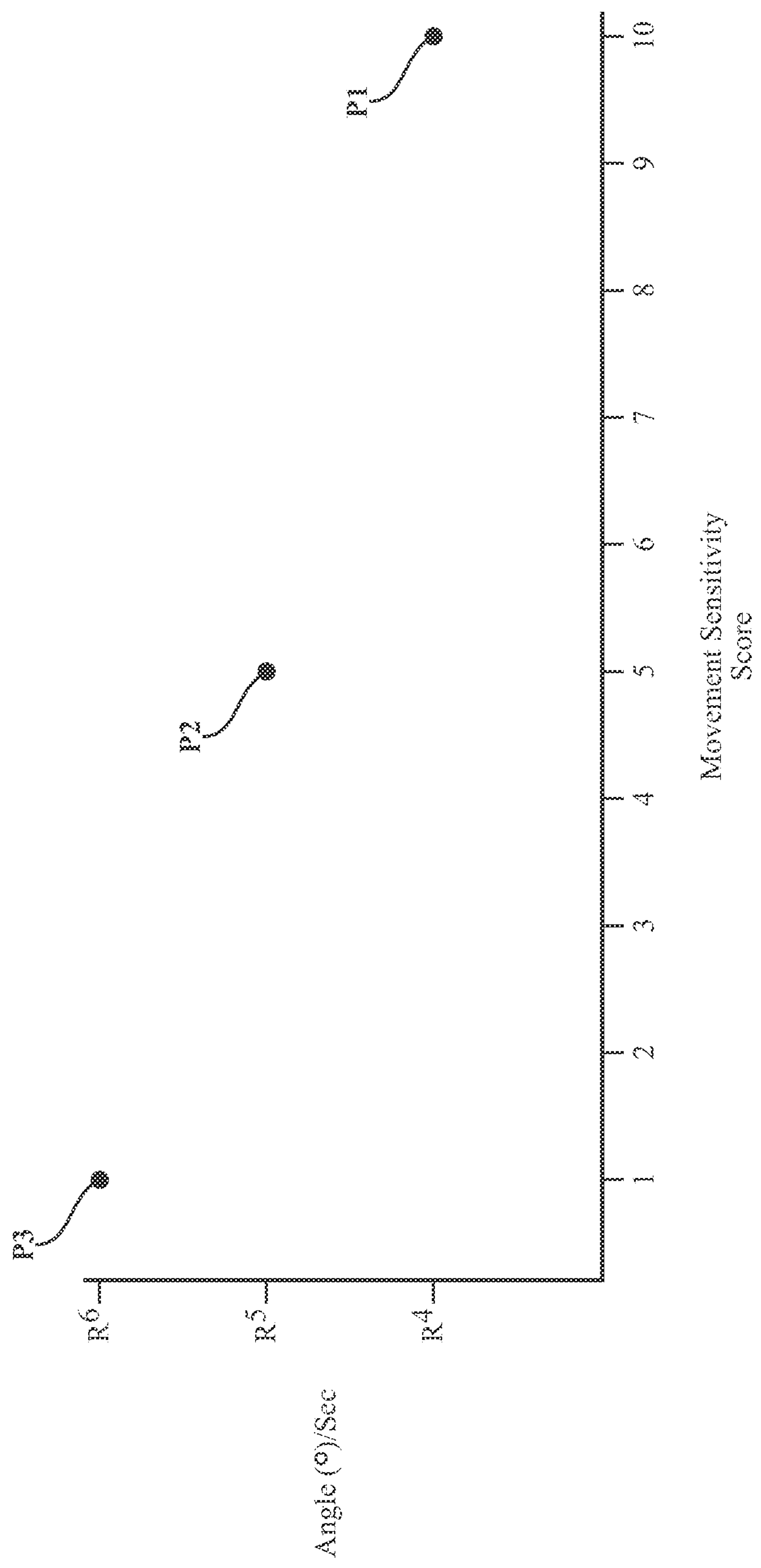
FIG. 11 is a chart showing different rates of operation for a fowler adjustment device based on different movement sensitivity scores.

Referring the chart of FIG. 11, in one example, the actuatable device 200 is the fowler adjustment device 216. P1 shows a fourth rate of operation R4 of the fowler adjustment device 216 suitable for a patient that that has a movement sensitivity score of 10, such as a burn victim. P2 shows the fifth rate of operation R5 for the fowler adjustment device 216 suitable for a patient that has a movement sensitivity score of 5, such as patient with a history of skin lesions. P3 shows a sixth rate of operation R6 for the fowler adjustment device 216 suitable for patient that has a movement sensitivity score of 1, such as a patient that does not require extraordinary caution with movement. The controller 222 may be configured to control the fowler adjustment device 216 at rates R4, R5, R6 based on the movement sensitivity score.

The controller 222 may determine what types of motion and what rate of operations are appropriate for a person with a given movement sensitivity score. Thus, as described above, the controller 222 may prevent actuation of one or more actuatable devices or one or more rates of operation if the movement sensitivity score exceeds a predetermined threshold. The controller 222 may cooperate with the indicator device 242 to output the movement sensitivity score and suitable rates of operation for the patient having the determined movement sensitivity score.

The controller 222 may be further configured to control the rate of operation for the actuatable devices 204-220 based on the state of the actuatable devices 204-220, based on input from the sensing system 236, or based on the sensed state or position of each actuator 202 of the actuatable devices 204-220. As described above, the state of the actuatable device 204-220 may comprise a sensed current position of the actuatable device 204-220. The sensed current position of the actuators 202 may comprise the sensed current position of all actuators 202 associated with the actuatable device 204-220.

In certain embodiments, the controller 222 is configured to determine the desired rate of operation based on a combination of the state of the actuatable device 204-220 and/or the presence of the patient adjacent to one or more of the patient support surfaces 48, 52, 111. If the controller 222 determines that the actuatable device 204-220 has a first state and that no patient is positioned adjacent to patient support surfaces 48, 52, 111, the controller 222 may determine a first desired rate of operation; whereas, if the controller 222 determines that the actuatable device 204-220 has the first state and that the patient is positioned adjacent to the patient support surfaces 48, 52, 111 the controller 222 may determine a second desired rate of operation. In such a configuration, the first desired rate of operation is higher than the second desired rate of operation.

The controller 222 may be configured to determine the state of the actuatable device 204-220 by sensing a current position of the actuators 202 of the actuatable device 204-220. In such a configuration, the controller 222 is configured to determine the desired rate of operation based on the combination of the sensed current position of the actuators 202, and the patient presence input signal. This may allow the controller 222 to quickly change the state of the actuatable device 200 from the first state to the second state without risk of causing injury to the patient. Other ways of determining the state of the actuatable devices 204-220 are also contemplated.

The actuatable devices 204-220 may have many possible configurations for performing the predetermined functions of the patient support system PS. Exemplary configurations of some of the actuatable devices 204-220 are described further below, comprising the coordinated motion device 204, patient raising device 206, the patient turning device 208, the patient centering device 210, the patient ingress/egress device 212, the lift device 214, the fowler adjustment device 216, the gatch adjustment device 218, and the transport device 220. It should be understood that numerous configurations of the actuatable devices 204-220, other than those specifically described, are possible. Additionally, numerous scenarios exist in which the rate of operation of these actuatable devices 204-220 can be operated based on the patient condition 234. As previously described, the controller 222 may control the rate of operation of these actuatable devices 204-220 based on the patient condition 234, as obtained from the EMR 238 or the sensing system 236. A few exemplary scenarios of how these actuatable devices 204-220 may be utilized are also described below. However, numerous other scenarios not described herein, are also possible.

Figure 12:
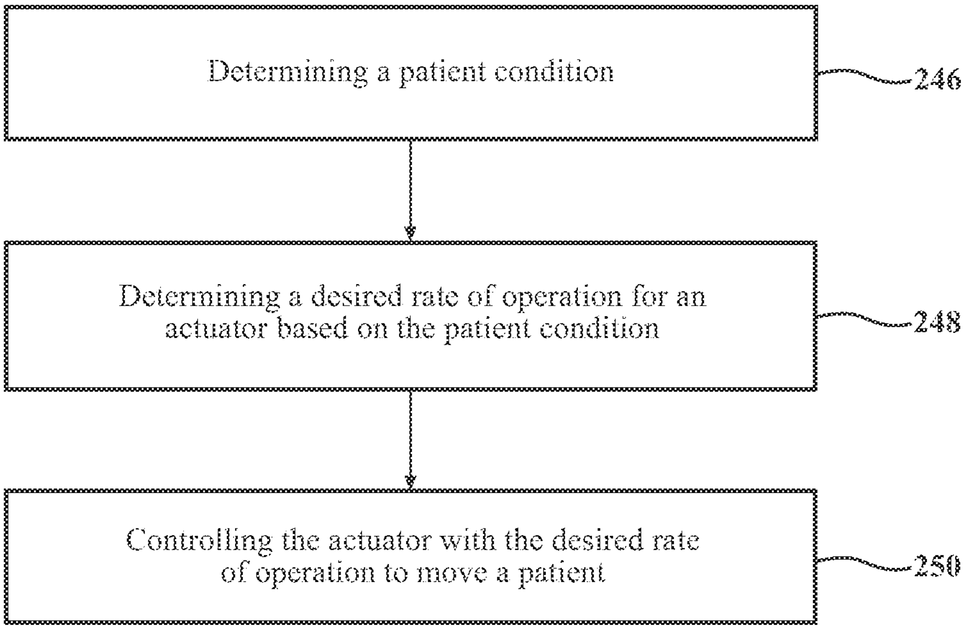
FIG. 12 is a schematic of a method of controlling a rate of operation for an actuatable device based on a patient condition.

Referring to FIG. 12, a method of controlling the actuator is also provided. The method comprises the step 246 of determining the patient condition for the patient; the step 248 of determining a desired rate of operation for the actuator based on the patient condition; and the step 250 of controlling the actuator with the desired rate of operation to move the patient.

Figure 13:
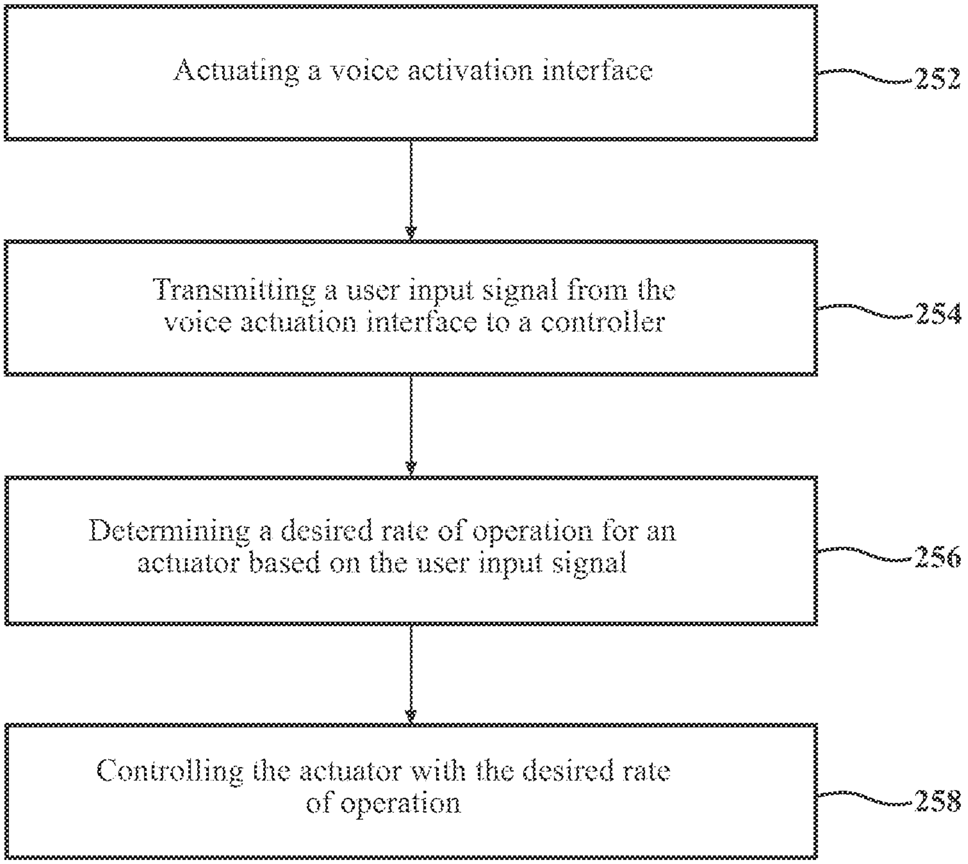
FIG. 13 is a schematic of a method of controlling a rate of operation for an actuatable device with a voice actuation interface.

In another embodiment, referring to FIG. 13, the method comprises a step 252 of actuating the voice actuation interface; a step 254 of transmitting the user input signal from the voice actuation interface to the controller; a step 256 of determining a desired rate of operation for the actuator based on the user input signal; and a step 258 of controlling the actuator with the desired rate of operation.

Referring to FIG. 6, the coordinated motion device 204 may comprise an actuator system comprising two or more actuators 202. The coordinated motion device 204 may be configured to perform compound movements that, when a patient is present, causes multiple portions of the patient's body to be moved in a coordinated manner. Thus, the coordinated motion device 204 is capable of assuming different states. Each state pertains to a different orientation of one or more portions of the patient support surfaces 48, 52, 111. In one embodiment, the coordinated motion device 204 is capable of changing the angular orientation of various portions of the patient's body simultaneously, such as the patient's head, back, thighs, calves, and/or feet. The actuators 202 and patient support surfaces 48, 52, 111 of the coordinated motion device 204 cooperate to assume a first state and a second state. The controller 222 is configured to control a rate of operation at which the actuators 202 and the patient support surface 48, 52, 111 cooperate to move from the first state to the second state.

Figure 14:
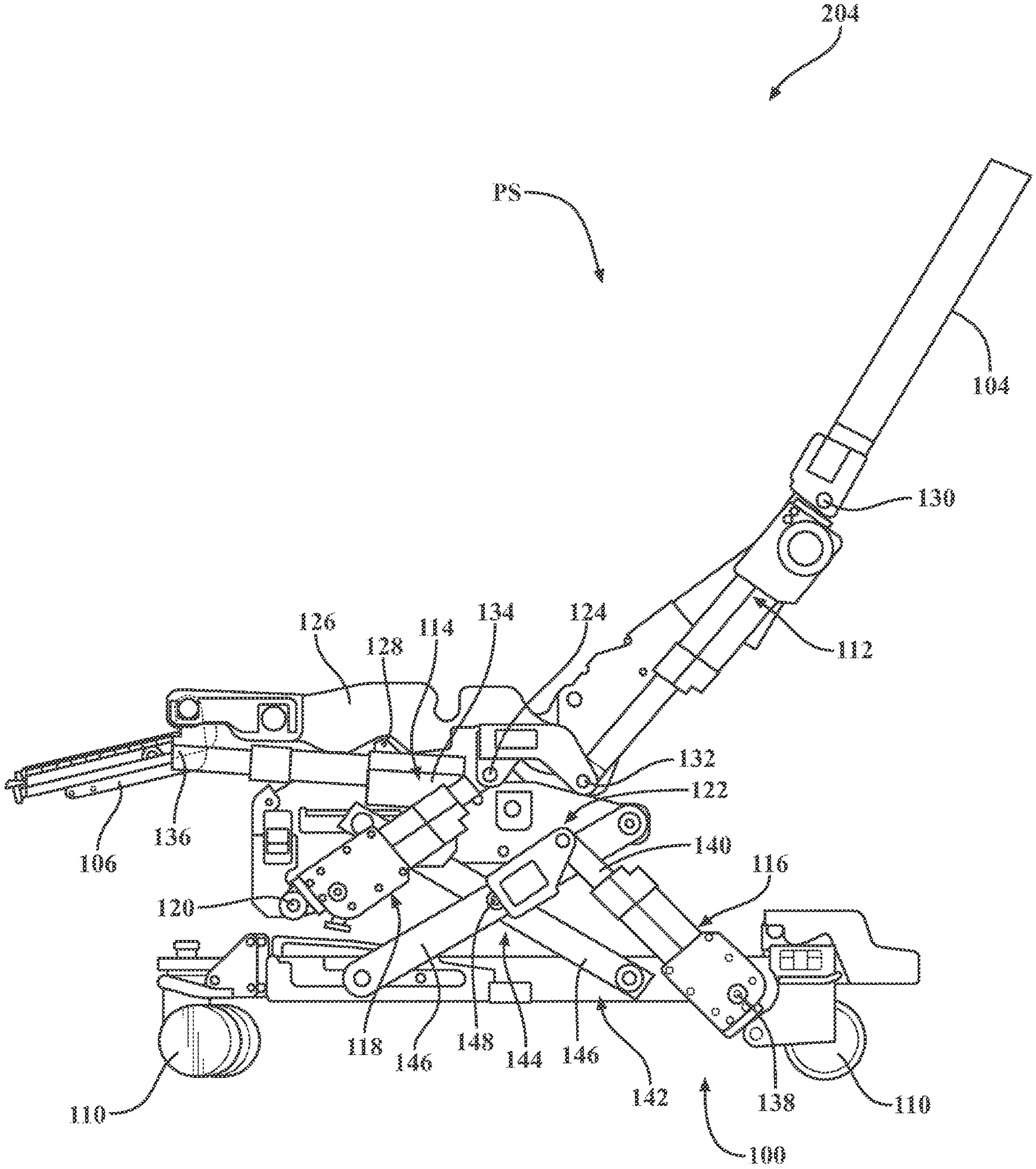
FIG. 14 is a side view of the coordinated motion device of FIG. 3 with the seat, back rest, and leg rest removed.

Referring to FIG. 3 and FIGS. 4A-4F, in one embodiment, the chair 100 comprises the coordinated motion device 204. Referring now to FIG. 14, the chair 100 comprises a back rest actuator 112, a leg rest actuator 114, a lift actuator 116, and a seat actuator 118. The controller 222 is coupled to each of these actuators and is configured to control the rate of operation of each actuator 112, 114, 116, 118. While four actuators are shown in this exemplary embodiment, it should be appreciated that the coordinated motion device 204 may comprise only two or three actuators, or may comprise more than four actuators. Similarly, while in the illustrated embodiment the chair 100 is displayed. The patient support apparatus 30 of FIG. 1A may comprise the coordinated motion device 204. For example, by jointly controlling the fowler adjustment device 216 and the gatch adjustment device 218 of the patient support apparatus 30, the controller 222 essentially creates a coordinated motion device 204 that is capable of assuming multiple states.

As described above, each state of the coordinated motion device 204 pertains to a different orientation of one or more portions of the patient support surfaces 48, 52, 111. In FIG. 3, the patient support surface 111 is cooperatively defined by the patient-facing surface of the seat 102, the patient-facing surface of the back rest 104, and the patient-facing surface of the leg rest 106. Thus, when the chair 100 is in the flat state (See FIG. 4B), the patient support surface 111 defined by the seat 102, the back rest 104, and the leg rest 106 are generally level with one another, and generally parallel to the floor surface. On the other hand, in the standing state (See FIG. 4F), the seat 102 assumes an angle of approximately 30 degrees, whereas the back rest 104 and the leg rest 106 are perpendicular to the floor. When the patient is disposed on the chair 100 while the chair 100 from one state to another, different portions of the patient's body are moved in a coordinated manner (e.g., the patient's back and the patient's legs are changing their angle relative to the floor simultaneously).

Referring now to FIG. 8, as described above, the chair 100 comprises a chair control panel CCP that comprises buttons B21-B26 that correspond to the different states that can be assumed by the coordinated motion device 204, i.e., the chair 100. When a user presses on any one of the buttons B21-B26, the controller 222 will activate the necessary ones of actuators 112, 114, 116, 118 to move the chair 100 to the corresponding state. Buttons B13, B14, B15 correspond to the FAST, MEDIUM, and SLOW rates of operation as described above with respect to the patient support apparatus 30. Buttons B27 and B28 transmit a user input signal that causes the height of the seat 102 to raise and lower relative to the floor.

Figure 15A:
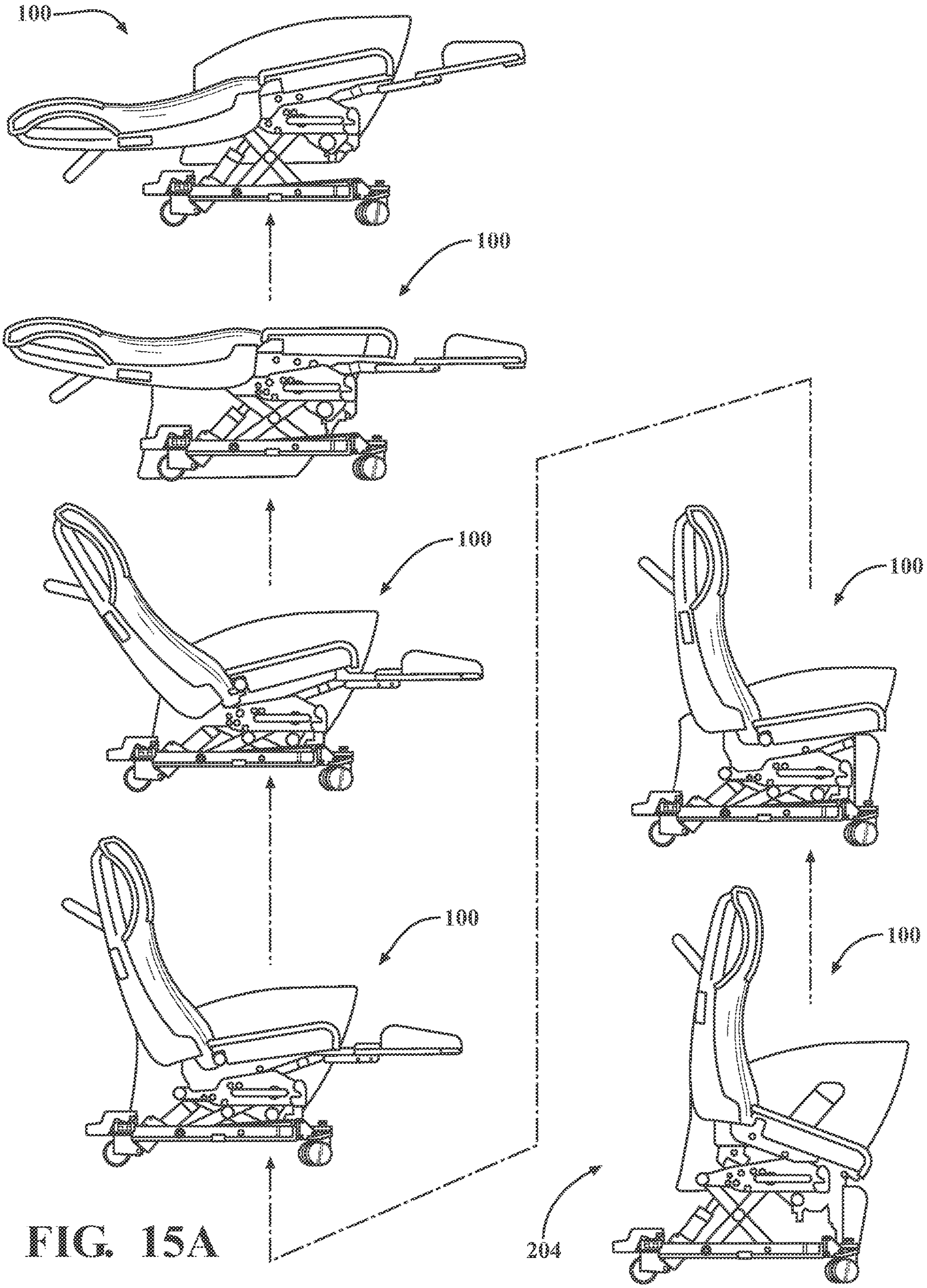
FIG. 15A shows a progression of states assumed by the coordinated motion device of FIG. 3.

Referring to FIG. 15A, when the user actuates button B25 corresponding to the flat state (FIG. 4B), and the chair 100 is currently in the standing state (FIG. 4F), the controller 222 may be configured to control the actuators 112, 114, 116, 118 such that the patient support surface 111 defined by the chair 100 will pass through the first upright state (FIG. 4E), the second upright state (4D), and the recline state (FIG. 4C) before eventually reaching flat state (FIG. 4B). This is because, in some configurations, all six states (FIG. 4A-FIG. 4E) of the chair 100 are arranged sequentially and the chair 100 is only able to move from one state to another in the predefined sequence. Similarly, regardless of the initial state of the chair 100, it will always move sequentially from its current state to its final state by moving through certain intermediate states.

However, it should be appreciated the chair 100 is movable to a virtually infinite number of intermediate states between the six states shown in FIGS. 4A-4F and FIG. 15A. Thus, the patient support surface 111 defined by the seat rest 102, the back rest 104, and the leg rest 106 is movable to a virtually infinite number of positions, which accordingly, are capable of positioning the patient disposed on the patient support surface 111 in a virtually infinite number of positions.

Referring again to FIG. 14, in the illustrated embodiment, seat actuator 118 comprises a stationary end 120 pivotally mounted a chassis 122. Seat actuator 118 further comprises an extendible end 124 that is pivotally mounted to a seat frame 126. When seat actuator 118 extends, extendible end 124 causes the seat frame 126 to tilt in such a manner that a forward end of seat 102 moves downward relative a backward end of seat 102 (i.e., the seat frame 126 will rotate in a counter clockwise direction about seat pivot axis 128). The retraction of seat actuator 118 will, in contrast, cause seat frame 126 to tilt in the opposite manner (i.e., seat frame 126 will rotate in a clockwise direction). The controller 222 may control the rate of operation of the seat actuator 118 in order to control the rate of tilt of the seat 102.

Back rest actuator 112 comprises a stationary end 130 that is mounted to back rest 104 and an extendible end 132 that is mounted to the seat frame 126. The extension and retraction of back rest actuator 112 will therefore cause back rest 104 to pivot with respect to seat frame 126. More specifically, when back rest actuator 112 extends, back rest 104 will rotate in a counterclockwise direction. In contrast, when back rest actuator 112 retracts, back rest 104 will rotate in a clockwise direction. Because back rest 104 is coupled to the seat frame 126, the rotation of seat frame 126 will also cause back rest 104 to rotate. In other words, the relative angle between back rest 104 and seat 102 will only change when back rest actuator 112 is actuated (and not when seat actuator 118 extends or retracts while back rest actuator 112 does not change length). The angle of back rest 104 with respect to the floor (or another fixed reference), however, will change as seat frame 126 pivots about seat pivot axis 128. The controller 222 may control the rate of operation of the seat actuator 118 in order to control the rate at which the back rest 104 rotates in the clockwise or counterclockwise directions relative to the seat frame 126.

Leg rest actuator 114 comprises a stationary end 134 that is mounted to seat frame 126 and an extendible end 136 that is mounted to leg rest 106. The extension of leg rest actuator 114 therefore will pivot leg rest 106 from a retracted position to an extended position. The extension and retraction of leg rest actuator 114 will change the orientation of leg rest 106 with respect to seat frame 126. The orientation of leg rest 106 with respect to seat frame 126 will not change based on the extension or retraction of any other actuators 112, 116, 118. The orientation of leg rest 106 with respect to the floor will change when seat frame 126 is pivoted about seat pivot axis 128 by seat actuator 118. The controller 222 may control the rate of operation for the leg rest actuator 114 to control the rate at which the leg rest 106 pivots from the retracted position to the extended position.

In summary, the pivoting of seat frame 126 about its pivot axis 128 will therefore change the orientations of all of seat 102, back rest 104, and leg rest 106 with respect to the floor, but will not, by itself change the orientations of any of these components (seat 102, back rest 104, and leg rest 106) with respect to each other.

Lift actuator 116 comprises a stationary end 138 that is coupled to a base 142 and an extendible end 140 that is coupled to an X-frame lift 144. The X-frame lift 144 comprises two legs 146 that are pivotally coupled to each other about a center axis 148. When lift actuator 116 extends or retracts, the relative angle between each of the legs 146 changes, which changes the overall height of the X-frame lift 144. Further, because chassis 122 is mounted on a top end of X-frame lift 144, the changing height of the scissor lift 144 changes the height of chassis 122. Lift actuator 116 therefore raises the height of chassis 122 when it extends and lowers the height of chassis 122 when it retracts. Because seat frame 126 is mounted on chassis 122, and because back rest 104 and leg rest 106 are both mounted to seat frame 126, raising and lowering the height of chassis 122 simultaneously raises and lowers the height of the seat 102, back rest 104, and leg rest 106. However, extending and retracting lift actuator 116 does not, by itself, change the angular orientations of any of leg rest 106, back rest 104, and/or seat 102 with respect to each other or the floor. The controller 222 may be coupled to the lift actuator 116 to control the rate of operation for the lift actuator 116 to control the rate operation at which the seat 102, back rest 104, and leg rest 106 are raised or lowered relative to the floor.

Figure 15B:
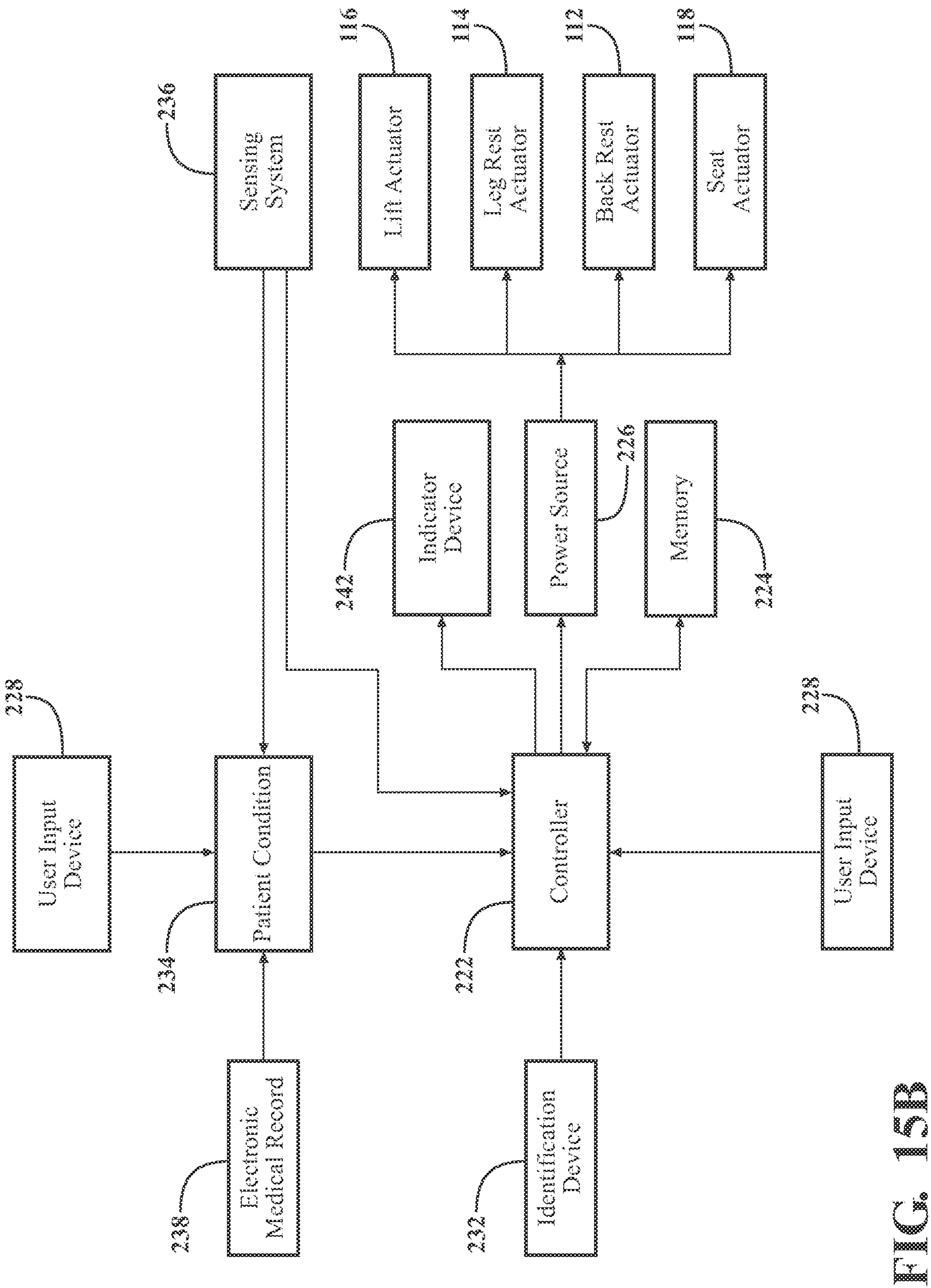
FIG. 15B shows a schematic view of a control system for the coordinated motion device of FIG. 3.

Referring to FIG. 15B, the controller 222 may use predefined positions of each actuator 112, 114, 116, 118 for each of the desired states, as target values for controlling actuators 112, 114, 116, 118. For example, memory 224 may comprise data associated with the desired positions for actuators 112, 114, 116, 118 for each state of the chair 100. Whenever chair 100 is commanded by a user to move from its current position to one of the desired states, the controller 222 may use the stored position data in the memory 224 as the target positions in the control of the actuators 112, 114, 116, 118. The sensing system 236 may be configured to detect the current positions of each actuator 112, 114, 116, and 118 to determine when the actual position matches the predefined position. Of course, other ways of controlling the actuators 112, 114, 116, 118 to reach each of the desired states are contemplated. In this manner, the controller 222 can determine what positions of each actuator 112, 114, 116, 118 correspond to each state of the chair 100.

The controller 222 may be configured to control each of the actuators 112, 114, 116, and 118 in a coordinated manner such that each actuator 112, 114, 116, and 118 arrives at the desired state simultaneously, or substantially simultaneously, as disclosed in the commonly assigned U.S. patent application Ser. No. 14/801,167, entitled "MEDICAL SUPPORT APPARATUS" which is hereby incorporated by reference. Thus, the controller 222 may selectively control the operation of the actuators 112, 114, 116, 118 of the chair 100 such that patient support surface 111 reaches the desired state in a fluid manner.

If the controller 222 determines that no patient occupies the patient support system PS, such as the chair 100, based on the patient presence input signal, the controller 222 may allow the coordinated motion device 204 to move in an uncoordinated manner. For example, if the controller 222 determines that the patient is not adjacent to the patient support surface 111, the controller may disengage the coordinated motion mode, which allows the actuators 112, 114, 116, 118 to move such that they do not necessarily reach the state simultaneously, or substantially simultaneously.

By selectively controlling the rates of operation for one or more actuators 112, 114, 116, 118, the controller 222 may effectively control the rate at which the coordinated motion device 204 moves from one state to another. Buttons B13, B14, and B15 correspond to FAST, MEDIUM, and SLOW rates of operation. If a user depresses rate selector button B13 corresponding to the FAST rate of operation, and subsequently depresses button B21 corresponding to the standing state, the controller 222 controls the rate of operation of the actuators 112, 114, 116, 118 such that the chair 100 moves from its current state towards the upright state at an accelerated rate. Similarly, if the user depresses rate selector button B15 corresponding to the SLOW rate of operation, and subsequently depresses button B25 corresponding to the flat state, the controller 222 controls the rate of operation of the actuators 112, 114, 116, 118 such that the chair 100 moves from its current state toward to the flat state at the SLOW rate of operation. Even at this SLOW rate of operation, the controller 222 may control the actuators 112, 114, 116, 118 such that they move in a coordinated manner and arrive at the desired state at substantially the same time.

As described above, the controller 222 may control the rate of operation of the actuators 112, 114, 116, 118 based on both the user input signal and the patient presence input signal. Accordingly, if the patient presence sensor 241 detects that the patient is adjacent to the patient support surface 111, the controller 222, based on the patient presence input signal may determine whether the user-selected rate of operation is suitable. Thus, if the patient presence input signal indicates that the patient is not adjacent to the patient support surface 111, the controller 222 may generally permit faster rates of operation for the actuators 112, 114, 116, and 118. Thus, simplistically, if no patient is present, the controller 222 may control the actuators 112, 114, 116, 118 at the FAST rate of operation. If the patient is present, the controller 222 may control the actuators 112, 114, 116, 118 at the SLOW rate of operation, even if the user-selected rate of operation is the FAST rate of operation. Such automatic control ensures that the patient is not moved at unsuitable speeds.

For example, if the chair 100 is currently in the standing state (See FIG. 4F), and the user depresses button B13 corresponding to the FAST rate of operation, and subsequently depresses button B25 corresponding to the flat state, the controller 222 may query the patient presence sensor 241 to determine whether the patient is adjacent to the patient support surface 111. If the patient presence sensor 241 determines that the patient is adjacent to the patient support surface 111, the controller 222 may not permit the chair 100 to operate at the user-selected rate of operation. Instead, the controller 222 may automatically select a suitable rate of operation, typically a slower rate of operation, than the user-selected rate of operation. However, if the patient presence sensor 241 determines that the patient is not adjacent to the patient support surface 111, the controller 222 may automatically select a faster rate of operation than the user-selected rate of operation. Such a feature may permit the user to quickly place the chair 100 in the desired state without risk of patient injury.

As described above, the controller 222 may control the rate of operation of the actuators 112, 114, 116, 118 based on both the user input signal and the patient condition 234. In such an embodiment, the controller 222, based on the patient condition 234, may determine whether the user-selected rate of operation is suitable. Thus, if user-selected rated of operation is unsuitable for the patient condition 234 of the patient disposed on the patient support surface 111, the controller 222 may automatically adjust the rate of operation to a rate of operation that is suitable for the patient condition 234. For example, if the chair 100 is currently in the standing state and the user depresses button B26 and button B13, indicating that the user desires that the chair 100 move to the Trendelenburg state at a FAST rate of operation, the controller 222 may query the patient condition 234 before moving the chair 100 to the Trendelenburg state at the FAST rate of operation. Thus, if the patient condition 234 indicates that the patient has a skin injury, the controller 222 may move the chair 100 to the Trendelenburg state at a SLOW rate of operation.

If the controller 222 determines that the chair 100 is in a first state and that the user desires that the chair 100 be moved to a second state, the controller 222 may control the rate of operation of the chair 100 based on the current state. For example, if the chair 100 is in the standing state and the user desires that the chair 100 be placed in the flat state, the controller 222 may determine that a FAST rate of operation is desired. In contrast, if the user simply wishes to move from the standing state to the reclined state, the controller 222 may control the rate of operation of the chair 100 at the SLOW rate of operation. The controller 222 may determine the desired rate of operation for the chair 100 based on how many intermediate states are between the current state and the desired state, or the distance that the actuators 112, 114, 116, 118 would need to extend/retract to move from the current state to the desired state.

The controller 222 may also be configured to determine the direction of movement of the actuatable device 204-220, and determine the desired rate of operation based on the direction of movement and/or the patient presence signal. Thus, the controller 222 may determine the desired rate of operation of the actuatable device to be increased or decreased in one direction relative to the desired rate of operation in the opposite direction. For example, with reference to FIGS. 4A-4F, the controller 222 may determine that the chair 100 is moving in a first direction from the flat state (FIG. 4B) to the stand state (FIG. 4F) by receiving inputs from the underlying actuators 112, 114, 116, 118. The controller 222 may determine the desired rate of operation to be a first rate of operation based on motion in that first direction. The controller 222 may further determines that the chair is moving in a second direction from the stand state (FIG. 4F) to the flat state (FIG. 4B) based on inputs from the underlying actuators. Because the second direction of motion is likely associated with absence of the patient, the controller 222 may determine the desired rate of operation to be a second rate of operation, with the second rate of operation being greater than the first rate of operation. It should be appreciated that while this example was described in view of the chair 100, the controller 222 may determine the rate of operation for any actuatable devices based on the direction of movement, and thus, asymmetric rate of operation control is enabled. Other ways of determining the state of the actuatable devices 204-220 are also contemplated. For example, the controller 222 may determine rate of operation based on both the direction of movement and the patient presence.

Figure 16:
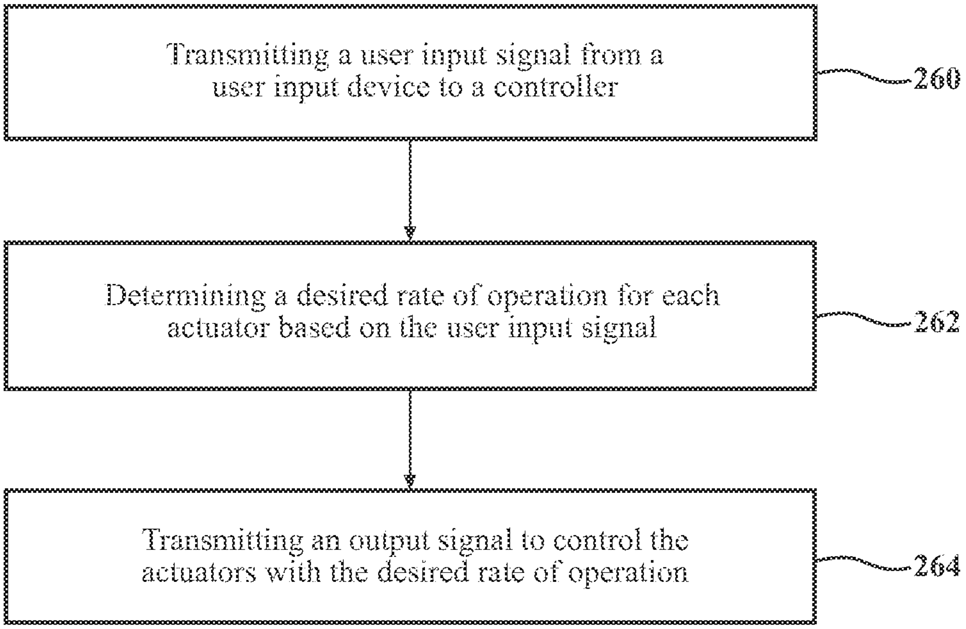
FIG. 16 is a schematic of a method of controlling a rate of operation for the coordinated motion device.

Referring to FIG. 16, a method of controlling the coordinated motion device is also provided. The method comprises a step 260 of transmitting a user input signal from the user input device to the controller; a step 262 of determining a desired rate of operation for each of the actuators based on the user input signal; and a step 264 of transmitting an output signal to control the actuators with the desired rate of operation.

Figure 17A:
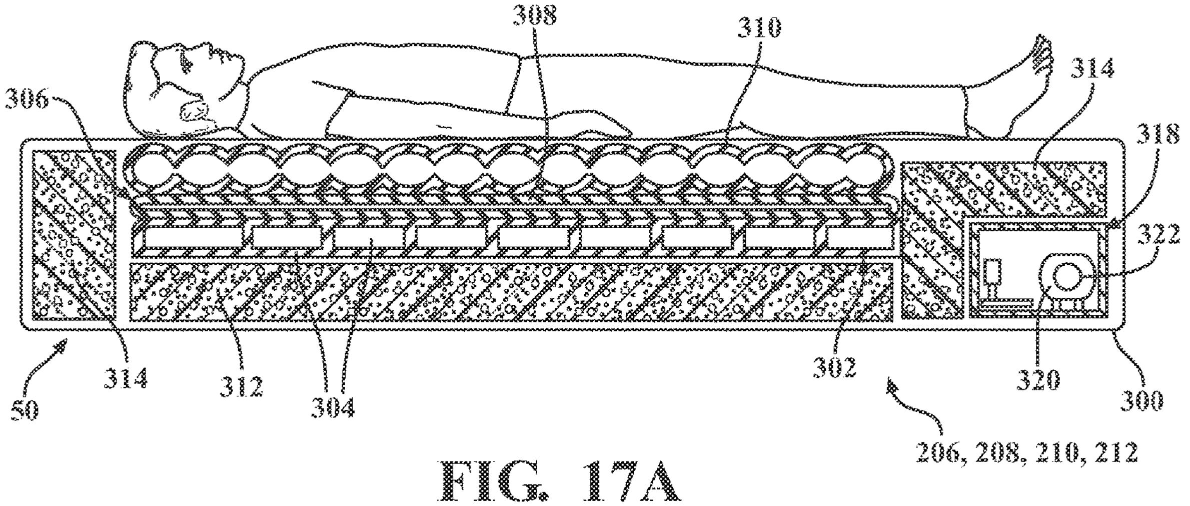
FIG. 17A is a cross-sectional view of a mattress taken longitudinally along the mattress to illustrate a pump and inflatable bladders.
Figure 17B:
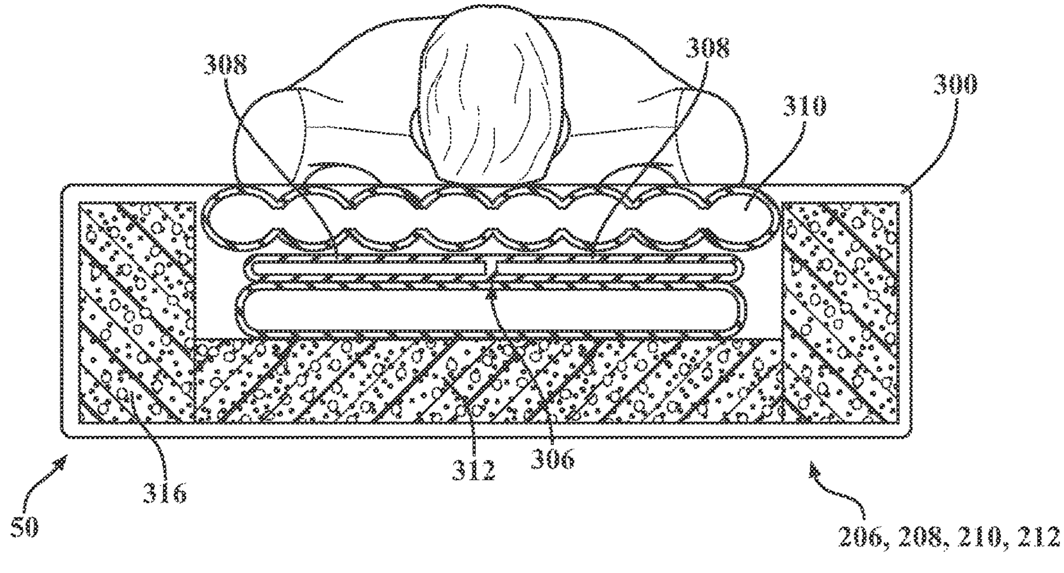
FIG. 17B is another cross-sectional view of the mattress taken laterally across the mattress.

Referring to FIGS. 17A and 17B, the patient raising device 206, the patient centering device 210, and the patient turning device 208 may be integrated into the mattress 50. In one embodiment, the mattress 50 is referred to as a self-contained therapy mattress since several working components of the mattress 50 that are used to carry out the functions of the patient raising device 206, the patient centering device 210, and the patient turning device 208 are enclosed by a cover 300 of the mattress 50. The cover 300 can be any conventional material including, but not limited to natural fibers, polymeric materials, or combinations thereof. The cover 300 may be formed of a vapor permeable material. The cover 300 may be flexible and stretchable to accommodate inflation of various inflatable bladders described herein. Of course, it is further contemplated that the mattress 50 may be configured to perform other functions, such as patient egress/ingress, patient temperature control, etc.

The patient raising device 206 is configured to perform the function of moving the patient from a slouched position towards a non-slouched position by moving the patient towards the head end of the patient support system PS. The illustrated patient raising device 206 comprises a patient raising bladder structure 302 positioned within the cover 300. The patient raising bladder structure 302 comprises patient raising inflation bladders 304 that are connected together longitudinally so that each of the patient raising inflation bladders 304 spans across a majority of a width of the mattress 50 below the patient and together, the patient raising inflation bladders 304 span a majority of a length of the mattress 50 below the patient.

Figure 18A:
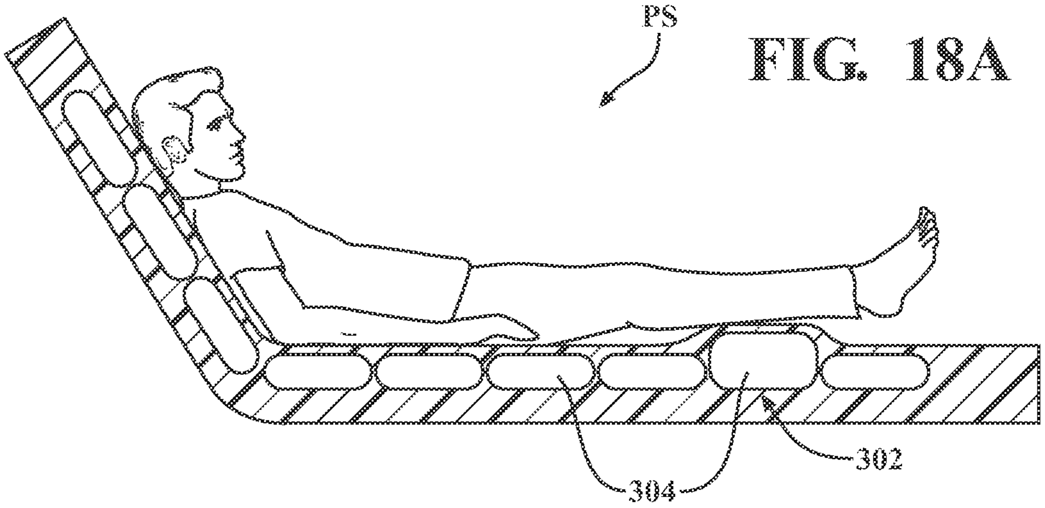
FIGS. 18A, 18B, and 18C are illustrations of raising a patient from a slouched position to a raised position.
Figure 18B:
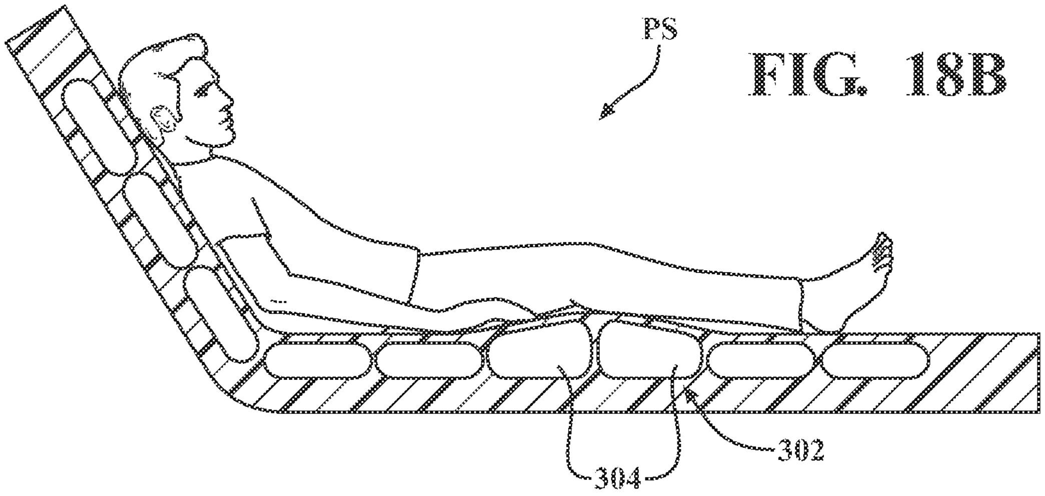
Figure 18C:
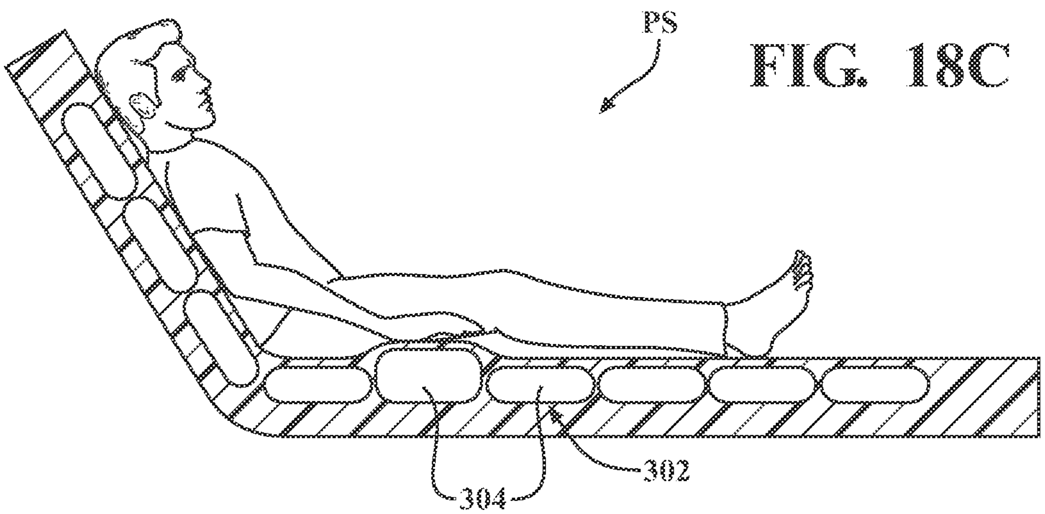

In the embodiment shown, nine patient raising inflation bladders 304 assist in raising the patient from a slouched position. Additional patient raising inflation bladders 304 may be employed to raise the patient, or in some cases, fewer patient raising inflation bladders may be used. FIGS. 18A through 18C illustrate a progressive inflation scheme used to raise the patient six inches from the slouched position (see FIG. 18A). The patient raising inflation bladders 304 are inflated and deflated to create a wave-like force directed towards the head end of the patient support apparatus 30 to push the patient toward the head end. As shown, in some cases, only one of the patient raising inflation bladders 304 are fully inflated at a time to create the wave-like force needed to raise the patient. Once fully inflated, each patient raising inflation bladder 304 begins to deflate and the next adjacent patient raising inflation bladder 304 toward the head end begins to inflate (see, e.g., FIG. 18B).

Referring to FIGS. 19A and 19B, the patient centering device 210 is configured to move the patient from an off-center position toward the longitudinal centerline CL of the mattress 50, such as when the patient has shifted too far to one side or the other of the mattress 50. Referring back to FIGS. 17A and 17B, the patient centering device 210 comprises a patient centering/turning bladder structure 306 positioned within the cover 300. The patient centering/turning bladder structure 306 comprises a pair of elongate bladders 308 that are connected together along a longitudinal seam so that each of the elongate bladders 308 spans a majority of the length of the mattress 50, but spans one half or less the width of the mattress 50, below the patient. The elongate bladders 308 are selectively inflated to guide the patient toward the longitudinal centerline CL of the mattress 50 when desired. Referring to FIGS. 19A and 19B, inflation of one of the elongate bladders 308 is shown to urge the patient toward the centerline CL of the mattress 50. Movement of the patient toward the centerline CL may not be immediate, but may occur gradually as the elongate bladders 308 remains inflated.

The patient turning device 208 is configured to perform the function of turning the patient and/or providing rotational therapy to the patient. The patient turning device 208 may utilize the same patient centering/turning bladder structure 306 as the patient centering device 210. When the patient turning device 208 is operated, the elongate bladders 308 are independently inflated to raise one side or the other of the patient. Referring to FIGS. 20A and 20B, if used for rotation therapy, then the elongate bladders 308 are used for rotation therapy by sequentially inflating/deflating the elongate bladders 308 to raise one side of the patient to an angle β, lower the patient, and then raise the other side of the patient to the angle β such that the patient experiences a side-to-side rotation that shifts pressures between the patient and the mattress 50. The method may comprise controlling the pump with the desired rate of operation to control the rate at which the patient turns.

The patient ingress/egress device 212 is configured to perform the function of easing ingress and/or egress of the patient to and/or from the patient support apparatus 30. Referring back to FIGS. 17A and 17B, the patient ingress/egress device 212 comprises a main air bladder 310 positioned within the cover 300. The main air bladder 310 is sized to extend substantially the full width of the mattress 50 and a majority of the length of the mattress 50. The main air bladder 310 comprises, in the embodiment shown, a single air bladder than can be inflated and deflated, depending on the needs of the patient or the caregiver. The main air bladder 310 may be fully inflated to ease ingress and egress of the patient. For instance, if the main air bladder 310 is less than fully inflated, e.g., to soften the mattress 50 and provide additional comfort to the patient, it can be difficult for the patient to move across the mattress 50 for ingress or egress. Accordingly, by fully inflating, and stiffening the mattress 50, movement across the mattress 50 can be made easier for the patient.

The patient raising bladder structure 302, the patient centering/turning bladder structure 306, and the main air bladder 310 are supported within the cover 300 of the mattress 50 by a base cushion 312. The base cushion 312 is located between outside lateral cushions 314 and outside longitudinal cushions 316. The cushions 312, 314, 316 may be rigid or flexible, may comprise one or more air bladders, or simply be constructed of conventional bedding materials such as foam, and the like. The cushions 312, 314, 316 may be separate cushions or may be integrated into an integral cushion structure.

A control unit 318 is shown at the foot end of the mattress 50 in FIG. 17A. The control unit 318 comprises a rigid box that encloses a pump 320 and a motor 322 for operating the pump 320. As shown, the control unit 318 may fit within the cover 300 of the mattress 50 or outside of the cover 300. The pump 320 is used to inflate the patient raising inflation bladders 304, the elongate bladders 308, and the main air bladder 310. Other configurations of the control unit 318 are also possible.

Figure 21:
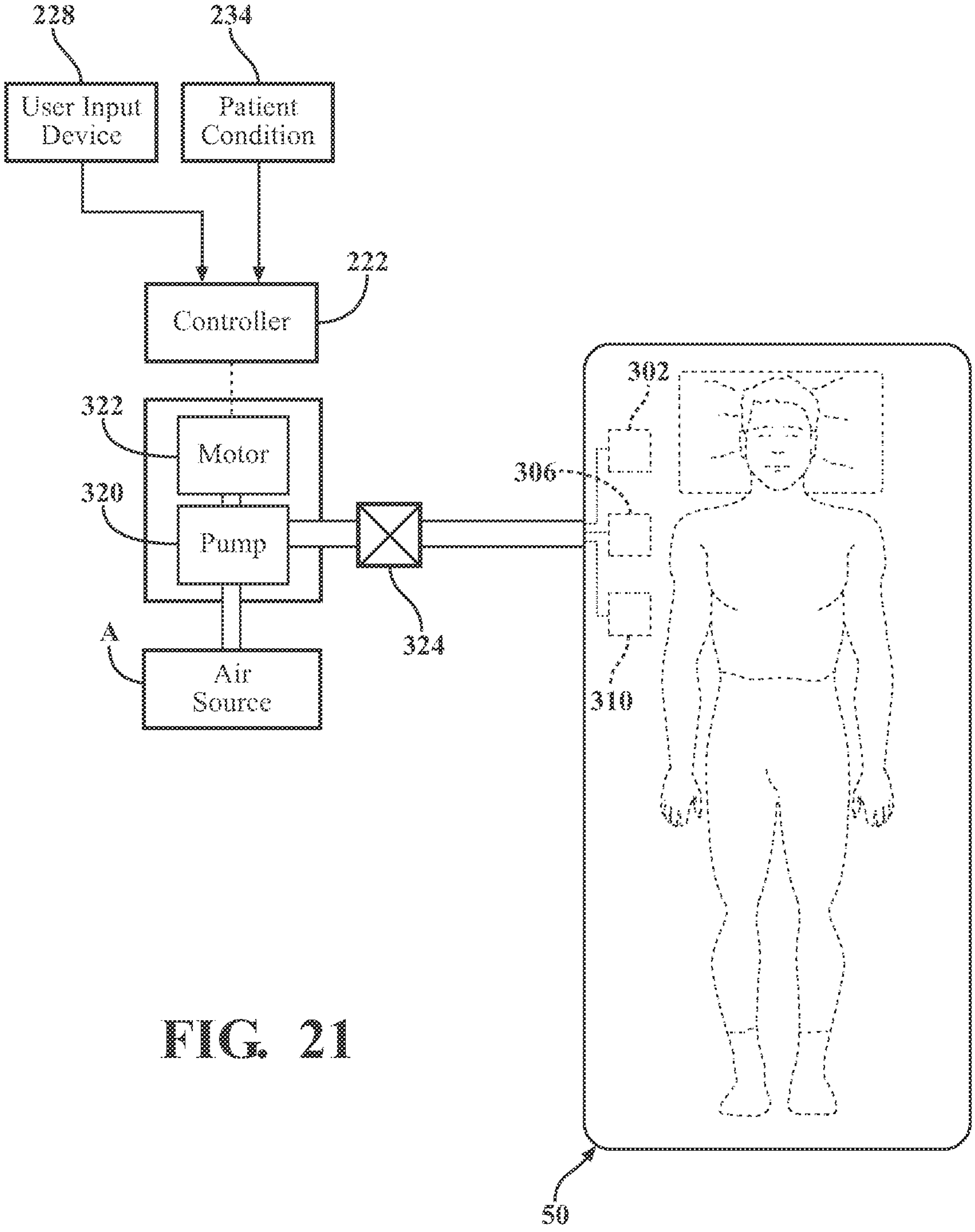
FIG. 21 is a simplified fluid and control schematic for a patient raising device, a patient centering/turning device, and a patient ingress/egress device.

Referring to FIG. 21, general fluid flow schematics for the patient raising bladder structure 302, the patient centering/turning bladder structure 306, and the main air bladder 310, respectively, are shown. The fluid flow schematics generally illustrate the fluid flow paths in which fluid, such as air, flow from an air source A (such as outside air) via the pump 320 to the patient raising bladder structure 302, the patient centering/turning bladder structure 306, and the main air bladder 310. This schematic discloses a valve 324, such as a solenoid valve or other types of valve, that control the movement of the fluid into and out of the patient raising bladder structure 302, the patient centering/turning bladder structure 306, and the main air bladder 310 to perform the functions described herein. The valve 324 is controlled by the controller 222, and may be able to selectively establish fluid communication between the pump 320 and each of the patient raising bladder structure 302, the patient centering/turning bladder structure 306, and the main air bladder 310 or close off such fluid communication. The valve 324 may also be able to vent the patient raising bladder structure 302, the patient centering/turning bladder structure 306, and the main air bladder 310 to atmosphere to deflate the patient raising bladder structure 302, the patient centering/turning bladder structure 306, and the main air bladder 310. It should be understood that additional valves, not shown, may be utilized to carry out the functions of the patient raising bladder structure 302, the patient centering/turning bladder structure 306, and the main air bladder structure 306.

In one exemplary operation of the patient raising device 206, the pump 320 sequentially inflates one or more of the patient raising inflation bladders 304, as shown in FIGS. 18A through 18C to move the patient from the slouched position to a raised position. The controller 222 is configured to control the rate of operation of the patient raising device 206 by controlling the rate of operation of the pump 320 and/or motor 322 in response to receiving the user input signal from one of the user input devices 228, such as the buttons B1 or B2. As will be understood, the pump 320 and/or motor 322 may be the actuator 202 of the patient raising device 206.

In one configuration, the controller 222 is configured to control the rate of operation of the patient raising device 206 based on the user input signal received from the rate selector buttons B13, B14, B15. Alternatively, the controller 222 is configured to control the rate of operation of the patient raising device 206 based on the user input signal and based on the patient condition 234.

For example, if the user depresses button B1 indicating that the user wishes to actuate the patient raising device 206, and depresses button B13 indicating the FAST rate of operation, the controller 222 may control the pump 320 and/or motor 322 to operate at an increased rate of operation in order to increase the rate at which the patient is urged towards the head end of the patient support apparatus 30. In the exemplary embodiment, this entails operating the pump 320 to inflate the patient raising inflation bladders 304 until the patient has reached the desired patient position. This may comprise operating the pump 320 until a current center of gravity of the patient is moved toward the head end of the patient support apparatus 30 by a desired distance.

In another embodiment, the controller 222 controls the rate of operation of the patient raising device 206 based on the user input signal and based on the patient condition 234. For example, if the user depresses button B1 indicating that the user wishes to actuate the patient raising device 206, and depresses button B13 indicating the FAST rate of operation is desired, the controller 222 may query the patient condition 234 to determine whether the user-selected rate of operation is suitable for the patient condition 234. If the FAST rate of operation is not suitable for the patient condition 234, such as when the patient has a neck injury, the controller 222 may determine a desired rate of operation that is suitable for the patient condition 234, and control the pump 320 and/or motor 322 with the desired rate of operation to slow down the rate at which the patient moves towards the head end of the patient support system PS. This slower rate of operation may also avoid disorienting effects on the patient from abrupt movement and reduce shear forces to the patient's skin. In some cases, operation of the patient raising device 206, including the time to inflate/deflate one sequence of the patient raising inflation bladders 304 may be twice as long as the time needed for the same operation if the controller 222 controlled the rate of operation at the FAST rate of operation.

Additionally, the controller 222 may determine a rate of operation for the patient raising device 206 based on other patient-related information. For example, the controller 222 may control the rate of operation for the patient raising device 206 based on the skin condition of the patient, or the patient's movement sensitivity score.

In a similar manner, the controller 222 may control the rate of operation of the patient centering device 210. In one exemplary operation of the patient centering device 210, the pump 320 operates to inflate one or more of the elongate bladders 308 to move the patient toward the centerline CL of the mattress 50. The controller 222 is configured to control the rate of operation of the patient centering device 210 by controlling the rate of operation of the actuator 202, in the illustrated embodiment, the rate of operation of the pump 320 and/or motor 322 in response to receiving the user input signal from one of the user input devices 228, button B3.

In one configuration, the controller 222 is configured to control the rate of operation of the patient centering device 210 based on the user input signal and based on the user input signal received from the rate selector buttons B13, B14, B15. Alternatively, as described above with respect to the patient raising device 206, the controller is configured to control the rate of operation of the patient centering device 210 based on the user input signal and based on the patient condition 234.

During operation of the patient centering device 210, in one embodiment, the elongate bladder 308 that is located on the side of the mattress 50 on which the patient is sensed is first inflated. The elongate bladder 308 may be inflated at a moderate angle such that the patient slowly slides towards the centered position on the centerline CL. In some cases, both of the elongate bladders 308 may be inflated simultaneously, to different levels (e.g., different pressures or angles as measured by pressure sensors or angle sensors in communication with the controller 222) or the same level to keep the patient in the centered position. For example, if the user depresses button B3 indicating that the user wishes to actuate the patient centering device 210, and depresses button B13, indicating that the user wishes to operate at the FAST rate of operation, the controller 222 may query the patient condition 234 to determine whether the user-selected rate of operation is suitable for patient condition 234. If the FAST rate of operation is not suitable for the patient centering device 210 for the patient condition 234, such as when the patient has severe burns, the controller 222 may determine a desired rate of operation that is suitable for the patient condition 234, and control the pump 320 and/or motor 322 with the desired rate of operation to slow down the rate at which the patient is moved towards the longitudinal centerline CL of the patient support apparatus 30. In one embodiment, the controller 222 may control the pump with the desired rate of operation to control the rate at which the patient moves toward the centerline of the patient support surface.

In one exemplary operation of the patient turning device 208, the pump 320 may inflate one or more of the elongate bladders 308 to turn the patient. The controller 222 is configured to control the rate of operation of the patient turning device 208 by controlling the rate of operation of the pump 320 and/or motor 322 in response to receiving the user input signal from one of the user input devices 228, such as buttons B4, B5.

In one configuration, the controller 222 is configured to control the rate of operation of the patient turning device 208 based on the user input signal received from the rate selector buttons B13, B14, B15. Alternatively, the controller 222 is configured to control the rate of operation of the patient turning device 208 based on the user input signal and the based on the patient condition 234.

In one exemplary operation of the patient ingress/egress device 212, the pump 320 may inflate the main air bladder 310 to assist the ingress or egress of the patient from the patient support apparatus 30. The controller 222 is configured to control the rate of operation of the patient ingress/egress device 212 by controlling the rate of operation of the pump 320 and/or motor 322 in response to receiving the user input signal from one of the user input devices 228, button B6.

In one configuration, the controller 222 is configured to control the rate of operation of the patient ingress/egress device 212 based on the user input signal received from the rate selector buttons B13, B14, B15. Alternatively, the controller 222 is configured to control the rate of operation of the patient ingress/egress device 212 based on the user input signal and the patient condition 234.

Figure 22:
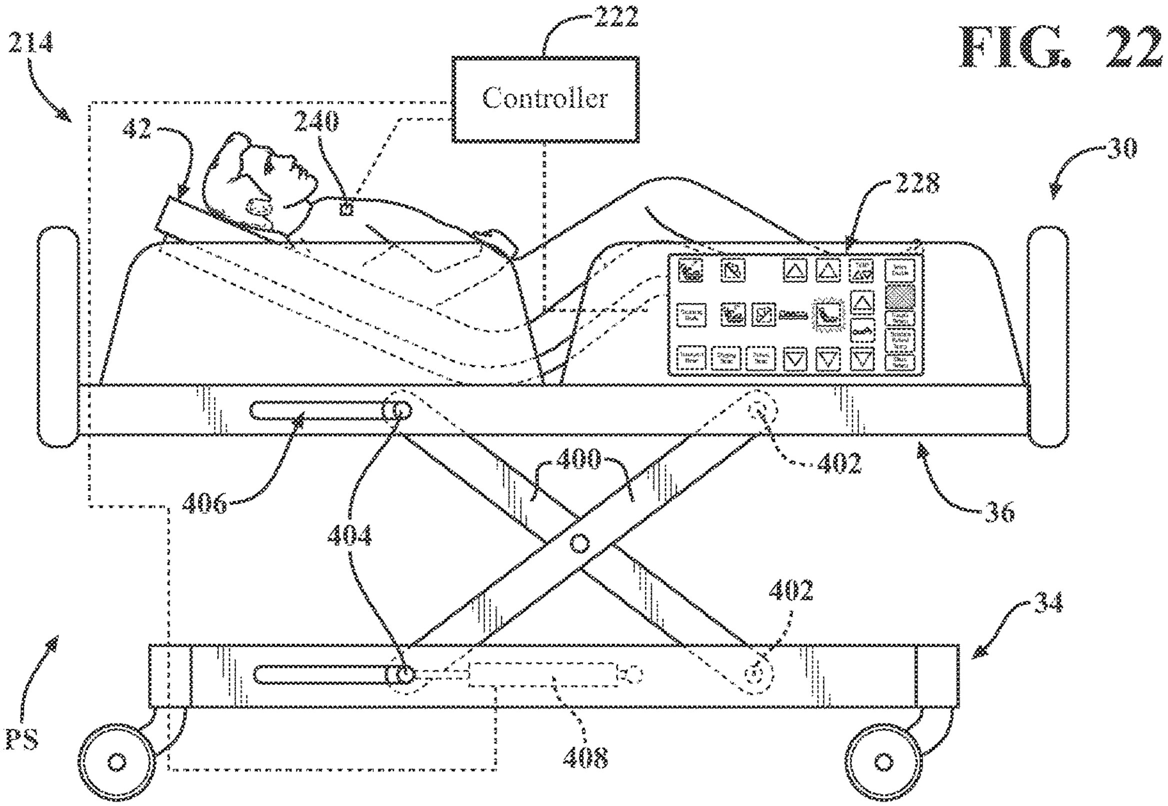
FIG. 22 is a side view of a lift device.

Referring to FIG. 22, the lift device 214 is configured to lift and lower the patient between the minimum and maximum heights of the patient support system PS, and intermediate positions there between. In the exemplary embodiment shown, the lift device 214 comprises a pair of lift arms 400 pivotally connected at a center thereof and arranged in a scissor-lift configuration. The lift arms 400 are movable to raise and lower the patient support surfaces 48, 52 relative to the base 34 and the floor surface. Each of the lift arms 400 have a first end pivotally connected at a fixed pivot point 402 to one of the base 34 and the intermediate frame 36. The lift arms 400 extend from the first end to a second end. A pin 404 is fixed to the second end and arranged to slide in a horizontal guide slot 406 defined in one of the base 34 and the intermediate frame 36.

A lift actuator 408 is fixed at one end to the base 34 and to one of the pins 404 at the other end. When actuated, the lift actuator 408 directly slides the pin 404 in the horizontal guide slot, which also indirectly slides the other pin 404 in the other horizontal guide slot 406, to raise and lower the patient support surface 42. The lift actuator 408 may comprise an electric linear actuator, a hydraulic cylinder, or similar driving mechanism. Other configurations of the lift device 214 are also possible, such as column lift mechanisms shown in FIG. 1A, the lift system of the chair 100, or any other suitable lift mechanism.

In some embodiments, the controller 222 is configured to initiate operation of the lift device 214 in response to receiving a user input signal when the caregiver presses the button B7 or B8 to operate the lift actuator 408 to either lift or lower the patient support surface 48, 52. The controller 222 is further configured to control the rate of operation of the lift device 214 by controlling the rate of operation of the actuator 202, in the illustrated application, the rate of operation of the lift actuator 408 in response to receiving the user input signal from buttons B7, B8.

In certain configurations, the controller 222 is configured to control the rate of operation of the lift device 214 based on the user input signal received from buttons B13, B14, B15. Alternatively, the controller 222 is configured to control the rate of operation of the lift device 214 based on the user input signal and based on the patient condition 234.

For example, if the user depresses button B8 indicating that the user wishes to actuate the lift device 214 to lower the patient support surface 48, 52 and depresses button B13 indicating the FAST rate of operation, the controller 222 may query the patient condition 234 to determine whether the user-selected rate of operation is suitable for the patient condition 234. If the FAST rate of operation is not suitable for the patient condition 234, such as when the patient has a psychological sensitivity to falling as observed by the caregiver or is a fall risk, the controller 222 may determine a desired rate of operation for the patient condition 234, and control the lift actuator 408 with the desired rate of operation to slow down the rate at which the patient moves towards the base 34 of the patient support apparatus 30. The slower rate of operation may minimize the patient's anxiety and/or the likelihood that the patient would fall from the patient support surface 48, 52. The patient's fear of falling may have been mentioned to the caregiver, and the caregiver may have entered this patient condition 234 to the memory 224 through the user input device 228 before actuation of the lift device 214.

In another embodiment, if the user wishes to clean the patient support surfaces 48, 52, 111, the user may actuate the user input device 228 associated with the cleaning mode B18. If the patient position sensor 241 determines that no patient is positioned adjacent to the support surface 48, 52, 111, the controller 222 may control the lift device 214 with the FAST rate of operation. This allows such a user to quickly lower the patient support surface 48, 52, 111 to a convenient height, and clean and sanitize the patient support surface 48, 52, 111, while avoiding potential injury to the patient based on the increased rate of operation.

In yet another embodiment, the patient condition sensor 240 detects that the patient is asleep with a heart rate sensor, an acoustic sensor, a camera (optical or thermal), or other suitable sensor. If the user subsequently decides to actuate the lift device 214 by depressing button B8 with a MEDIUM rate of operation (e.g., the user did not select one of the rate selector buttons or did not depress B8 with an actuation pattern indicating that a SLOW or FAST rate of operation is desired), the controller 222 based on the patient condition 234 (i.e., that the patient is asleep), automatically determines a suitable rate of operation that is desired based on the patient condition 234 "ASLEEP". For example, the controller 222 may determine that the MEDIUM rate of operation is not suitable for a patient that is asleep, and automatically controls the lift device 214 at SLOW rate of operation that is slower than the MEDIUM rate of operation.

If the patient support system PS is not already at the lowered position, upon receiving the user input signal, the controller 222 operates the lift actuator 408 to slowly lower the patient support apparatus 30 to the lowered position. By slowly lowering the patient support apparatus 30, such as at a rate much slower than the MEDIUM rate of operation of the lift device 214 using the nurse control panel NCP, the patient is not awakened. The slower rate of operation may be less likely to wake up a patient.

Figure 23:
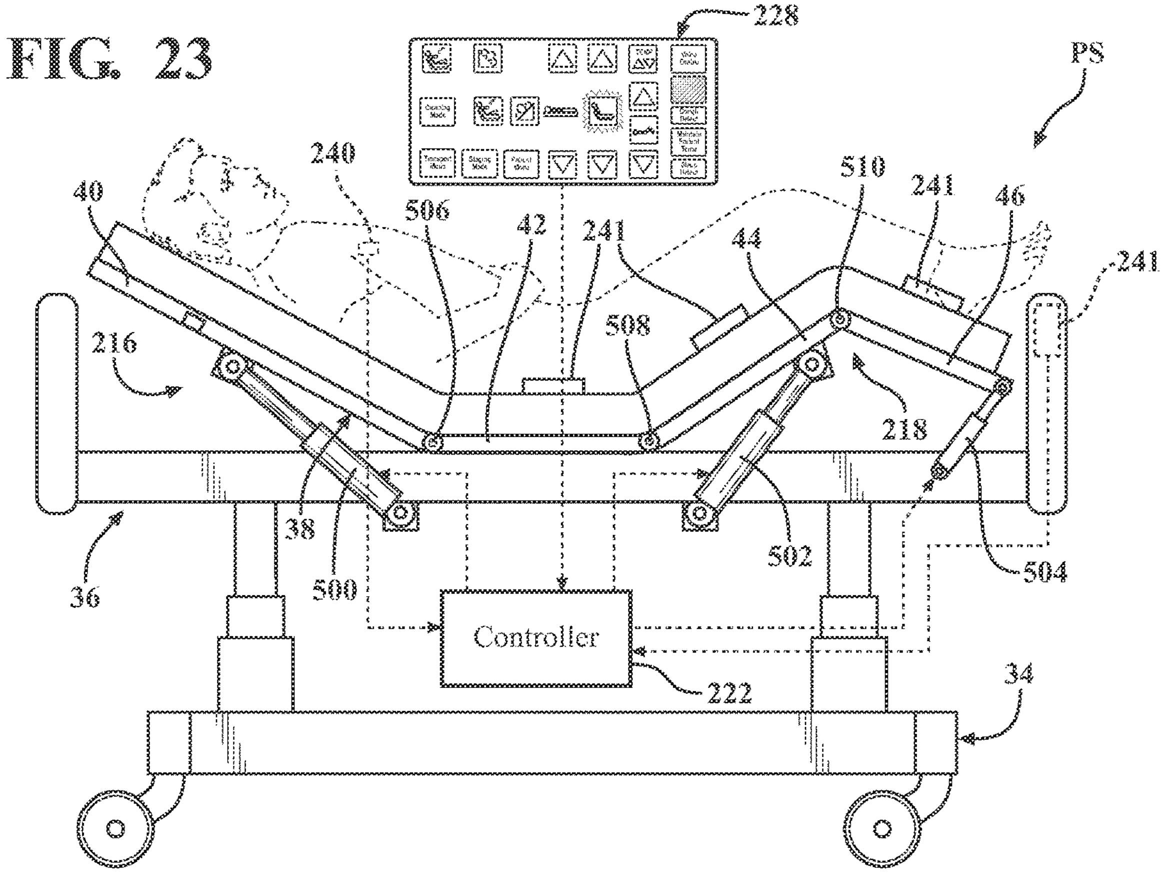
FIG. 23 is a side view of a fowler and gatch adjustment device.

The fowler adjustment device 216 and the gatch adjustment device 218 is configured to articulate the deck 38 of the patient support apparatus 30. Referring to FIG. 23, the fowler adjustment device 216 in the exemplary embodiment comprises a fowler actuator 500 coupled to the fowler section 40. The fowler actuator 500 moves the fowler section 40 relative to the intermediate frame 36. The gatch adjustment device 218 comprises a thigh actuator 502 coupled to, and configured to move, the thigh section 44 and a foot actuator 504 is coupled to, and configured to move, the foot section 46. The fowler actuator 500, thigh actuator 502, and the foot actuator 504 may comprise electric linear actuators that extend between the intermediate frame 36 and the particular deck section being adjusted. For example, as shown in FIG. 23, the fowler section 40 is pivotally connected to the intermediate frame 36 at a fixed pivot 506, the thigh section 44 is pivotally connected to the intermediate frame 36 at a fixed pivot 508, and the foot section 46 is pivotally connected to the thigh section 44 at pivot point 510. The fowler actuator 500 has as a first end pivotally connected to the intermediate frame 36 and a second end pivotally connected to the fowler section 40; the thigh actuator 502 has first end pivotally connected to the intermediate frame 36 and a second end pivotally connected to the thigh section 44; and the foot actuator 504 has a first end pivotally connected to the intermediate frame 36 and a second end pivotally connected to the foot section 46. Actuation of each deck adjustment actuators 500, 502, 504 raises and lowers the respective deck section 40, 44, 46 at various inclination angles relative to the intermediate frame 36. It is contemplated that any suitable deck adjustment system may be utilized in conjunction with the patient support apparatus 30.

As described above, in certain embodiments, the deck adjustment device may be configured to provide coordinated motion between the multiple actuators 500, 502, 504 as described above with reference to the chair 100. For example, the patient support deck 38 can be configured to assume a chair state, a bed exit state, a flat state, etc. Thus, the controller 222 may be configured to control the actuators 500, 502, 504 such that the actuators 500, 502, 504 reach the desired state simultaneously, or substantially simultaneously.

In some embodiments, the controller 222 is configured to initiate operation of the fowler adjustment device 216 in response to receiving the user input signal from button B9. The controller 222 is further configured to control the rate of operation of the fowler adjustment device 216 by controlling the rate of the actuator 202, in the illustrated embodiment, the rate of operation of the fowler actuator 500 in response to receiving the user input signal from one of the user input devices 228, such as the buttons B9 or B10.

In one configuration, the controller 222 is configured to control the rate of operation of the fowler adjustment device 216 based on the user input signal received from the buttons B13, B14, B15. Alternatively, the controller 222 is configured to control the rate of operation of the fowler adjustment device 216 based on the user input signal and based on the patient condition 234.

For example, if the user depresses button B9 indicating that the user wishes to actuate the fowler adjustment device 216 to tilt away from the intermediate frame 36, and depresses button B13 indicating the FAST rate of operation is desired, the controller 222 may query the patient condition 234 to determine whether the user-selected rate of operation is suitable for the patient condition 234. If the FAST rate of operation is not suitable for the patient condition 234, such as when the patient has a neck injury, the controller 222 may determine a desired rate of operation that is suitable for the patient condition 234, and automatically control the fowler actuator 500 with the desired rate of operation to slow down the rate at which the patient tilts away from the intermediate frame 36 of the patient support apparatus 30. This slower rate of operation may reduce the patient's neck pain. Additionally, the controller 222 may determine a rate of operation for the fowler adjustment device 216 based on other patient-related information. For example, the controller 222 may control the rate of operation for the fowler adjustment device 216 based on the skin condition of the patient, or the patient's movement sensitivity score.

The transport device 220 may comprise the one or more powered wheel assemblies 68 (See FIG. 2). Controller 222 is configured to control the wheel motors 72 such that the wheels 70 rotate about the rotational axis 74. The direction and rate of the powered wheel assemblies 68 can be controlled based on the user input device 228. In one embodiment, buttons B16 are force sensors that are provided on footboard 64 that detect a magnitude of forces exerted by a caregiver on the patient support apparatus 30. The controller 222 may generally power the powered wheel assemblies 68 proportionally to the forces exerted by a caregiver on buttons B16. For example, in some embodiments, controller 222 supplies power to the powered wheel assemblies 68 in increments, rather than a continuous fashion. Of course, in some embodiments, more than one powered wheel assembly 68 can be driven as a pair with the same power level, while the rear wheels could be driven as a separate pair (with the same power level as each other, but not necessarily the same power level as the front wheels).

The controller 222 is configured to control the rate of operation of the transport device 220 by controlling the rate of operation of the actuator 202, in this example, the rate of operation of the wheel motor 72 that rotate the wheels 70 in response to receiving the user input signal from one of the user input devices 228, such as buttons B16.

In one configuration, the controller 222 is configured to control the rate of operation of the transport device 220 based on the user input signal received from the buttons B13, B14, B15. Alternatively, the controller 222 is configured to control the rate of operation of the transport device 220 based on the user input signal and based on the patient condition 234.

For example, if the user applies a force to one or both of buttons B16 indicating that the user desires to operate the powered wheel assembly 68 at the FAST rate of operation, the controller 222 may query the patient condition 234 to determine whether the user-selected rate of operation is suitable for the patient condition 234. If the FAST rate of operation is not suitable for the patient condition 234, such as when the patient had major spinal surgery a few hours prior to transport, the controller 222 may determine a desired rate of operation that is suitable for the patient condition 234, and control the powered wheel assemblies 68, i.e., the wheel motors 72, with the SLOW rate of operation to slow down the rate at which the patient support apparatus 30 moves along the floor. This slower rate of operation may minimize the pain experienced by the patient. Additionally, the controller 222 may determine a rate of operation for the transport device 220 based on other patient-related information. For example, the controller 222 may control the rate of operation for the transport device 220 based on the skin condition of the patient, or the patient's movement sensitivity score.

In another embodiment, if the user wishes to transport the patient support apparatus 30 across a long distance, the user may actuate the user input device 228 associated with the transport mode B19. If the patient presence sensor 241 determines that no patient is positioned adjacent to the support surface 48, 52, 111, and transmits the corresponding patient presence input signal to the controller 222, the controller 222 controls the transport device 220 with the FAST rate of operation. This allows such a user to quickly move the patient support apparatus 30 while avoiding potential injury to any patient. In certain embodiments, the TRANSPORT mode may only be selected if the identification device 232 determines that the person adjacent to the support surface 48, 52, 111 is a TRANSPORTER (i.e., a person responsible for moving the patient support system PS).

As described the above, the controller 222 may control the rate of operation for devices other than those described above based on the user input device and/or patient condition.

It will be further appreciated that the terms “include,” “includes,” and “including” have the same meaning as the terms “comprise,” “comprises,” and “comprising.”

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support system for a patient, the patient support system comprising:
- a base;
- a patient support surface supported by the base;
- an actuator configured to move the patient disposed on the patient support surface relative to the base, the actuator being operable at different rates of actuation, wherein the different rates of actuation of the actuator defines a full range of available rates;
- a user input device configured to generate a user input signal, the user input device including a voice actuation interface;
- an identification device configured to identify a role of a caregiver adjacent to the patient support surface; and
- a controller disposed in communication with the actuator, the user input device, and the identification device, the controller being configured to:
- enable the voice actuation interface based on the identified role of the caregiver adjacent to the patient support surface determined by the identification device, and to
- transmit an output signal to the actuator to control the actuator to move the patient disposed on the patient support surface relative to the base in response to the user input signal generated by the voice actuation interface, and
- permit operation of the actuator across at least one of: the full range of available rates and less than the full range of available rates based on the identified role of the caregiver adjacent to the patient support surface determined by the identification device.

2. The patient support system of claim 1, wherein the voice actuation interface includes a microphone in communication with the controller to receive one or more voice activation commands.

3. The patient support system of claim 2, wherein the one or more voice activation commands includes a stop command; and
- wherein the controller is further configured to interrupt operation of the actuator in response to receiving the stop command from the voice actuation interface.

4. The patient support system of claim 3, wherein the controller is further configured to disable operation of the identification device in response to receiving the stop command for interrupting operation of the actuator in response to receiving the stop command from the patient disposed on the patient support surface.

5. The patient support system of claim 2, wherein the one or more voice activation commands includes a fast speed command; and
- wherein the controller is further configured to control operation of the actuator at a first predetermined rate in response to receiving the fast speed command from the voice actuation interface.

6. The patient support system of claim 5, wherein the one or more voice activation commands includes a slow speed command;
- wherein the controller is further configured to control operation of the actuator at a second predetermined rate in response to receiving the slow speed command from the voice actuation interface; and
- wherein the second predetermined rate is slower than the first predetermined rate.

7. The patient support system of claim 1, further comprising a voice activation enabling device in communication with the controller; and
- wherein actuation of the voice activation enabling device enables the voice actuation interface to provide the user input signal.

8. The patient support system of claim 7, wherein the voice activation enabling device is located on a portable electronic device configured for use by a caregiver.

9. The patient support system of claim 7, wherein the voice activation enabling device comprises at least one of a button, a gesture sensing device, a microphone, a foot pedal, and a sensor.

10. The patient support system of claim 1, wherein the controller is further configured to determine a desired rate of operation for the actuator based on a combination of the user input signal and one or more of:
- medical procedure data comprising a type of medical procedure undergone by the patient, a duration since last medical procedure, a duration since admittance, or combinations thereof;
- patient characteristic data comprising height, fall risk data, width, age, weight, body mass index, or combinations thereof;
- caregiver observation data comprising psychological data, phobia data, pain sensitivity data, nausea data, or combinations thereof;
- medication data;
- prior injury data; or
- combinations thereof.

11. The patient support system of claim 1, wherein the controller is further configured to determine a desired rate of operation for the actuator based on the user input signal.

12. The patient support system of claim 11, further comprising memory disposed in electronic communication with the controller to store data associated with a plurality of operational modes, each operational mode corresponding to a predetermined rate of operation for the actuator; and wherein the controller is further configured to determine the desired rate of operation of the actuator based on the operational mode selected using the voice actuation interface.

13. The patient support system of claim 12, wherein the plurality of operational modes comprise one or more of a patient mode, a cleaning mode, or a transport mode.

14. The patient support system of claim 12, wherein the controller is further configured to enable or disable selection of one or more operational modes based on the identified role of the caregiver adjacent to the patient support surface.

15. The patient support system of claim 12, wherein the controller is further configured to select one of the operational modes based on the identified role of the caregiver adjacent to the patient support surface.

16. The patient support system of claim 1, wherein the user input device further includes one or more buttons for controlling operation of the actuator.

17. The patient support system of claim 16, wherein the controller is further configured to enable or disable operation of the one or more buttons based on the identified role of the caregiver adjacent to the patient support surface.

18. The patient support system of claim 1, further comprising a sensing system in communication with the controller, the sensing system configured to provide a sensor input signal to the controller.

19. The patient support system of claim 1, wherein the identification device is configured to identify a second role of a second caregiver adjacent to the patient support surface; and wherein the controller is configured to transmit the output signal to the actuator to control the actuator:

at a first rate of actuation in response to the user input signal generated by the voice actuation interface utilized by the caregiver with the role identified by the identification device, and at a second rate of actuation, different from the first rate of actuation, in response to the user input signal generated by the voice actuation interface utilized by the second caregiver with the second role identified by the identification device.

* * * * *